(12) United States Patent
Emalfarb

(10) Patent No.: US 11,103,160 B2
(45) Date of Patent: *Aug. 31, 2021

(54) SYSTEMS AND METHODS FOR VERIFIED BIOMEASUREMENTS

(71) Applicant: MEDF LLC, Chicago, IL (US)

(72) Inventor: Michael Evan Emalfarb, Chicago, IL (US)

(73) Assignee: MEDF LLC, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/148,438

(22) Filed: Jan. 13, 2021

(65) Prior Publication Data
US 2021/0128021 A1 May 6, 2021

Related U.S. Application Data

(63) Continuation-in-part of application No. 15/866,447, filed on Jan. 9, 2018, now Pat. No. 10,898,111, which is a continuation of application No. 15/787,499, filed on Oct. 18, 2017, now Pat. No. 9,901,289, which is a
(Continued)

(51) Int. Cl.
| | |
|---|---|
| *A61B 5/1171* | (2016.01) |
| *G01G 23/37* | (2006.01) |
| *G01G 19/50* | (2006.01) |
| *G01G 19/44* | (2006.01) |
| *G01G 23/42* | (2006.01) |
| *G01G 21/28* | (2006.01) |
| *A61B 5/107* | (2006.01) |
| *G06K 9/00* | (2006.01) |

(52) U.S. Cl.
CPC .......... *A61B 5/1079* (2013.01); *A61B 5/1072* (2013.01); *A61B 5/1176* (2013.01); *G01G 19/44* (2013.01); *G01G 19/50* (2013.01); *G01G 21/283* (2013.01); *G01G 23/3728* (2013.01); *G01G 23/3735* (2013.01); *G01G 23/42* (2013.01); *G06K 9/00885* (2013.01); *A47G 2200/226* (2013.01)

(58) Field of Classification Search
CPC ...... G01G 19/44; G01G 19/50; G01G 21/283; G01G 23/3728; G01G 23/3735; G01G 23/42; G06K 9/00885; A61B 5/1072; A61B 5/1079; A61B 5/1176; A47G 2200/226
See application file for complete search history.

(56) References Cited

U.S. PATENT DOCUMENTS

| | | | | |
|---|---|---|---|---|
| 8,901,442 B1* | 12/2014 | Dilone | ................... | G01S 19/16 177/238 |
| 8,902,045 B1* | 12/2014 | Linn | ................... | G06K 9/00288 340/5.83 |
| 9,119,539 B1* | 9/2015 | Dotan | ................ | A61B 5/02438 |

(Continued)

*Primary Examiner* — Natalie Huls
(74) *Attorney, Agent, or Firm* — Nixon Peabody LLP

(57) ABSTRACT

A method includes generating, via a camera, image data that is reproducible as an image of at least a portion of a subject. The method also includes receiving, via a sensor, first biomeasurement data associated with the subject, the first biomeasurement data including a first biomeasurement of the subject. The method also includes verifying the first biomeasurement of the subject based at least in part on a comparison between at least a portion of the image data and at least a portion of the first biomeasurement data.

22 Claims, 23 Drawing Sheets

Related U.S. Application Data continuation-in-part of application No. 15/490,869, filed on Apr. 18, 2017, now abandoned.

(60) Provisional application No. 63/026,643, filed on May 18, 2020, provisional application No. 63/019,111, filed on May 1, 2020, provisional application No. 62/324,781, filed on Apr. 19, 2016.

(56) References Cited

U.S. PATENT DOCUMENTS

| | | | |
|---|---|---|---|
| 9,358,426 B2* | 6/2016 | Aragones | G16H 50/70 |
| 9,498,137 B2 | 11/2016 | Kovacs | |
| 9,901,289 B1 | 2/2018 | Emalfarb | |
| 10,515,309 B1 | 12/2019 | McNamara | |
| 2002/0134589 A1 | 9/2002 | Montagnino | |
| 2010/0051353 A1 | 3/2010 | Swan | |
| 2014/0032234 A1* | 1/2014 | Anderson | A61B 5/112 705/2 |
| 2014/0311215 A1* | 10/2014 | Keays | A61B 5/082 73/23.3 |
| 2015/0045632 A1* | 2/2015 | Bagan | G06Q 20/18 600/301 |
| 2015/0294641 A1* | 10/2015 | Jones | A01K 97/00 345/520 |
| 2015/0302721 A1* | 10/2015 | Schmidt | G01G 19/445 5/93.1 |
| 2016/0038037 A1 | 2/2016 | Kovacs | |
| 2016/0331244 A1* | 11/2016 | Barton-Sweeney | A61B 5/024 |
| 2016/0378924 A1 | 12/2016 | Bagan | |
| 2017/0061224 A1* | 3/2017 | Moliner | G06F 3/041 |
| 2017/0095153 A1* | 4/2017 | Bardy | A61B 5/363 |
| 2017/0143282 A1* | 5/2017 | Kovacs | A61B 5/0022 |
| 2017/0188960 A1* | 7/2017 | Banet | A61B 5/02427 |
| 2017/0206329 A1* | 7/2017 | Capocasale | G16H 10/60 |
| 2017/0220040 A1 | 8/2017 | London | |
| 2017/0300743 A1 | 10/2017 | Emalfarb | |
| 2018/0011973 A1* | 1/2018 | Fish | G16H 40/67 |
| 2018/0168517 A1 | 6/2018 | Wachi | |
| 2018/0296136 A1 | 10/2018 | Foxlin | |
| 2019/0362546 A1 | 11/2019 | Wayenberg | |

* cited by examiner

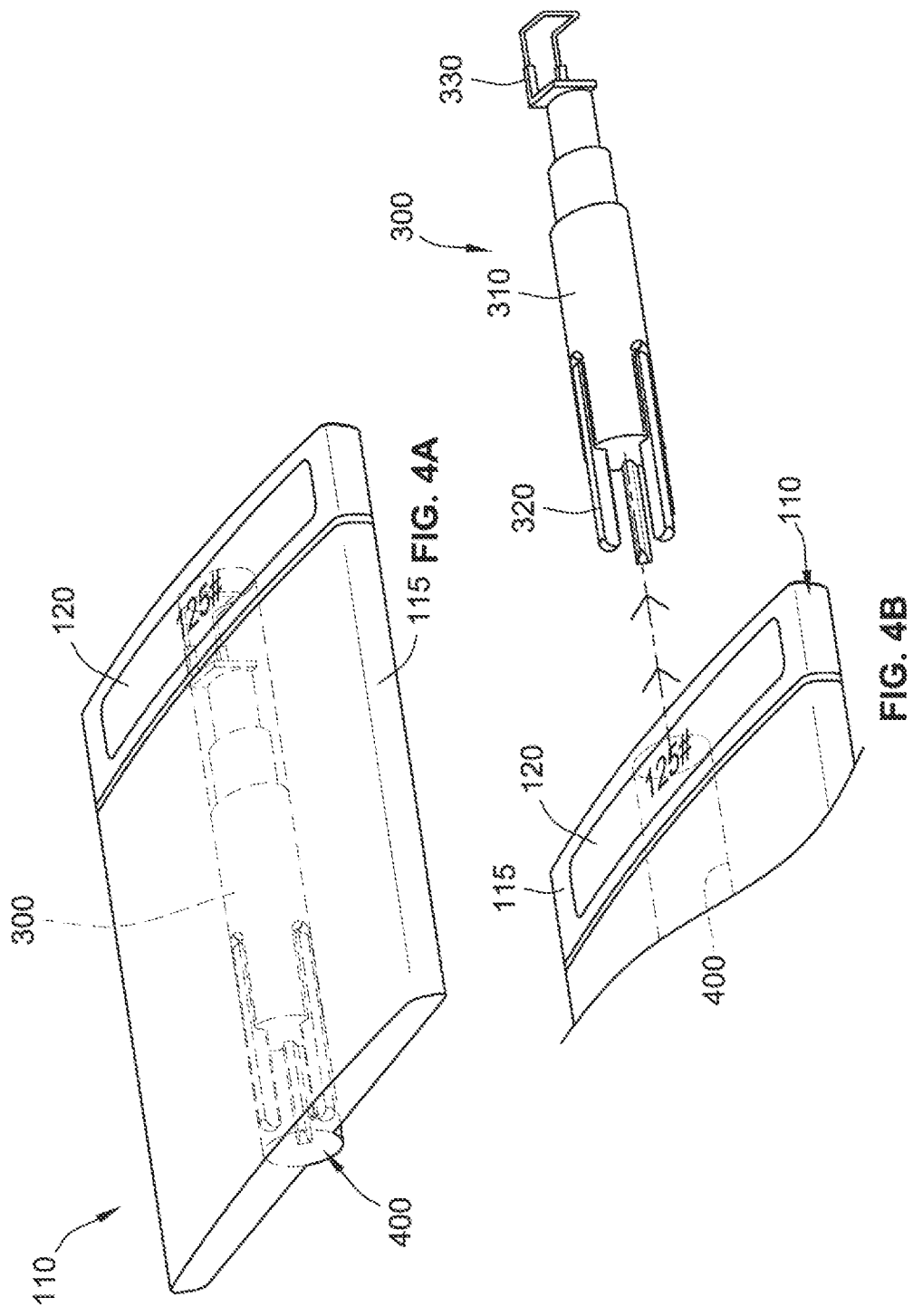

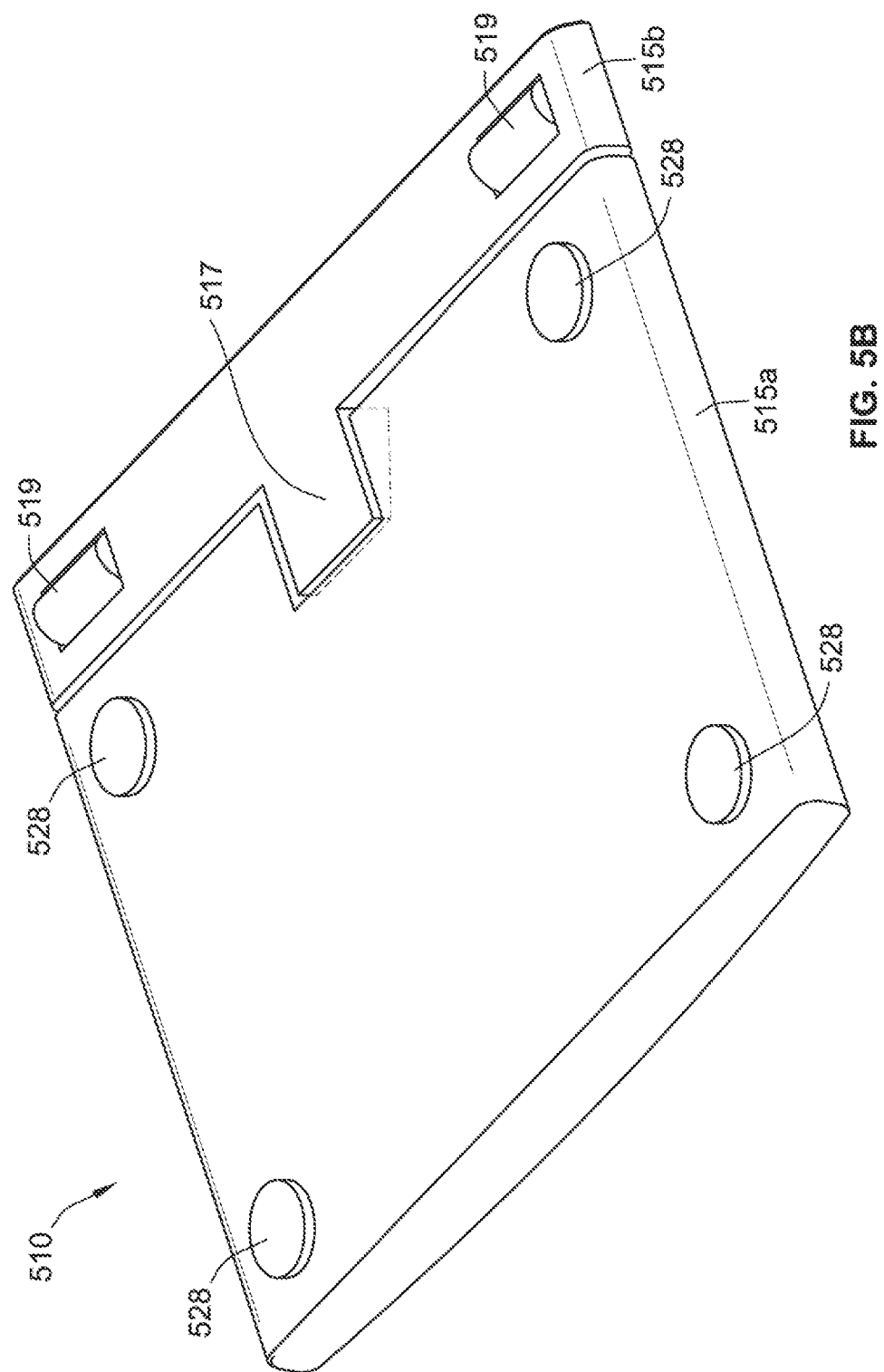

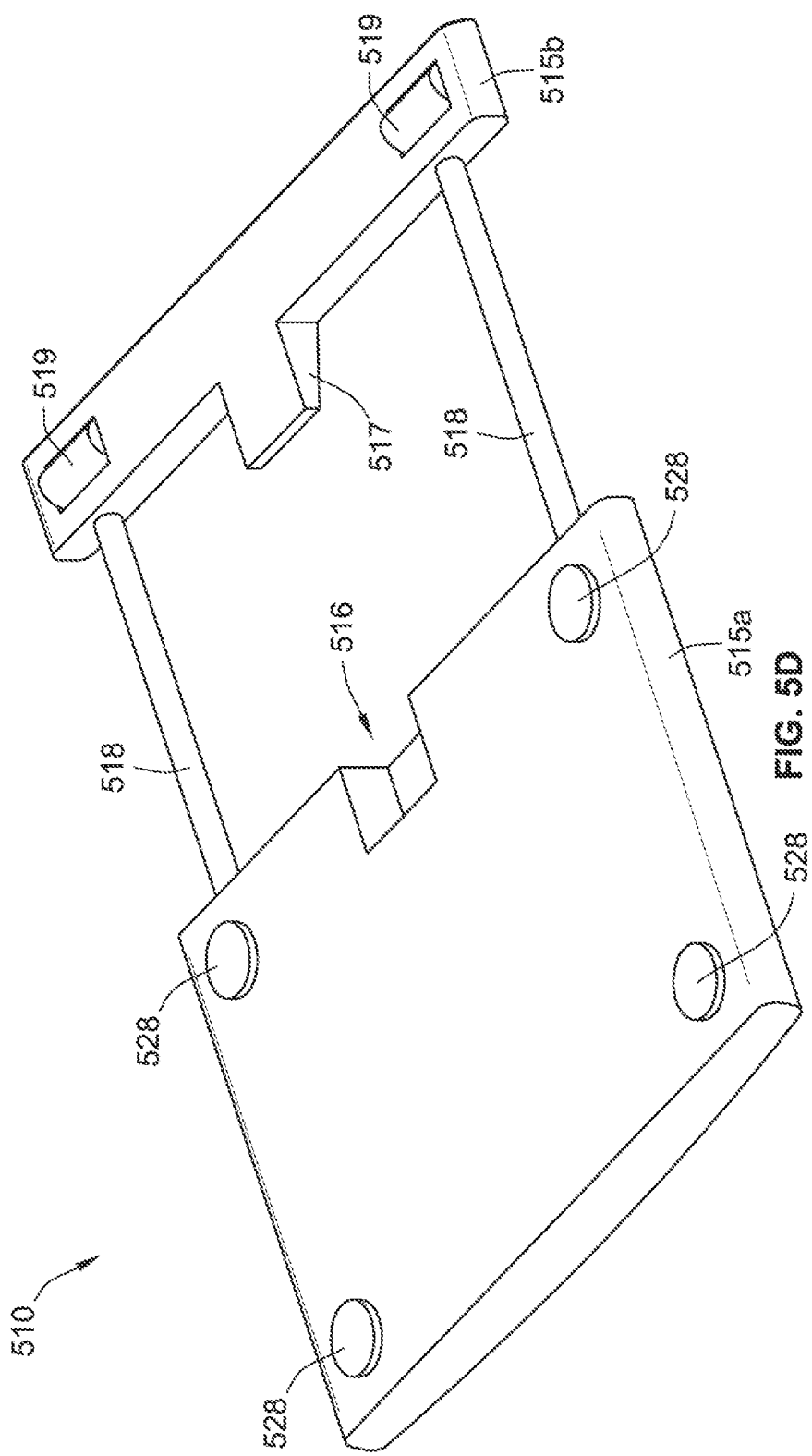

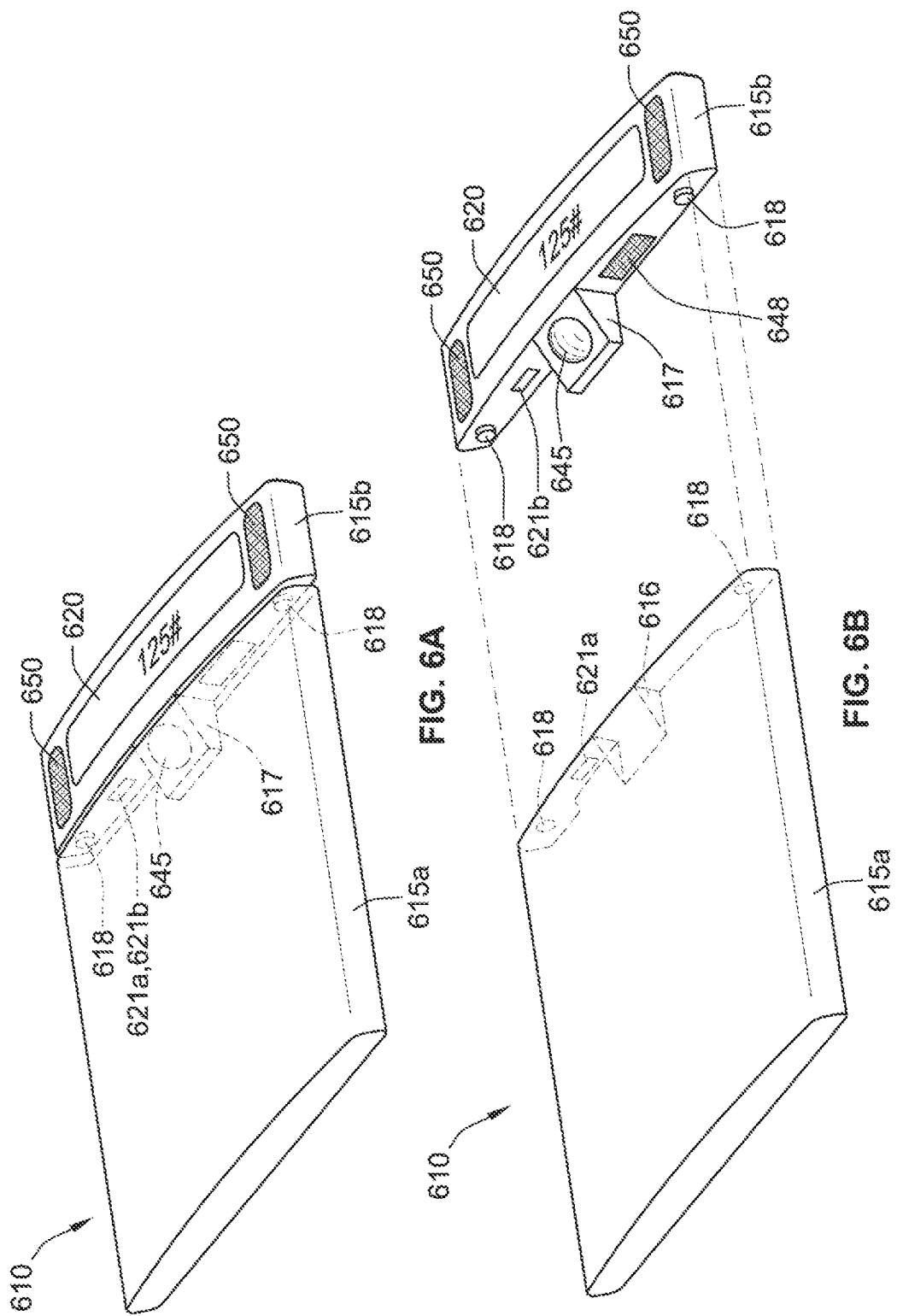

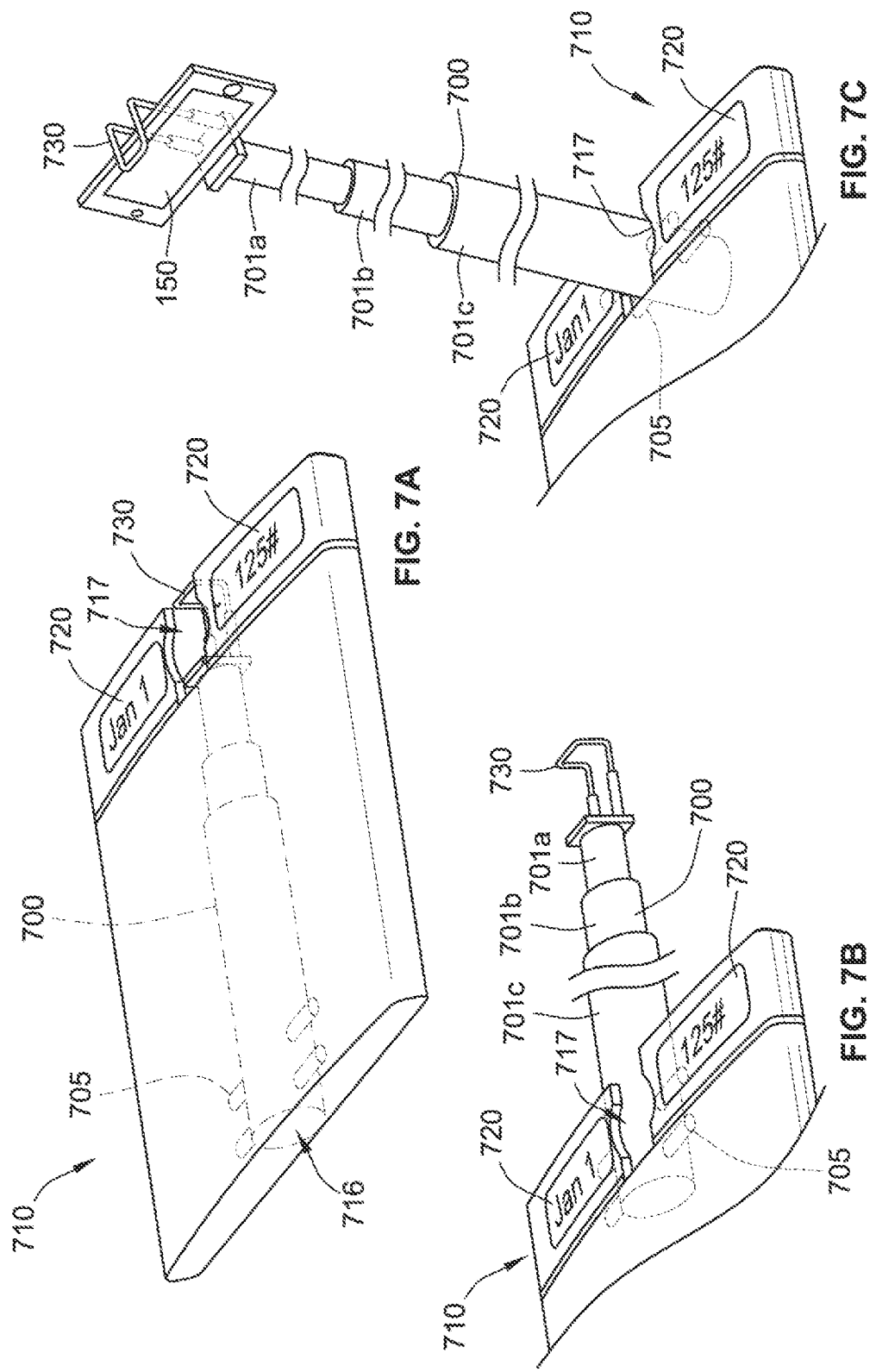

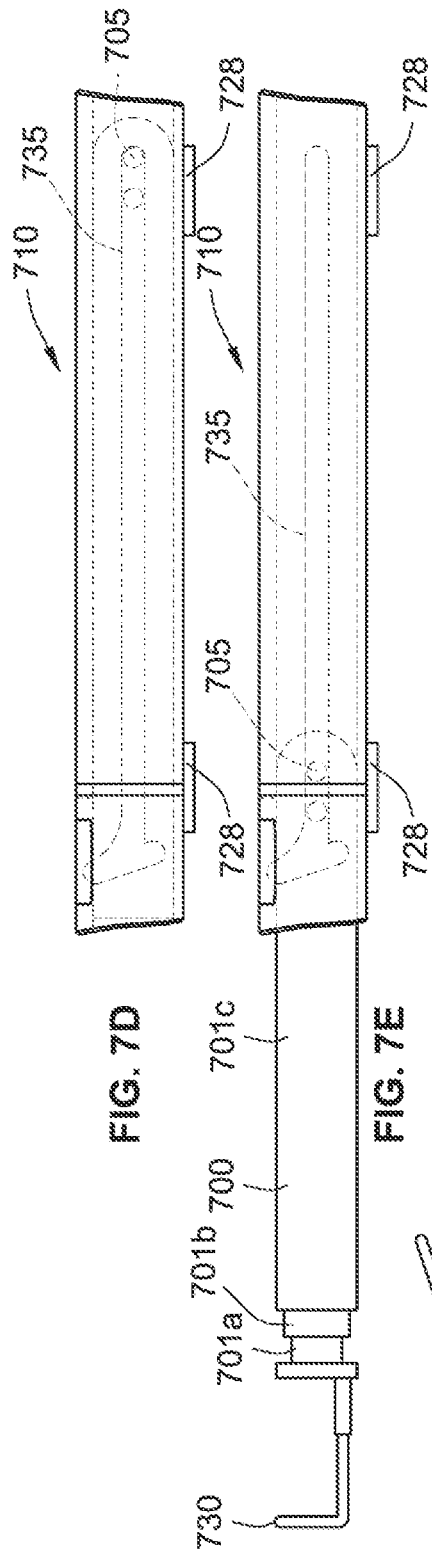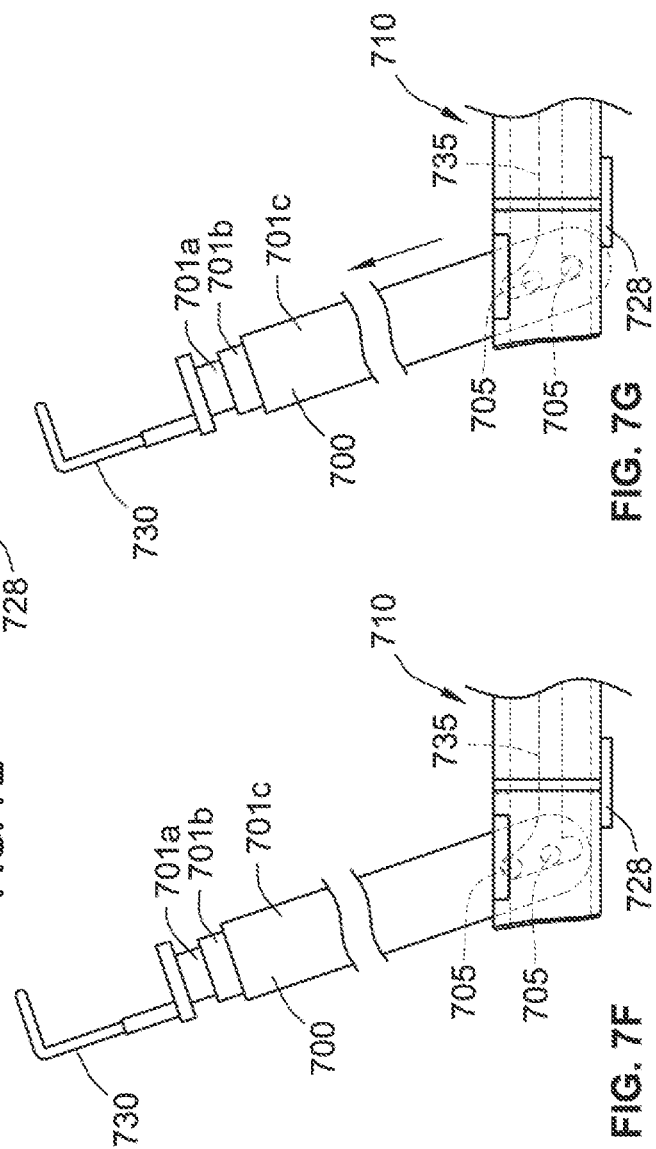

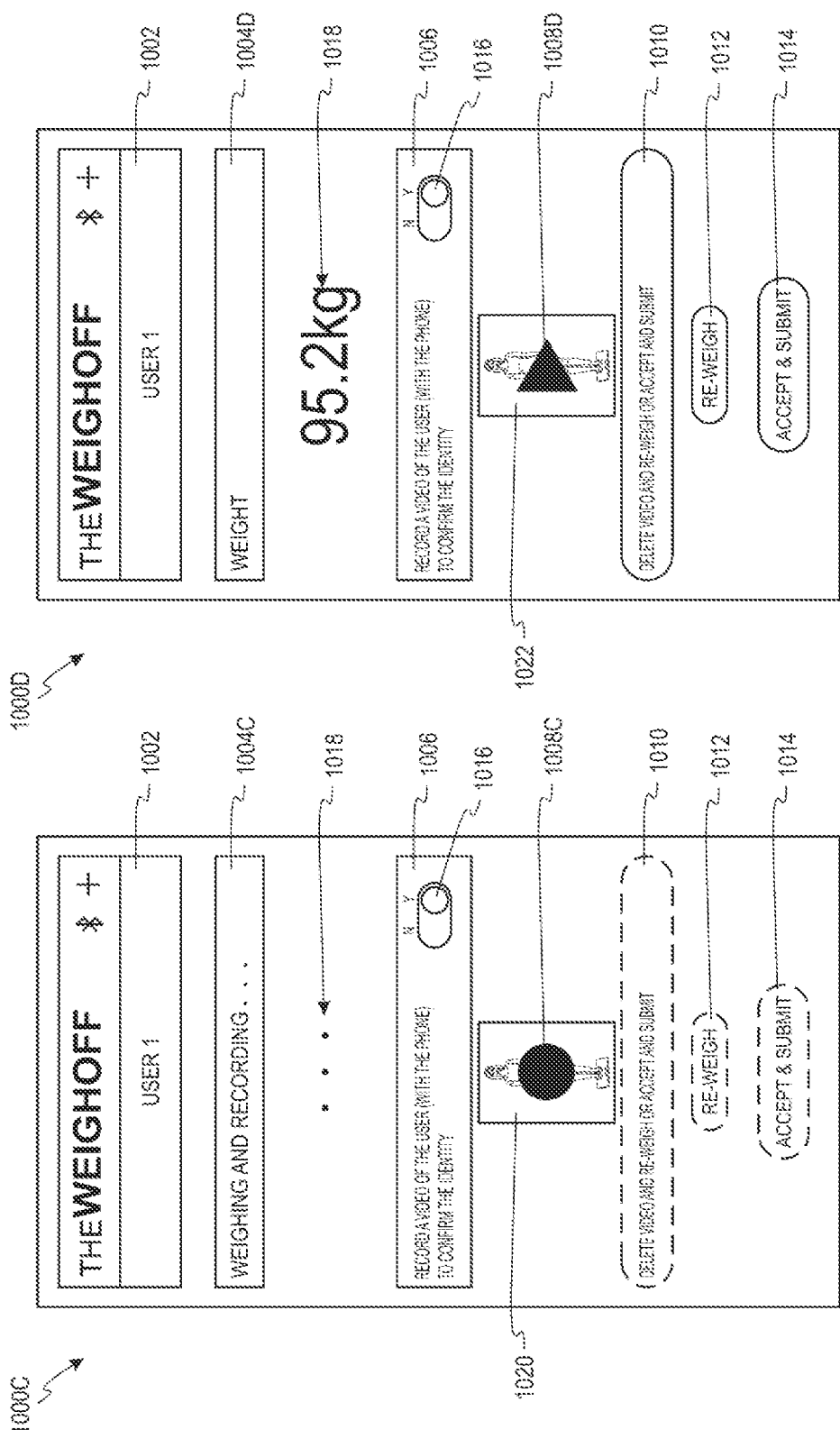

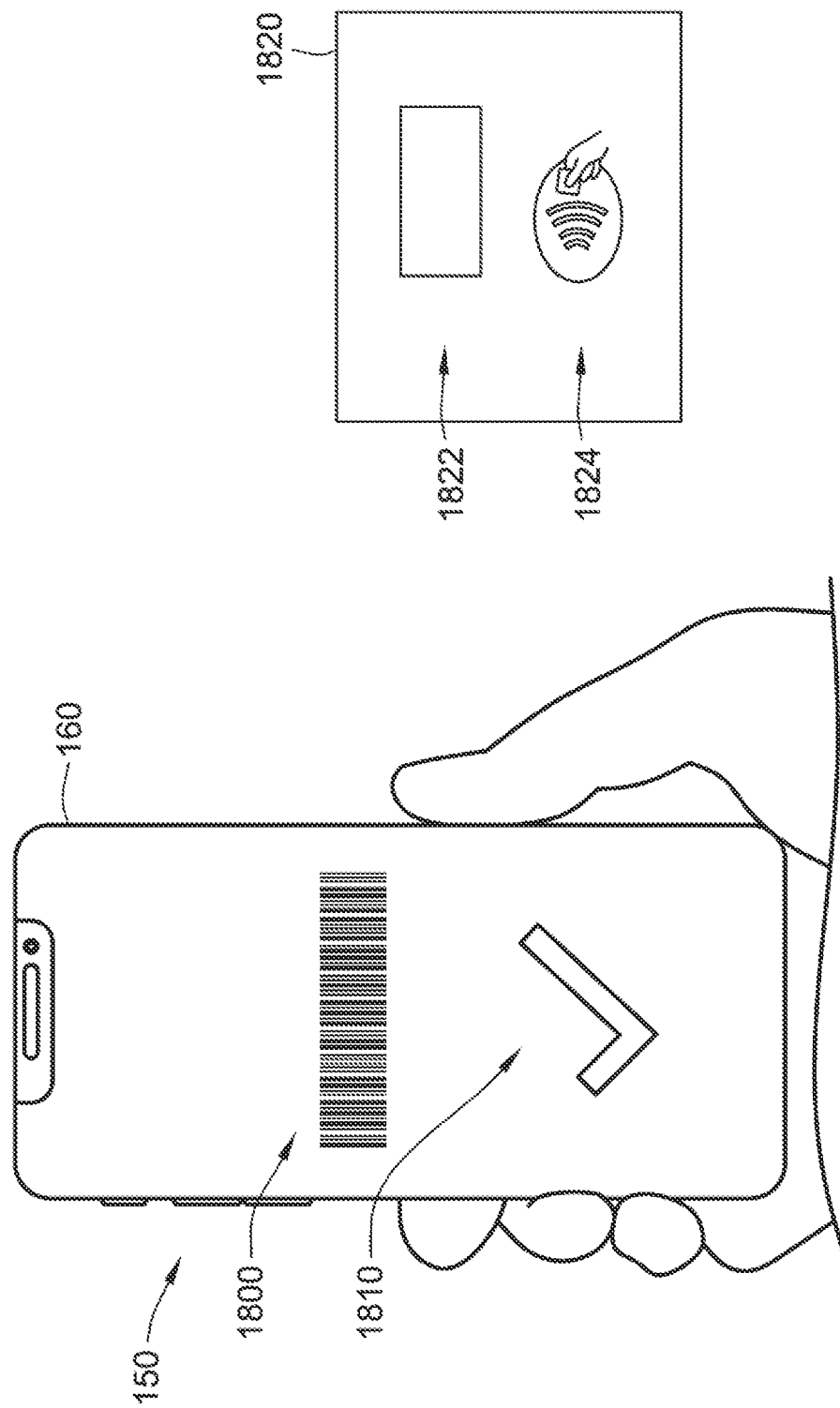

SYSTEMS AND METHODS FOR VERIFIED BIOMEASUREMENTS

CROSS-REFERENCE TO RELATED APPLICATIONS

This application is a continuation-in-part of U.S. patent application Ser. No. 15/866,447, filed Jan. 9, 2018, now allowed, which is a continuation of U.S. patent application Ser. No. 15/787,499, filed Oct. 18, 2017, now U.S. Pat. No. 9,901,289, which is a continuation-in-part of U.S. patent application Ser. No. 15/490,869, filed Apr. 18, 2017, which claims the benefit of and priority to U.S. Provisional Application No. 62/324,781, filed Apr. 19, 2016; this application also claims the benefit of and priority to U.S. Provisional Application No. 63/019,111, filed May 1, 2020, and U.S. Provisional Application No. 63/026,643, filed May 18, 2020, all of the above listed applications are hereby incorporated by reference herein in their entireties.

TECHNICAL FIELD

This disclosure relates generally to biomeasurement devices with verification systems and methods of using the same.

BACKGROUND

Biomeasurements of a subject are useful for a variety of applications. However, in cases where the biomeasurement is taken by the subject (e.g., as opposed to being taken or administered by a third party), it is useful to verify the biomeasurement.

For example, weight loss competitions require users to conduct one or more weigh-ins to track performance. Preventing cheating is paramount to conducting a fair and enjoyable competition. Prior competitions completely ignore and/or leave room for error in the verification of a contestant's identify and/or accurate weight during a weigh-in. Thus, a need exists for a method and system to verify the identities of weight loss competition contests and to verify their weigh-ins.

As another example, it is useful to identify symptomatic individuals based on one or more biomeasurements (e.g., body temperature) that are indicative of an infection to reduce or prevent the spread of infectious diseases. If the biomeasurement(s) indicate that an individual is infected (e.g., based on elevated body temperature), the individual should preferably be restricted from entering one or more locations (e.g., a place of employment) to aid in preventing the infected individual from communicating the disease to others (e.g., which could facilitate the growth of an epidemic or pandemic). However, the biomeasurements may not be accurate if taken by the individual (e.g., as opposed to a medical provider), either due to unintentional error(s) by the individual in performing the biomeasurement or intentional manipulation of the results so as to avoid the imposition of restrictions on movement. The present disclosure is directed to solving these problems and addressing other needs.

SUMMARY

According to some implementations of the present disclosure, a method includes generating, via a camera of an electronic device, video data that is reproducible as a visual video clip of at least a portion of a subject. The method includes determining, via a biomeasurement device, a first biomeasurement associated with the subject. The method also includes generating a data file including (i) the first biomeasurement associated with the subject, (ii) at least a portion of the video data, and (iii) first time data associated with the first biomeasurement. The method further includes verifying the first biomeasurement of the subject based at least in part on the video data included in the generated data file.

According to some implementations of the present disclosure, a method includes causing an electronic device to communicate a first prompt to a subject to generate first biomeasurement data. The first biomeasurement data includes (i) a first biomeasurement of the subject determined by a biomeasurement device, (ii) first video data generated by a camera of the electronic device, the first video data being reproducible as a first video clip of at least a portion of the subject and at least a portion of the biomeasurement device, and (iii) time data corresponding to a time that the biomeasurement of the subject was determined by the biomeasurement device and a time that the video data was generated by the camera of the electronic device. The method includes verifying the first biomeasurement of the subject based at least in part on the first video data and the time data. The method also includes comparing the first verified biomeasurement data to a predetermined threshold. The method further includes determining a first access level for the subject for a first location based at least in part on the comparison between the first verified biomeasurement data and the predetermined threshold.

According to some implementations of the present disclosure, a method includes receiving (i) a first verified biomeasurement associated with a subject, the first verified biomeasurement being associated with a first time, (ii) medical data associated with the subject, or (iii) both (i) and (ii). The method also includes determining a level of access for the subject to one or more locations based at least in part on (i) the first verified biomeasurement associated with the subject, (ii) the first medical data associated with the subject, or (iii) both (i) and (ii), wherein the level of access aids in preventing the subject from communicating a disease to one or more third parties at the one or more locations.

According to some implementations of the present disclosure, a method includes generating, via a camera, image data that is reproducible as an image of at least a portion of a subject. The method also includes receiving, via a sensor, first biomeasurement data associated with the subject, the first biomeasurement data including a first biomeasurement of the subject. The method further includes verifying the first biomeasurement of the subject based at least in part on a comparison between at least a portion of the image data and at least a portion of the first biomeasurement data.

According to some implementations of the present disclosure, a system includes a camera, a sensor, a control system, and a memory. The camera is configured to generate image data that is reproducible as an image of at least a portion of a subject. The sensor is configured to generate first biomeasurement data associated with the subject. The control system comprises one or more processors. The memory has stored thereon machine readable instructions that are executable by the one or more processors to cause the control system to verify a first biomeasurement of the subject based at least in part on the image data and the biomeasurement data, compare the first verified biomeasurement to a predetermined threshold, and determine a first level of access for the subject to one or more locations based at least in part on the comparison between the first verified biomeasurement and the predetermined threshold.

According to some implementations of the present disclosure, a scale includes a housing, an electronic display, a wireless communication module, one or more processors, and a memory device. The housing is configured to support a user thereon. The electronic display is coupled to the housing for displaying a body weight of the user. The wireless communication module is configured to wirelessly communicate with an electronic device. The memory device stores instructions that, when executed by at least one of the one or more processors, cause the scale to (1) determine the body weight of the user supported by the housing, and (2) wirelessly transmit instructions to the electronic device. The instructions direct the electronic device to generate image data that is reproducible as a visual image of the user supported on the housing of the scale at about the same time that the scale determines the body weight of the user.

According to some implementations of the present disclosure, a scale includes a housing, an electronic display, a wireless communication module, one or more processors, and a memory device. The housing is configured to support a user thereon. The electronic display is coupled to the housing for displaying a body weight of the user. The wireless communication module is configured to wirelessly communicate with an electronic device. The memory device stores instructions that, when executed by at least one of the one or more processors, cause the scale to: (1) determine the body weight of the user supported by the housing, (2) wirelessly access the electronic device to cause the electronic device to generate image data that is reproducible as a visual image of the user supported on the housing of the scale, and (3) wirelessly receive the image data from the electronic device.

According to some implementations of the present disclosure, a digital bathroom scale for use in a weight loss competition includes a housing, an electronic display, a wireless communication module, one or more processors, and a memory device. The housing is configured to support a user thereon. The electronic display is coupled to the housing for displaying a body weight of the user. The wireless communication module is configured to wirelessly communicate with an electronic device. The memory device stores instructions that, when executed by at least one of the one or more processors, cause the scale to: (1) determine the body weight of the user supported by the housing and (2) wirelessly transmit weight data representative of the body weight of the user supported by the housing, via the wireless communication module, to the electronic device for inclusion in a data file. Responsive to the wireless transmission of the weight data, the electronic device: (A) generates image data that is reproducible as a visual image of the user supported on the housing of the scale, and (B) wirelessly transmits, via a wireless communication module of the electronic device, the data file to a server for verification of the body weight of the user. The data file includes the weight data, the image data, and time data corresponding to a date and time that the body weight of the user was determined.

According to some implementations of the present disclosure, a weight verification system includes a scale having a housing, an electronic display, one or more processors, a wireless communication module, and a memory device storing instructions that, when executed by at least one of the one or more processors, cause the system to: (1) determine a body weight of a user supported by the housing of the scale and (2) generate image data that is reproducible as a head-to-toe visual image of the user supported on the housing of the scale at about the same time that the scale determines the body weight of the user.

According to some implementations of the present disclosure, a method includes receiving, via an electronic scale device supporting a user thereon, an indication to begin a verified weight sequence. Responsive to the indication to begin, the method includes: (1) determining a body weight of the user supported by the electronic scale device, (2) receiving, via an electronic device, image data that is reproducible as a visual image of at least a portion of the user supported on the housing of the scale, and (3) generating a data file including (a) weight data that is representative of the determined body weight of the user supported by the housing, (b) the image data, and (c) time data corresponding to a date and time that the body weight of the user was determined.

According to some implementations of the present disclosure, a method of conducting a verified weigh-in includes wirelessly registering an electronic device with the scale. The electronic device has a front-facing camera and a rear-facing camera. A user is detected on a scale. A body weight of the user on the scale is determined. The scale receives a unique indicium. The unique indicium is displayed, on a display device of the scale. The determined body weight of the user is displayed on the display device of the scale. The front-facing camera is caused to take a picture of at least a portion of a face of the user on the scale simultaneously with the rear-facing camera taking a picture of: (a) at least a portion of feet of the user on the scale, and (b) at least a portion of the display of the scale displaying the unique indicium and the determined body weight of the user.

According to some implementations of the present disclosure, a method of conducting a verified weigh-in includes wirelessly registering an electronic device with the scale. The electronic device has a front-facing camera and a rear-facing camera. A user is detected on a scale. A body weight of the user on the scale is determined. A unique indicium received by the scale from the electronic device is displayed on a display device of the scale. The front-facing camera is caused to take a picture of at least a portion of a face of the user on the scale simultaneously with the rear-facing camera taking a picture of: (a) at least a portion of feet of the user on the scale, and (b) at least a portion of the display of the scale displaying the unique indicium. Weight data representative of the determined body weight of the user on the scale is wireless transmitted to the electronic device for inclusion in a data file.

According to some implementations of the present disclosure, a method of conducting a verified weigh-in includes detecting a user on a scale. A body weight of the user on the scale is determined. The determined body weight of the user on the scale is displayed on a display device of the scale. A front-facing camera of an electronic device is caused to take a picture of at least a portion of a face of the user on the scale simultaneously with a rear-facing camera of the electronic device taking a picture of: (a) at least a portion of feet of the user on the scale and (b) at least a portion of the display of the scale displaying the determined body weight of the user.

According to some implementations of the present disclosure, a scale includes a housing, an electronic display, and an extendible member. The housing is configured to support a user thereon. The electronic display is coupled to the housing for displaying a body weight of the user. The extendible member is coupled to the housing and is movable between a collapsed-storage position and an extended-generally-upright position.

According to some implementations of the present disclosure, a scale for use with an electronic device to conduct verified weigh-ins includes a housing, an electronic display, a wireless communication module, one or more processors, a memory device, an extendible member, a coupling mechanism, and a pivotable-pin assembly. The housing is configured to support a user thereon. The electronic display is coupled to the housing for displaying a body weight of the user. The wireless communication module is configured to wirelessly communicate with the electronic device. The memory device stores instructions that, when executed by at least one of the one or more processors, cause the scale to determine the body weight of the user supported by the housing. The extendible member is coupled to the housing and is movable between a collapsed-storage position and an extended-generally-upright position. A central axis of the extendible member is generally horizontal in the collapsed-storage position and is at an angle between about 30 degrees and about 90 degrees relative to horizontal in the extended-generally-upright position. The coupling mechanism extends from a first end of the extendible member. The coupling mechanism is configured to releasably hold the electronic device in a generally fixed position relative to the housing. The pivotable-pin assembly is coupled to a second opposing end of the extendible member. The pivotable-pin assembly is slidable from a first end of a track to a second end of the track such that the extendible member can (i) slide relative to the housing and (ii) pivot relative to the housing. The extendible member is releasably maintained in the extended-generally-upright position by the pivotable-pin assembly engaging the second end of the track.

According to some implementations of the present disclosure, a scale includes a main housing and a movable housing. The main housing is configured to support a user thereon. The movable housing is coupled to the main housing via a pair of rods. The movable housing is movable between a first position adjacent to the main housing and a second position spaced from the main housing. The movable housing includes an electronic display for displaying a body weight of the user. The movable housing further includes a camera for generating image data that is reproducible as a visual image or a visual video clip of at least a portion of the user supported on the main housing of the scale. A lens of the camera is obscured by the main housing when the movable housing is in the first position and the lens of the camera is not obscured by the main housing when the movable housing is in the second position.

According to some implementations of the present disclosure, a scale system includes a main housing, a rotating housing, and a camera. The main housing includes an electronic display for displaying a body weight of the user. The rotating housing is coupled to the main housing via a drive system. The rotating housing is rotatable about the main housing. The camera is for generating image data that is reproducible as a visual image or a visual video clip of at least a portion of the user supported on the main housing of the scale.

According to some implementations of the present disclosure, a scale system includes a scale housing, an electronic display, and an extendible member. The scale housing is configured to support a user thereon. The electronic display is coupled to the scale housing for displaying a body weight of the user. The extendible member has a collapsed configuration and an extended configuration. The extendible member includes a coupling mechanism extending from a first end of the extendible member. The coupling mechanism is configured to releasably hold an electronic device in a generally fixed position relative to the scale housing. The extendible member includes a base-plate extending from a second opposing end of the extendible member. The base-plate is configured to be positioned under the scale housing when the user is supported on the scale housing.

According to some implementations of the present disclosure, a method includes receiving at a first time, via an electronic scale device supporting a user thereon, a first indication to begin a first verified weight sequence. Responsive to the first indication to begin the first verified weight sequence, the method includes: (1) determining a first body weight of the user supported by the electronic scale device, (2) receiving, via an electronic device, first image data that is reproducible as a first visual image of at least a portion of the user supported on the housing of the scale, and (3) analyzing the first image data using recognition software to produce a first user appearance profile. An expected user appearance profile is created based on at least the first user appearance profile. The method further includes receiving at a second time, via the electronic scale device supporting the user thereon, a second indication to begin a second verified weight sequence. Responsive to the second indication to begin the second verified weight sequence, the method includes: (1) determining a second body weight of the user supported by the electronic scale device, (2) receiving, via an electronic device, second image data that is reproducible as a second visual image of at least a portion of the user supported on the housing of the scale, (3) analyzing the second image data using recognition software to produce a second user appearance profile, and (4) comparing the second user appearance profile to the expected user appearance profile.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

FIG. 4A is a perspective view of a scale with a free-standing extendible member stored in a housing of the scale, according to some implementations of the present disclosure;

FIG. 4B is a perspective view of the scale of FIG. 4A illustrating the free-standing extendible member being removed from the scale, according to some implementations of the present disclosure;

FIG. 5B is a bottom perspective view of the scale of FIG. 5A with the movable housing in the retracted position;

FIG. 5D is a bottom perspective view of the scale of FIG. 5A with the movable housing in the extended position;

FIG. 6A is a top perspective view of a scale with a detachable housing attached to a main housing, according to some implementations of the present disclosure;

FIG. 6B is a top perspective view of the scale of FIG. 6A with the detachable housing detached from and spaced away from the main housing;

FIG. 7A is a perspective view of a scale with an extendible member stored in a housing of the scale in a collapsed-storage position, according to some implementations of the present disclosure;

FIG. 7B is a partial perspective view of the scale of FIG. 7A with the extendible member extending from the housing of the scale in a collapsed and generally horizontal position;

FIG. 7C is a partial perspective view of the scale of FIG. 7A with the extendible member of the scale in an extended-generally-upright position and a coupling mechanism holding a mobile electronic device;

FIG. 7D is a side view of the scale of FIG. 7A with the extendible member in the collapsed-storage position;

FIG. 7E is a side view of the scale of FIG. 7A with the extendible member extending from the housing of the scale in the collapsed and generally horizontal position;

FIG. 7F is a partial side view of the scale of FIG. 7A with the extendible member in a collapsed-generally-upright position and a pivotable-pin assembly of the extendible member in a first position;

FIG. 7G is a partial side view of the scale of FIG. 7A with the extendible member in the collapsed-generally-upright position and the pivotable-pin assembly of the extendible member in a second position;

FIG. 10C is a front view of a user interface at a third time during a verified weight sequence;

FIG. 10D is a front view of a user interface at a fourth time during a verified weight sequence;

FIG. 18 illustrates an indicium indicative of a verified biomeasurement of a subject displayed on a display of a mobile electronic device, according to some implementations of the present disclosure.

Figure 1:
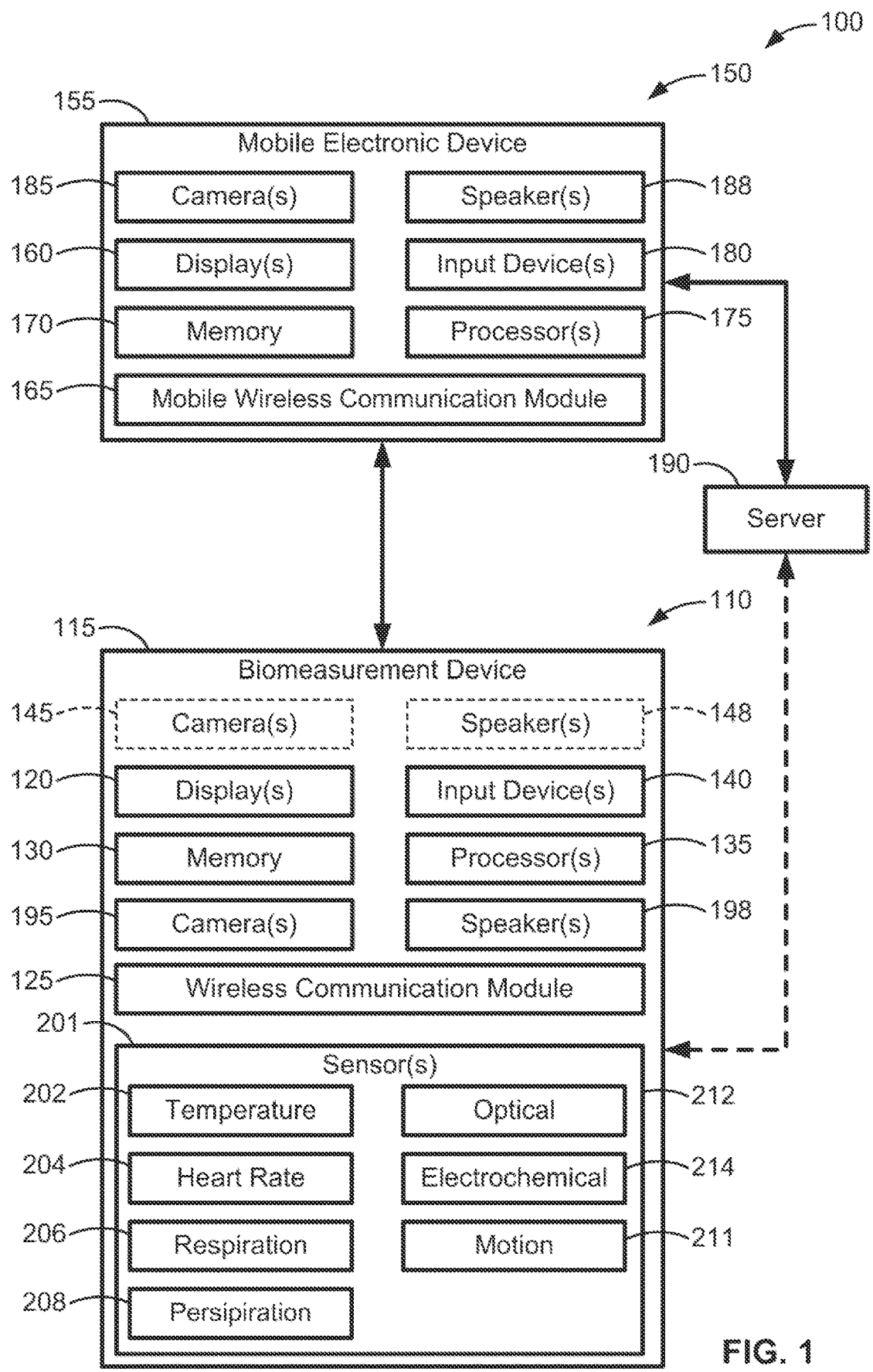
FIG. 1 is a schematic view of a system, according to some implementations of the present disclosure.

While the present disclosure is susceptible to various modifications and alternative forms, specific implementations have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

Referring to FIG. 1, a system 100 according to some implementations of the present disclosure is illustrated. The system 100 includes a biomeasurement device 110, a mobile electronic device 150, and a server 190.

The biomeasurement device 110 includes a housing 115 that can have any shape or size and be made of any material, such as, for example, plastic, metal (e.g., aluminum, steel, titanium), rubber, or any combination thereof. The housing 115 is coupled to an electronic display 120 that is viewable and able to display a variety of information. For example, the electronic display 120 can display a determined body or core temperature of a user of the system 100, a time and date of a temperature determination (i.e., the time that the biomeasurement device 110 determined the temperature of the user), preprogramed and/or received messages, instructions for conducting a biomeasurement session, instructions for using an application running on the mobile electronic device 150, instructions for operating the biomeasurement device 110, or any other type of information.

The housing 115 of the biomeasurement device 110 also includes therein a memory 130 and one or more processors 135. The memory 130 stores instructions that are executable by the one or more processors 135 to cause the biomeasurement device 110 to perform a multitude of functions. For example, execution of the instructions stored on the memory 130 cause the biomeasurement device 110 to determine a body temperature of a user. For another example, execution of the instructions stored on the memory 130 cause the biomeasurement device 110 to measure a heart rate of the user, a respiration rate of the user, a perspiration rate of the user, an activity level of the user, or any combination thereof. For yet another example, execution of the instructions stored on the memory 130 cause the biomeasurement device 110 to wirelessly transmit biomeasurement data representative of the determined biomeasurements of the user, via the wireless communication module 125, to the mobile electronic device 150 and/or the server 190.

The housing 115 of the biomeasurement device 110 also includes therein a wireless communication module 125 for establishing and/or communicating wirelessly with the mobile electronic device 150 and/or the server 190 (e.g., directly and/or indirectly via the mobile electronic device 150). The wireless communication module 125 can communicate using any type of wireless technology, such as, for example, Bluetooth, Bluetooth Low Energy (BLE), WiFi, Near Field Communication (NFC), ZigBee, Mesh Networking, Worldwide Interoperability for Microwave Access (WiMax), Radio Frequency (RF), Infrared (IR), etc., or any combination thereof. For example, in some implementations, the wireless communication module 125 establishes communication between the biomeasurement device 110 and the mobile electronic device 150 via BLE and establishes communication between the biomeasurement device 110 and the server 190 via WiFi.

For yet another example, execution of the instructions stored on the memory 130 cause the biomeasurement device 110 to wirelessly transmit instructions to the mobile electronic device 150. In some such implementations, the transmitted instructions direct the mobile electronic device 150 to generate image data that is reproducible as a visual image of the user using the biomeasurement device 110 at about the same time that the biomeasurement device 110 determines a biomeasurement (e.g., temperature of the user).

In some implementations, the biomeasurement device 110 includes one or more input devices 140. The input device 140 can be a touch screen, a softkey, a physical button, or any other type of input device that permits a user to select options displayed on the display device 120 and/or to initiate a verified biomeasurement sequence. Activation of the input device 140 by the user can (1) initiate a verified biomeasurement sequence, (2) cause the one or more processors 135 to cause the biomeasurement device 110 to determine the temperature of the user, (3) cause a camera 185 of the mobile electronic device 150 to take one or more pictures and/or videos of at least a portion of the user, (4) record time stamp information (e.g., a date and time that the verified biomeasurement sequence occurred), (5) generate a data file, (6) transmit a data file to the server 190, or any combination thereof.

In some such implementations, the input device 140 is a toe-push button that protrudes from a surface of the housing 115 of the biomeasurement device 110 such that the toe-push-button is readably accessible by the user to be manually activated. Activation of the toe-push-button by the user can (1) initiate a verified weigh-in sequence, (2) cause the one or more processors 135 to cause the biomeasurement device 110 to determine the body weight of the user supported by the housing 115, (3) cause a camera of the biomeasurement device 110 to take one or more pictures, (4) cause a camera 185 of the mobile electronic device 150 to take one or more pictures, (5) record time stamp information (e.g., a date and time that the verified weigh-in sequence occurred), (6) generate a data file, (7) transmit a data file to the server 190, or any combination thereof. The toe-push-button is sized and positioned relative to the housing 115 such that the toe-push-button is generally accessible by a toe of the user when standing on the housing 115. In some implementations, the toe-push-button has an exposed surface area between about 0.05 square inches and about 4.0 square inches. In some other implementations, the toe-push-button has an exposed surface area between about 0.25 square inches and about 1.0 square inch. In some other implementations, the toe-push-button has an exposed surface area of about 0.4 square inches.

In some implementations, the biomeasurement device 110 includes one or more cameras 145. The one or more cameras 145 can include standard cameras used to take color still images and/or color video, infrared cameras, thermal cameras, ultraviolet cameras, or a combination thereof. The one or more cameras 145 can be used to identify a user of the biomeasurement device 110 via facial recognition software operating on the biomeasurement device 110 or on any other device of the system 100. Additionally or alternatively the one or more cameras 145 can be used to generate image data for inclusion in a data file for use in verification of the user's identity and/or weigh-in as described herein. In some implementations, the image data is reproducible as a head-to-toe visual image of the user that includes at least a portion of the user's head and at least a portion of the user's feet (and everything in-between). In some alternative implementations, the image data is reproducible as a partial head-to-toe visual image of the user that does not include the user's head. In some other alternative implementations, the image data is reproducible as a visual image one or more portions of the user's body, such as, for example, the user's head, face, feet, mid-section/torso, legs, etc., or any combination thereof.

In some implementations, the biomeasurement device 110 includes one or more speakers 148 coupled to the housing 115. The one or more speakers 148 can play a variety of audio clips, such as, for example, music, audio instructions, audio taunts (e.g., in response to the wireless communication module 125 of the biomeasurement device 110 receiving a taunt signal), prerecorded audio messages, or any combination thereof.

In some implementations, the biomeasurement device 110 also includes one or more sensors 201. The one or more sensors 201 are generally used to generate or obtain one or more biomeasurements of a user of the biomeasurement device 110. The one or more sensors 201 include a temperature sensor 202, a heart rate sensor 204, a respiration sensor 206, a perspiration sensor 208, a motion sensor 211, an optical sensor 212, an electrochemical sensor 214, or any combination thereof.

The temperature sensor 202 generates temperature data indicative of a temperature of a user (e.g., a core temperature, a body temperature, a skin temperature, or any combination thereof) and/or an ambient temperature of the environment surrounding the user and/or biomeasurement device 110. The temperature sensor 202 can be, for example, an infrared sensor, a thermocouple sensor, a thermistor sensor, a silicon band gap temperature sensor or semiconductor-based sensor, a resistance temperature detector, a resistive temperature measuring device, a bimetallic device, a change-of-state sensor, a silicon diode, or any combination thereof. In some implementations, the temperature sensor 202 is a digital thermometer that directly contacts and is received by a portion of the user (e.g., under the tongue, in an ear, etc.) to record the temperature of the user. In other implementations, the temperature sensor 202 does not contact the user to record the temperature of the user (e.g., using an infrared beam). As described herein, the temperature data from the temperature sensor 202 can be used to determine whether the user has a fever that is indicative of an infection or illness.

The heart rate sensor 204 generates physiological data associated with the user that is indicative of a heart rate of the user. In some implementations, the heart rate sensor 204 is a photoplethysmogram (PPG) sensor. In other implementations, the heart rate sensor 204 is an electrocardiogram (ECG) sensor. As described herein, data from the heart rate sensor 204 can be used to determine whether the user is performing physical activity and/or whether the user is suffering from an infection or illness.

The respiration sensor 206 generates physiological data associated with the user that is indicative of a respiration rate of the user, an inspiration of the user, an expiration of the user, or any combination thereof. As described herein, data from the respiration sensor 206 can be used to determine whether the user is performing physical activity and/or whether the user is suffering from an infection or illness.

The perspiration sensor 208 generates physiological data associated with the user that is indicative of perspiration of the user. As described herein, data from the perspiration sensor 206 can be used to determine whether the user is performing physical activity and/or whether the user has a fever.

The motion sensor 211 generates motion data associated with the user that is indicative of movement of the user. The motion sensor 211 can include one or more accelerometers and/or one or more gyroscopes for generating the motion data. As described in further detail herein, the motion data from the motion sensor 211 can be used to determine whether the user is performing physical activity, whether the user is performing a biomeasurement using the biomeasurement device 110, whether the user is complying with instructions for performing a biomeasurement with the biomeasurement device 110, or any combination thereof. The motion data from the motion sensor 211 can also be used, for example, determine whether the user is coughing or sneezing.

The optical sensor 212 and electrochemical sensor 214 can be used to determine data associated with blood of the user. For example, the optical sensor 212 and/or electrochemical sensor 214 can be used to determine a white blood cell count of the user, which can be indicative of whether the user is suffering from an infection or illness. In some implementations, the one or more sensors 201 also include an oxygen sensor, a pulse oximeter sensor, an analyte sensor, a moisture sensor, or any combination thereof.

In some implementations, the one or more sensors 201 includes an acoustic sensor (e.g., including a microphone) that detects sounds associated with the user and/or the user environment. In such implementations, data from the acoustic sensor can be analyzed to determine whether user is coughing or sneezing. The acoustic sensor can also be used to detect respiration of the user (e.g., labored breathing).

In some implementations, the one or more sensors 201 include a terahertz (THz) sensor (e.g., for generating image data). The terahertz spectrum generally refers to the portion of the electromagnetic spectrum between about 100 GHz and about 10 THz, or wavelengths of about 3 mm to about 30 μm. The relatively long THz wavelengths can penetrate further into biological tissue than visible or near infrared light. Because THz radiation excites rotational and vibrational modes of some biological molecules, THz radiation provides effective tissue-differentiating properties based on differences in optical reflection due to water content. The terahertz sensor can be used, for example, to image and/or analyze tissue (e.g., from a human being) to diagnose one or more medical conditions. Unlike x-ray radiation, terahertz wavelengths are generally considered safe for use on human beings. Terahertz wavelength radiation can also penetrate some substances or materials (e.g., concrete, wood, plastic, etc.) that are opaque to visible light, allowing these materials to be imaged. The terahertz sensor can be used (e.g., in lieu of or addition to image data from a camera) to verify an identity of a subject, obtain a biomeasurement of a subject, verify a biomeasurement of the subject, or any combination thereof.

In some implementations, the one or more sensors 201 include a breathalyzer sensor. The breathalyzer sensor can be used, for example, to determine a blood alcohol content (BAC) of a subject. In some implementations, the breathalyzer sensor or the like can be used to collect a sample of air expelled from a subject to later analyze. In some such implementations, the sample of air can be analyzed to determine if the subject was and/or is infected with one or more viruses (e.g., Coronavirus). The systems and methods described herein can be used with the breathalyzer sensor to verify an identity of a subject, obtain a biomeasurement of the subject (e.g., BAC), and verify the biomeasurement of the subject (in this example, a BAC), or any combination thereof.

While the one or more sensors 201 are shown and described as including each of the temperature sensor 202, the heart rate sensor 204, the respiration sensor 206, the perspiration sensor 208, the motion sensor 211, the optical sensor 212, and the electrochemical sensor 214, more generally, the one or more sensors 201 can include any combination and any number of each of the sensors described and/or shown herein.

In some implementations, the one or more sensors 201 of the biomeasurement device 110 are coupled to or integrated in the housing 155 of the mobile electronic device 150. In such implementations, the system 100 does not include a separate and distinct housing 115 for the biomeasurement device 110. Further, in such implementations, the display 160, memory 170, and processor 175 of the mobile electronic device 150 can perform the functions of the display 120, the memory 130, and the processor 135 of the biomeasurement device 110 described herein. In such implementations, the processor 175 of the mobile electronic device 150 and/or the processor 135 of the biomeasurement device 110 can be referred to as a control system.

In some implementations, the biomeasurement device 110 can be used determine information indicative of body fat (e.g., a percentage) of the user. For example, the biomeasurement device 110 can be a scale, skin fold calipers, a body circumference measuring device, a dual-energy x-ray absorptiometry device, a hydrostatic weighing device, an air displacement plethysmography device (bod pod), a bioelectrical impedance analysis (BIA) device, an electrical impedance myography (EIM) device, a three-dimensional body scanning device, a multiple-compartment model device, etc.

The mobile electronic device 150 can be, for example, a cellphone (e.g., a smart phone, an iPhone® smart phone, an Android® smart phone, etc.), a tablet computer (e.g., an iPad®), a camera (e.g., a wireless or smart camera), a Bluetooth-enabled device, or the like. The mobile electronic device 150 includes a housing 155 that can have any shape or size and be made of any material, such as, for example, plastic, metal (e.g., aluminum, steel, titanium), rubber, or any combination thereof. In some implementations, the biomeasurement device 110 is a wearable device (e.g., a smartwatch, a bracelet, etc.) that can be communicatively coupled to the mobile electronic device 150. In other implementations, the biomeasurement device 110 is a stethoscope, a spirometer, a medical alert system or device, an EKO stethoscope, a diabetes injection pen, a blood glucose monitor, a drug inhaler, or a scale.

The housing 155 of the mobile electronic device 150 is coupled to a mobile electronic display 160 that is viewable and able to display a variety of information. For example, the mobile electronic display 160 can display an application or app running on the mobile electronic device 150, one or more pictures of the user of the system 100, a time and date that the one or more pictures were taken by one or more cameras 185 of the mobile electronic device 150, a time and date of a biomeasurement (i.e., the time that the biomeasurement device 110 determined one or more biomeasurements of the user), preprogramed and/or received messages, instructions for performing a biomeasurement, instructions for using the application running on the mobile electronic device 150, instructions for operating the biomeasurement device 110, or any other type of information.

The housing 155 of the mobile electronic device 150 also includes therein a mobile wireless communication module 165 for establishing and/or communicating wirelessly with the biomeasurement device 110 and/or the server 190 (e.g., directly and/or indirectly). The wireless communication module 165 can communicate using any type of wireless technology, such as, for example, Bluetooth, Bluetooth Low Energy (BLE), WiFi, Near Field Communication (NFC), ZigBee, Mesh Networking, Worldwide Interoperability for Microwave Access (WiMax), Radio Frequency (RF), Infrared (IR), etc., or any combination thereof. For example, in some implementations, the wireless communication module 165 establishes communication between the mobile electronic device 150 and the biomeasurement device 110 via BLE and establishes communication between the mobile electronic device 150 and the server 190 via WiFi. For another example, in some implementations, the wireless communication module 165 establishes communication between the mobile electronic device 150 and the biomeasurement device 110 via WiFi and establishes communication between the mobile electronic device 150 and the server 190 via WiFi.

The housing 155 of the mobile electronic device 150 also includes therein a memory 170 and one or more processors 175. The memory 170 stores instructions that are executable by the one or more processors 175 to cause the mobile electronic device 150 to perform a multitude of functions. For example, execution of the instructions stored on the memory 170 cause the mobile electronic device 150 to: (1) wirelessly transmit, via the mobile wireless communication module 165, a data file to the server 190, (2) wirelessly transmit, via the mobile wireless communication module 165 image data to the server 190, (3) verify an identify of a user of the biomeasurement device 110, (4) verify a biomeasurement taken by the biomeasurement device 110, etc., or any combination thereof.

The mobile electronic device 150 further includes one or more input devices 180. The input devices 180 can be a touch screen, a softkey on a touch screen, a physical button (e.g., a home button, a volume button, a power button, a shutter button, etc.), a joystick, or any other type of input device that permits a user to: (1) initiate a verified biomeasurement sequence, (2) select options displayed on the display device 160, (3) operate the mobile electronic device, (4) transmit a data file to the server 190 for verification of a biomeasurement, etc., or any combination thereof.

The mobile electronic device 150 includes one or more cameras 185. The one or more cameras 185 can include standard cameras used to take color still images and/or color video, infrared cameras, thermal cameras, ultraviolet cameras, or a combination thereof. The one or more cameras 185 can be used to identify a user of the mobile electronic device 150 and/or of the biomeasurement device 110 via facial recognition software operating on the mobile electronic device 150. Additionally or alternatively the one or more cameras 185 can be used to generate image data (e.g., one or more pictures) for inclusion in a data file for use in verification of the user's identify and/or biomeasurement as described herein. In some implementations, the image data is reproducible as a head-to-toe visual image of the user that includes at least a portion of the user's head and at least a portion of the user's feet (and everything in-between). In some alternative implementations, the image data is reproducible as a partial head-to-toe visual image of the user that does not include the user's head. In some other alternative implementations, the image data is reproducible as a visual image one or more portions of the user's body, such as, for example, the user's head, face, feet, mid-section/torso, legs, etc., or any combination thereof.

In some implementations, the mobile electronic device 150 includes a front-facing camera and a rear-facing camera. In some of such implementations, the front-facing camera is caused to (e.g., after initiation of a verified biomeasurement sequence) take a picture of at least a portion of a face of the user when using the biomeasurement device 110 and/or at least a portion of the display 120 of the biomeasurement device 110 displaying information, such as, for example, a unique indicium, a symbol, an alphanumeric code, a word, a number, a determined temperature of the user, a time, a date, a message, instructions, etc., or any combination thereof.

The mobile electronic device 150 includes one or more speakers 188 coupled to the housing 155. The one or more speakers 188 can play a variety of audio clips, such as, for example, music, audio instructions (e.g., instructions on how to conduct a verified biomeasurement, instructions on how to use the system 100, etc.), prerecorded audio messages, or any combination thereof.

The server 190 can be local (e.g., in the same house or building as the biomeasurement device 110 and the mobile electronic device 150) or remote (e.g., in a different building, in a different state, in a different country). The server 190 is communicatively coupled (e.g., over the internet, over one or more wired and/or wireless networks, etc.) to the biomeasurement device 110 and/or the mobile electronic device 150 to receive data files for evaluation. The data files can include a variety of information used to verify one or more biomeasurements taken by the biomeasurement device 110. In some implementations, the data files include biomeasurement data (e.g., data that is indicative of one or more biomeasurements of a user), image data (e.g., image data that is reproducible as a visual image or visual video image of a user), and time data (e.g., data corresponding to a date and time that a biomeasurement of a user was determined and/or data corresponding to a date and time that one or more pictures or videos of a user were captured). The verification functions of the server 190 are performed using one or more software programs running on (e.g., executing on) the server 190 that automatically analyze the data files and make determinations thereof (e.g., determinations of identity, cheating, accurate weight ins, etc.) for use in policing and/or conducting weight loss competitions.

Alternatively, instead of including a server 190, the verification functions described herein can be conducted on or performed by the mobile electronic device 150 (e.g., the processor 175 of the mobile electronic device 150). In some such alternative implementations, a verification result (e.g., a data file including information related to a determination as to whether the user's identify was verified, a determination as to whether the user's biomeasurement was verified, a determination as to whether the user was cheating, etc., or any combination thereof) can be transmitted from the biomeasurement device 110 and/or from the mobile electronic device 150 to the server 190 and/or a different server (not shown) for review and/or storage.

In some implementations, a user profile associated with a user of the system 100 is stored in the memory 130 of the biomeasurement device 110, the memory 170 of the mobile electronic device 150, a memory of the server 190, or any combination thereof. The user profile can include demographic information associated with the user, such as, for example, an age of the user and a sex of the user. The user profile can also include medical information associated with the user, such as, for example, information indicative of one or more medical conditions associated with the user, information indicative of a family history of medical conditions associated with the user, information indicative of the user having been vaccinated for a disease, information indicative of the user having been tested for a disease, information indicative of the user having been diagnosed with a disease, information indicative of the user having recovered from the disease, information indicative of the user having antibodies associated with a disease, information indicative of the user having been in contact with one or more persons having been diagnosed with a disease, or any combination thereof. The disease can be an infectious disease, such as, for example, the novel coronavirus of 2019 (COVID-19). The user profile can also include previously recorded biomeasurements of the user (e.g., that were taken using the biomeasurement device 110).

The system 100 can present results to the user in an easily accessible manner. The system 100 can organize the data into charts or graphs, and can provide guides or tips to the user based on the recorded data. The system 100 can also measure and monitor muscle mass and strength, for example to monitor arm muscle growth, chest muscle growth, or back muscle growth. The scale can measure strength of different parts of the body.

The system 100 may also include a lock feature that locks a video once it has been submitted. A locked video is secured such that it cannot thereafter be altered or deleted. An indication that a submitted video is locked may appear to users. The user that uploaded the video may be able to "unlock" the video to edit or delete the video, allowing for a new weigh-in video to be submitted. Videos can also be pre-verified. For example, a user's weigh-in may be monitored by a healthcare professional or a representative of the weight loss contest operator to ensure the proper procedure is followed. Monitored biomeasurements can also be scheduled for random or specified times. Once submitted, pre-verified biomeasurements may include a badge or other indication that the biomeasurements has been pre-verified. This ensures to users that both their own submissions and submissions by other users cannot be tampered with or altered in any way. The uploading of videos and accessing of uploaded videos may be tracked by the user's IP Address, Internet Service Provider, and log-in. A user can generate a unique password from their account to allow third parties to view submissions.

A method of conducting a verified weigh-in using the system 100 is now described. The verified weigh-in begins when the system 100 receives an indication to begin a verified weight sequence. The indication can be caused by (1) a user stepping onto the biomeasurement device 110, (2) a user activating the toe-push-button 140, (3) a user activating one of the input devices 180 of the mobile electronic device 150, or any combination thereof. After the initiation of the verified weigh-in, the biomeasurement device 110 determines a body weight of the user standing on the housing 115. At about the same time or at exactly the same time that the biomeasurement device 110 determines a body weight, image data is generated and/or received that is reproducible as one or more visual images and/or one or more visual videos of at least a portion of the user standing on the housing 115 of the biomeasurement device 110. The image data can be generated by the camera 145 of the biomeasurement device 110 and/or by the camera 185 of the mobile electronic device 150. In some alternative implementations, the image data is generated and/or received within five second of the time that the body weight is determined by the biomeasurement device 110. In yet some other alternative implementations, the image data is generated and/or received within four, three, two, one, or less seconds of the time that the body weight is determined by the biomeasurement device 110. By generating the image data (e.g., taking a picture and/or video) at the exact same time or about the same time that the body weight is determined, the ability for a contestant to cheat is reduced and/or eliminated.

In some implementations, the body weight and/or the image data is determined multiple times during a single weigh-in. For example, the user first stands on the biomeasurement device 110 facing a first direction and then the user stands on the biomeasurement device 110 facing another direction. As such, the weight verification system 100 is able to capture multiple angles (e.g., a front facing angle and a rear facing angle) of the user/contestant during the weigh-in.

In some implementations, a data file is generated that includes (a) weight data that is representative of the determined body weight of the user standing on the housing 115 of the biomeasurement device 110, (b) the image data, and (c) time data corresponding to a date and time that the body weight of the user was determined and/or corresponding to a date and time that the image data was generated and/or received/transmitted. The data file can be generated by the biomeasurement device 110, the mobile electronic device 150, the server 190, or a combination thereof.

In some implementations, the generated data file is transmitted. For example, if the mobile electronic device 150 generates the data file, the mobile electronic device 150 transmits the data file to the server 190 and/or the biomeasurement device 110 for further processing and/or evaluation (e.g., conducting a verification function). Alternatively, if the biomeasurement device 110 generates the data file, the biomeasurement device 110 transmits the data file to the server 190 and/or to the mobile electronic device 150 for further processing and/or evaluation (e.g., conducting a verification function). In some implementations, prior to the data file being transmitted, the user is prompted to review the contents of the data file, or a portion thereof (e.g., the picture(s) of the user), and accept or reject the verified weigh-in. If the verified weigh-in is accepted by the user, then the data is automatically transmitted; however, if the verified weigh-in is rejected by the user, then the data is not transmitted and the user is prompted to conduct a second verified weigh-in sequence. The prompting can be displayed on the display devices and/or played on the speakers of the biomeasurement device 110, of the mobile electronic device 150, or a combination thereof.

The data file is analyzed to conduct verification functions. For example, the image data in the data file can be analyzed using facial recognition software to verify the identity of the user. For another example, the image data in the data file can be analyzed using weight verification software to verify the determined body weight of the user. In some such implementations, the weight verification software compares one or more aspects of the image data (e.g., picture of the user) and/or the determined body weight with one or more corresponding aspects of other (e.g., older) data files associated with the user to determine if the newly/recently determined body weight is accurate or indicates potential cheating or unsafe weight loss practices. In some implementations, the weight verification software compares an outline of the user's body as depicted in the image data with one or more previous outlines of the user's body (as depicted in previously taken pictures of the user using the weight verification system 100) to verify the weigh-in (e.g., determine cheating, unsafe practices, etc.).

Figure 2:
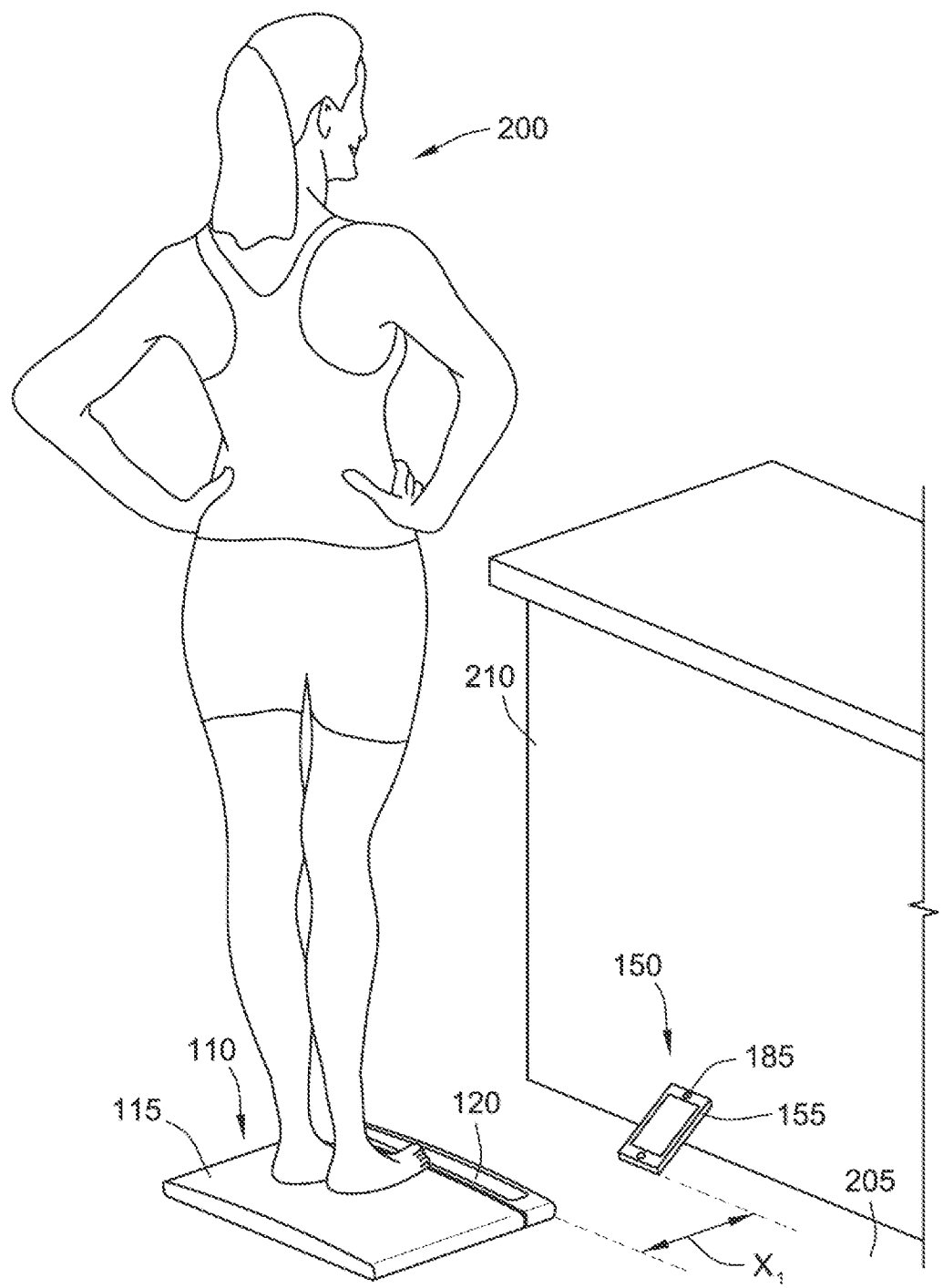
FIG. 2 is a perspective view of a user conducting a verified weigh-in using a weight verification system, according to some implementations of the present disclosure.

Now referring to FIG. 2, a weight loss competition contestant or user 200 is shown conducting a verified weigh-in using the weight verification system 100. As shown, the user 200 is standing on the biomeasurement device 110 with the housing 115 supporting the weight of the user 200 thereon. The mobile electronic device 150 is resting on a floor 205 (also supporting the biomeasurement device 110) and leaning on a cabinet or wall 210 such that the front-facing camera 185 is generally aimed at the user 200 to capture a head-to-toe visual image and/or video of the user 200 during a verified weigh-in sequence. The server 190 is not shown as in this implementation the server 190 is offsite. The mobile electronic device 150 is shown as being placed a distance $X_1$ from the biomeasurement device 110. The distance $X_1$ is between about six inches and about fifteen feet. Alternatively, the distance $X_1$ is between about two feet and eight feet. In some implementations, the distance $X_1$ is about six feet. The distance $X_1$ can be any number such that the front-facing camera 185 is able to capture the desired portion(s) of the user 200 (e.g., head-to-toe pictures, lower body only pictures, upper body only pictures, etc., or any combination thereof).

Figure 3:
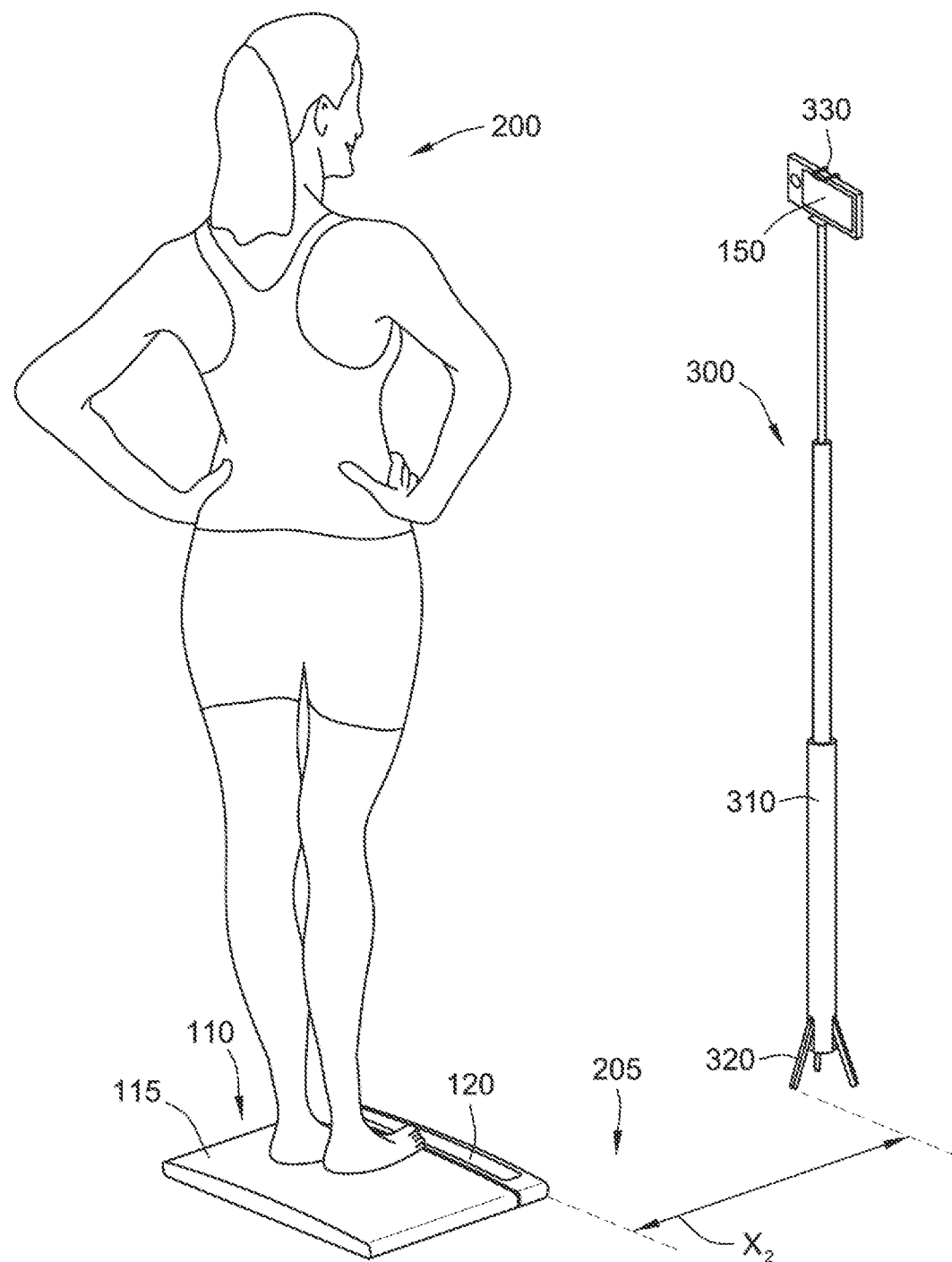
FIG. 3 is a perspective view of a user conducting a verified weigh-in using a weight verification system with a free-standing extendible member, according to some implementations of the present disclosure.

Now referring to FIG. 3, the weight loss competition contestant or user 200 is shown conducting a verified weigh-in using the weight verification system 100 and a free-standing extendible member 300. The free-standing extendible member 300 (e.g., a tripod stand, a selfie-stick, or the like) includes a telescoping body 310, feet 320, and a coupling mechanism 330. The telescoping body 310 is able to extend from a collapsed-storage configuration (not shown) to a second extended configuration (shown in FIG. 3). The telescoping body 310 is adjustable to adjust the height of the free-standing extendible member 300 during its use. The feet 320 extend from the telescoping body 310 to provide support for the telescoping body 310 to remain substantially upright when placed on the floor 205. The coupling mechanism 330 is a universal coupling mechanism that is adjustable to securely hold therein, in a releasable fashion, a variety of sizes, types, makes, models, etc. of the mobile electronic device 150. The mobile electronic device 150 is shown as being placed a distance $X_2$ from the biomeasurement device 110. The distance $X_2$ is between about six inches and about fifteen feet. Alternatively, the distance $X_2$ is between about two feet and eight feet. In some implementations, the distance $X_2$ is about six feet. The distance $X_2$ can be any number such that the front-facing camera 185 (or the rear-facing camera 185, not shown in FIG. 3) is able to capture the desired portion(s) of the user 200 (e.g., head-to-toe pictures, lower body only pictures, upper body only pictures, etc., or any combination thereof). While the telescoping body 310 is shown as having a generally circular cross-section, the telescoping body 310 can alternatively have a cross-section that is generally square, generally rectangular, generally triangular, generally oval, generally polygonal, or any combination thereof.

Now referring to FIGS. 4A and 4B, an alternative implementation of the biomeasurement device 110 is shown where the housing 115 includes a cavity 400 therein that is sized and shaped to store the free-standing extendible member 300 in its collapsed-storage configuration. As shown, in the collapsed-storage configuration, the feet 320 are retracted from their extended position (FIG. 3) to further compact the free-standing extendible member 300 for storage.

Now referring to FIGS. 5A-5D, an alternative implementation of the biomeasurement device 110 is shown as biomeasurement device 510 for use by itself and/or within the weight verification system 100 as described herein. The biomeasurement device 510 includes a main housing 515a and a movable housing 515b coupled to the main housing 515a via a pair of rods 518 (shown in FIGS. 5C and 5D). The rods 518 permit the movable housing 515b to move between a first retracted position (FIGS. 5A and 5B) and a second extended position (FIGS. 5C and 5D) by sliding/rolling relative to the main housing 515a. The movable housing 515b includes a pair of rollers/wheels 519 that aid in the movable housing 515b moving between the retracted and extended positions. The rods 518 are shown as having a generally cylindrical shape with a generally circular cross-section; however, the rods 518 can have any type of cross-sectional shape, such as, for example, square, rectangular, triangular, polygonal, etc., or any combination thereof. While two rods 518 are shown, the biomeasurement device 510 can have any number of rods 518 coupling the main and movable housings 515a,b (e.g., one rod, three rods, four rods, etc.).

Figure 5A:
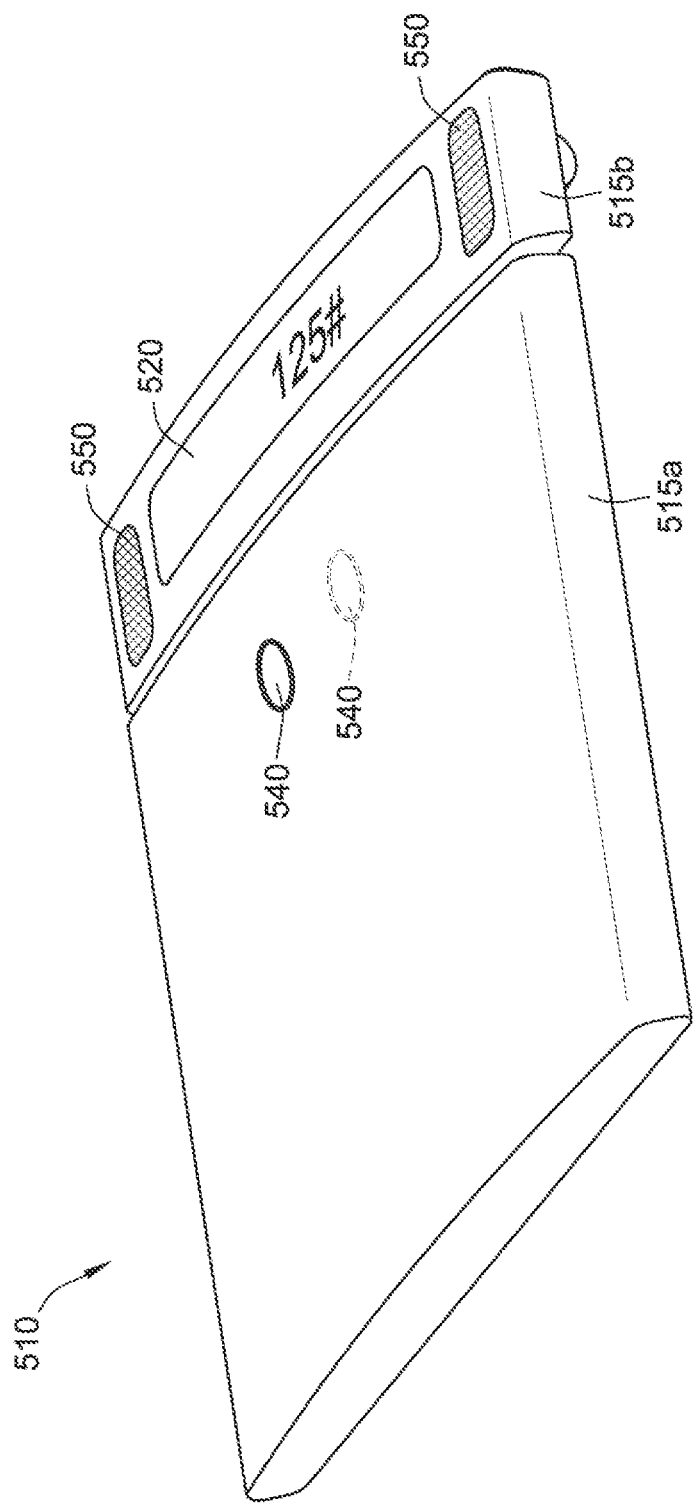
FIG. 5A is a top perspective view of a scale with a movable housing in a retracted position, according to some implementations of the present disclosure.
Figure 5C:
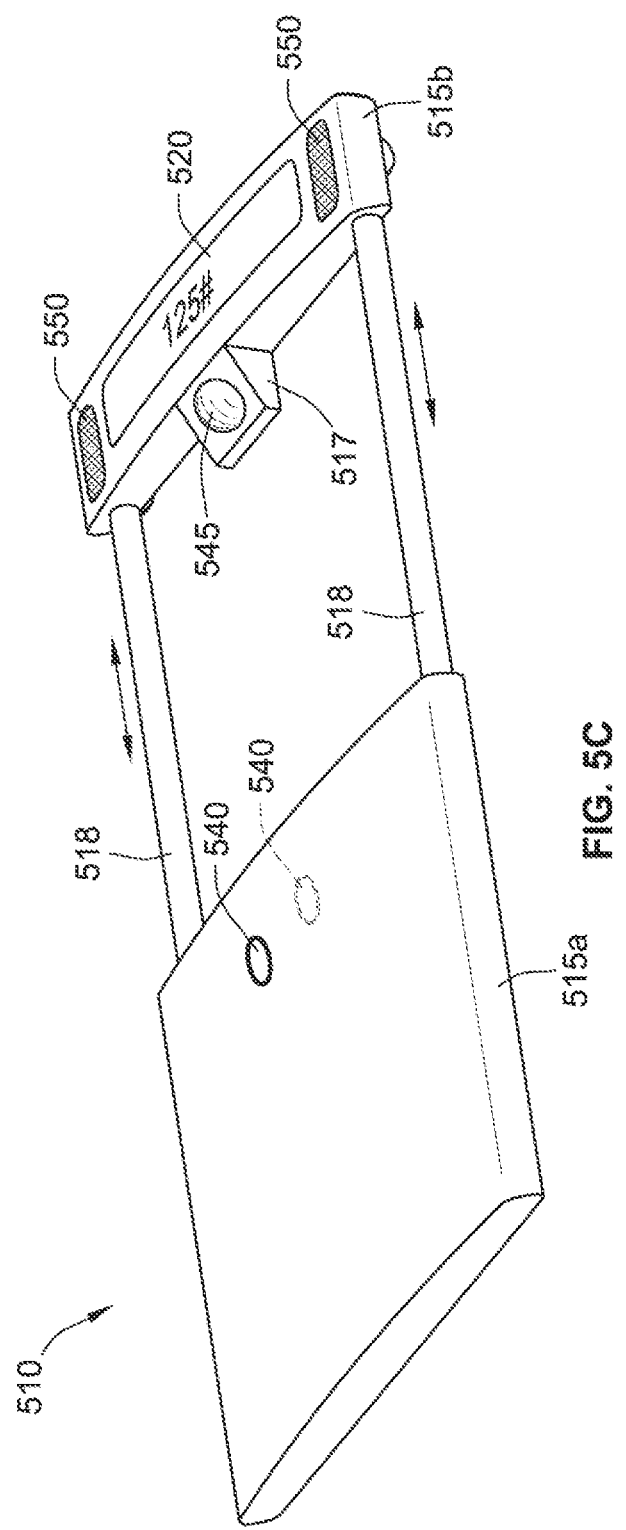
FIG. 5C is a top perspective view of the scale of FIG. 5A with the movable housing in an extended position.

The main and movable housings 515a,b can each have any shape or size and be made of any material, such as, for example, plastic, metal (e.g., aluminum, steel, titanium), rubber, or any combination thereof. As best shown in FIG. 5D, the main housing 515a includes a cutout/undercut or slot 516 that receives a protrusion 517 of the movable housing 515b therein when the movable housing 515b is in the first retracted position (FIGS. 5A and 5B). The protrusion 517 can also be referred to as a camera housing as the protrusion 517 includes at least a portion of a camera 545 therein (e.g., at least a lens of the camera 545 is included in and/or mounted to the protrusion 517). The camera 545 can be the same as, or similar to, the various cameras described herein. As shown, the camera 545 includes a fisheye lens for taking wide-angle pictures (e.g., the camera 545 is able to generate image data that is reproducible as a visual image and/or a visual video clip of at least a portion of a user supported on the main housing 515a of the biomeasurement device 510), which can aid in capturing a relatively wider shot/picture as compared to a camera that does not have a fisheye lens (e.g., from the same distance from the object being captured in the picture). By positioning the camera 545 on/in the protrusion 517, the user of the biomeasurement device 510 can selectively and physically cover/obscure the lens of the camera 545. Such a feature is especially advantageous when the biomeasurement device 510 is placed in a bathroom as this obscuring feature can provide added comfort and peace of mind to the user that the lens of the camera 545 is not able to capture images of the user when not intended.

Similar to the biomeasurement device 110, the biomeasurement device 510 includes an electronic display 520 that is viewable and able to display a variety of information (e.g., the same information described herein). As shown, the electronic display 520 is coupled to the movable housing 515b; however, the electronic display 520 can alternatively be coupled to the main housing 515a. Additionally, two electronic displays 520 (not shown) can be included in the biomeasurement device 510 such that one is coupled to the main housing 515a and the other is coupled to the movable housing 515b.

To aid in the main housing 515a remaining stationary when the movable housing 515b is moved into the extended position, the main housing 515a can include a number of feet 528. The feet 528 can be rubber, plastic, metal, or any combination thereof. The feet 528 protrude a distance from a bottom surface of the main housing 515a that is the same as, or very close to, the distance that the roller/wheels 519 protrude from the bottom surface of the movable housing 515b. Alternatively, the roller/wheels 519 protrude from the bottom surface of the movable housing 515b more or less (e.g., +/−0.01 inches, +/−0.05 inches, +/−0.1 inches, +/−0.2 inches, +/−0.25 inches, etc.) than the feet 528 protrude from the bottom surface of the main housing 515a.

The biomeasurement device 510 includes one or more toe-push buttons as input device(s) 540 of the biomeasurement device 510. As shown, the toe-push-buttons 540 are relatively flush with (e.g., not recessed and not protruding from) an upper surface of the main housing 515a of the biomeasurement device 510. Alternatively, the toe-push-buttons 540 can be recessed in or protruding from the upper surface of the main housing 515a of the biomeasurement device 510. Generally, the toe-push-buttons 540 can be positioned in any fashion relative to the main housing 515a as long as the toe-push-button(s) 540 are readable accessible by the user of the biomeasurement device 510 (e.g., using a toe or portion of a foot/feet) to be manually activated in the same, or similar, manner as the input device 140 described herein. As shown, two toe-push-buttons 540 are positioned side-by-side and spaced apart a distance (e.g., 0.5 inches, 1.0 inches, 1.5 inches, 2 inches, etc.) such that a first one of the toe-push-buttons 540 is generally positioned to be activated by a first toe (e.g., big toe) of a left foot of a user and a second one of the toe-push-buttons 540 is generally positioned to be activated by a first toe (e.g., big toe) of a right foot of the user at the same time or about the same time.

The movable housing 515b includes a pair of gripper 550 positioned adjacent to the left and right ends of the movable housing 515b. The grippers 550 can be used to aid a user in moving the movable housing 515b between the retracted and extended positions. The grippers 550 can be rubber, plastic, metal, or any combination thereof. The grippers 550 can have a surface pattern increases surface friction when engaged by the user to move the movable housing 515b between the retracted and extended positions.

While not shown in FIGS. 5A-5D, the biomeasurement device 510 includes the same, or similar, components contained in the biomeasurement device 110, such as, for example, a wireless communication module, a memory device storing instructions, one or more processors, one or more speakers, etc., or any combination thereof.

While the rods 518 are shown as being generally straight (e.g., having a linear central axis), the rods 518 can have a variety of other shapes. For example, in an alternative implementation, each of the pair of rods 518 is generally curved (e.g., C-shaped or the like) such that moving the movable housing 515b from the retracted position to the extended position causes the movable housing 515b to not only extend from the main housing 515a, but to also move vertically relative to the main housing 515a (e.g., the movable housing 515b move off of the floor holding the biomeasurement device 510). In some such implementations, the curved rods (not shown) aid in providing a different angle for the camera 545 to capture pictures/videos/image data of the user on the main housing 515a.

Figure 6C:
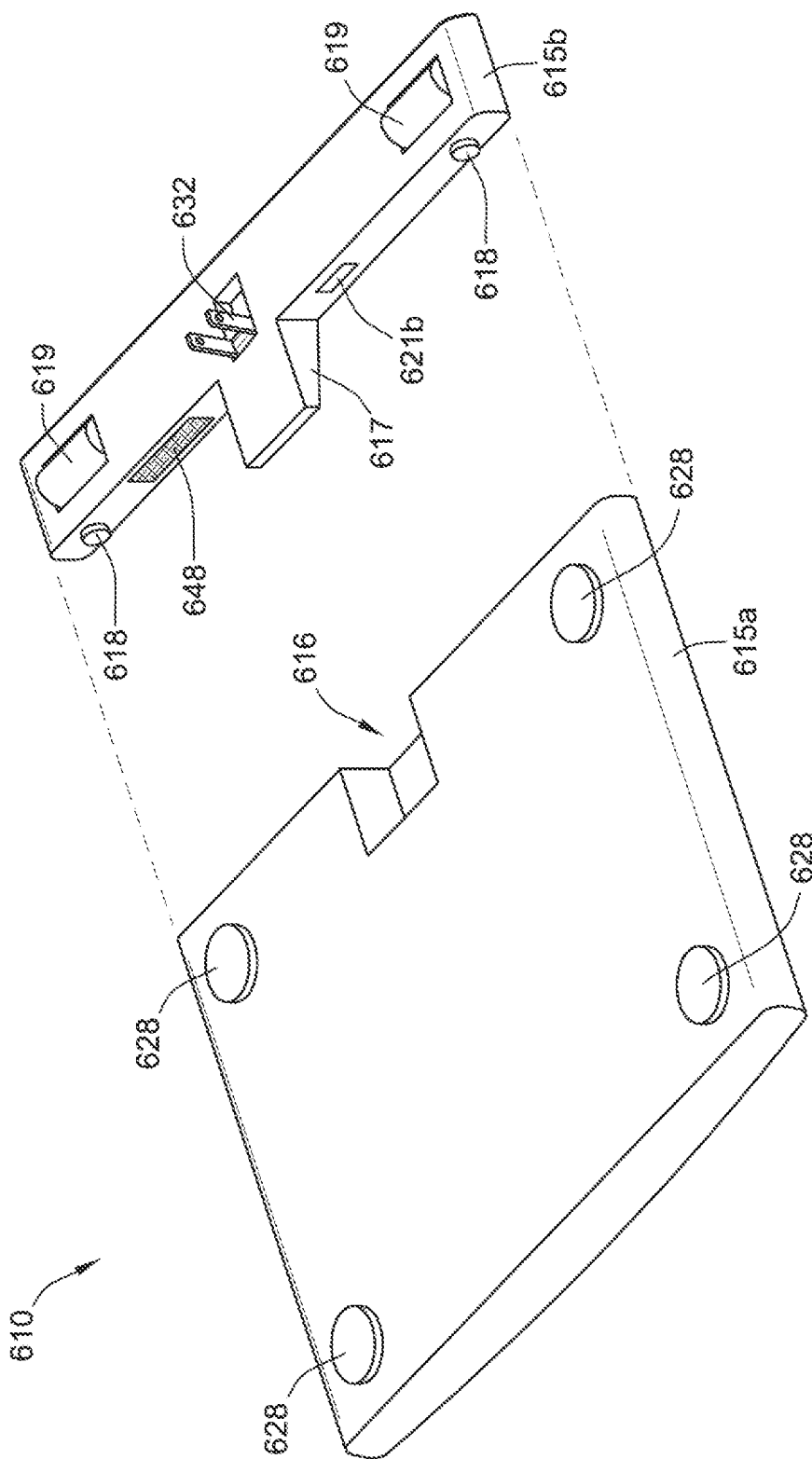
FIG. 6C is a bottom perspective view of the scale of FIG. 6B with the detachable housing detached from and spaced away from the main housing.

Now referring to FIGS. 6A-6C, an alternative biomeasurement device 610 is shown for use by itself and/or within the weight verification system 100 as described herein. The biomeasurement device 610 is similar to the biomeasurement device 510 but mainly differs in that the biomeasurement device 610 does not include the rods 518. The biomeasurement device 610 includes a main housing 615a and a detachable housing 615b. Because the detachable housing 615b is not coupled to the main housing 615a via rods, the detachable housing 615b has relatively more freedom (as compared with the movable housing 515b) for its placement when conducting a verified weigh-in and taking pictures of the user on the main housing 615a.

The detachable housing 615b can be removably coupled to the main housing 615a via a coupling mechanism 618 (e.g., a magnetic latch or the like). The detachable housing 615b includes a pair of rollers/wheels 619 that aid in the detachable housing 615b moving or rolling along the floor (e.g., bathroom floor) supporting the biomeasurement device 610 thereon.

The main and detachable housings 615a,b can each have any shape or size and be made of any material, such as, for example, plastic, metal (e.g., aluminum, steel, titanium), rubber, or any combination thereof. As best shown in FIG. 6C, the main housing 615a includes a cutout/undercut or slot 616 that receives a protrusion 617 of the detachable housing 615b therein when the detachable housing 615b is coupled to the main housing 615a via the coupling mechanism 618 (FIG. 6A). The protrusion 617 is the same as, or similar to, the protrusion 517 and includes at least a portion of a camera 645 therein (which is the same as, or similar to, the camera 545).

Similar to the biomeasurement device 110, the biomeasurement device 610 includes an electronic display 620 that is viewable and able to display a variety of information (e.g., the same information described herein). As shown, the electronic display 620 is coupled to the detachable housing 615b; however, the electronic display 620 can alternatively be coupled to the main housing 615a. Additionally, two electronic displays 620 (not shown) can be included in the biomeasurement device 610 such that one is coupled to the main housing 615a and the other is coupled to the detachable housing 615b.

To aid in the main housing 615a remaining stationary when the detachable housing 615b is detached from and/or moved away from (e.g., spaced from) the main housing 615a, the main housing 615a can include a number of feet 628 that are the same as, or similar to, the feet 528. The detachable housing 615b includes a pair of gripper 650 that are the same as, or similar to, the grippers 550. The biomeasurement device 610 can also include one or more speakers 648 that are the same as, or similar to, the speakers 148 described herein. While not shown in FIGS. 6A-6C, the biomeasurement device 610 includes the same, or similar, components contained in the biomeasurement device 110, such as, for example, a wireless communication module, a memory device storing instructions, and one or more processors, etc., or any combination thereof.

The biomeasurement device 610 includes an electrical plug 632 for plugging the detachable housing 615b directly into an electrical outlet or the like for charging a power source (e.g., rechargeable battery) (not shown) contained within the detachable housing 615b. The power source can be used to power any of the electronic components (e.g., processor, memory, display, etc.) of the biomeasurement device 610, whether the components are contained within the detachable housing 615b and/or in the main housing 615a. As shown, the main and detachable housings 615a,b include electrical power couplers 621a,b that electrically couple the main and detachable housings 615a,b together when the detachable housing 615b is coupled with the main housing 615a via the coupling mechanism 618. The electrical power couplers 621a,b permit power to be transferred from the power source in the detachable housing 615b to a second power source (e.g., rechargeable battery) (not shown) in the main housing 615a.

Now referring to FIGS. 7A-7G, an alternative biomeasurement device 710 is shown for use by itself and/or within the weight verification system 100 as described herein. The biomeasurement device 710 is similar to the biomeasurement device 110 shown in FIGS. 4A and 4B but mainly differs in that the biomeasurement device 710 includes an extendible member 700 that is coupled to a housing 715 of the biomeasurement device 710 (e.g., as opposed to the free-standing extendible member 300 that is not coupled to the housing 115) such that the extendible member 700 is movable between a collapsed-storage position (FIGS. 7A and 7D) and an extended-generally-upright position (FIG. 7C).

The extendible member 700 includes a multitude of telescoping parts 701a-c such that the extendible member 700 is extendible from its collapsed configuration (FIGS. 7A and 7E-7G) to an extended configuration (FIG. 7C). When the extendible member 700 is fully collapsed (FIG. 7A), the extendible member 700 has a first length and when the extendible member 700 is fully extended (FIG. 7C), the extendible member 700 has a second length that is greater than the first length. For example, the second length is about two times the first length. For another example, the second length is about three times the first length. For another example, the first length is about one foot and the second length is about three feet. Various other lengths are contemplated for the extendible member 700 in the collapsed and extended configurations. While the extendible member 700 is shown as having the telescoping parts 701a-c with a generally circular cross-sectional shape, the telescoping parts 701a-c can have any shaped cross-section, such as, for example, generally square, generally rectangular, generally triangular, generally oval, generally polygonal, or any combination thereof. The telescoping parts 701a-c can remain in the extended position automatically and/or by engaging a locking mechanism (not shown).

The extendible member 700 includes a coupling mechanism 730 that extends from a top or first end of the extendible member 700. The coupling mechanism 730 is the same as, or similar to, the coupling mechanism 330 in that the coupling mechanism 730 is a universal coupling mechanism that is adjustable to securely hold therein, in a releasable fashion, a variety of sizes, types, makes, models, etc. of the mobile electronic device 150 (FIG. 7C).

The extendible member 700 includes a pivotable-pin assembly 705 that extends from a bottom or second end of the extendible member 700. The pivotable-pin assembly 705 includes four pins protruding from the second end of the extendible member 700. Two of the four pins extend along a first axis that is generally perpendicular to a central axis of the extendible member 700 and the other two of the four pins extends along a second axis that is parallel to the first axis and generally perpendicular to the central axis of the extendible member 700. The pivotable-pin assembly 705 is designed and positioned to engage a track 735 (FIGS. 7D-7G) of the biomeasurement device 710 in a slidable and/or pivotable fashion as described below.

The housing 715 of the biomeasurement device 710 includes a cavity 716 for storing the extendible member 700 therein when not in use (e.g., when not conducting a verified weigh-in). The housing 715 of the biomeasurement device 710 also includes a cutout or notch 717 for accommodating a portion of the extendible member 700 when the extendible member 700 is in the extended-generally-upright position (FIG. 7C). The housing 715 and/or the cavity 716 form the track 735 along which the pivotable-pin assembly 705 slides and/or pivots. For example, in some implementations, the pivotable-pin assembly 705 operatively engages the track 735 such that the extendible member 700 is able to slide relative to the housing 715 from the collapsed-storage position (FIGS. 7A and 7D) to a collapsed and generally horizontal position (FIGS. 7B and 7E). After reaching the collapsed and generally horizontal position (FIGS. 7B and 7E), the pivotable-pin assembly 705 is further able to pivot relative to the housing 715 within the track 735 into a first intermediate position (FIG. 7F) and then the pivotable-pin assembly 705 drops downward slightly relative to the housing 715 within the track 735 into a second position (FIG. 7G) where the extendible member 700 is in a collapsed-generally-upright position. Once in the collapsed-generally-upright position, the extendible member 700 can be extended into the extended-generally-upright position (FIG. 7C).

The angle of the extendible member 700 relative to horizontal is determined by the portion of the track 735 engaging the pivotable-pin assembly 705 when the extendible member 700 is in a collapsed-generally-upright position. As such, the angle can vary depending on the design and orientation of the track 735. In some implementations, the angle of the extendible member 700 relative to horizontal in the collapsed-generally-upright position (and/or in the extended-generally-upright position shown in FIG. 7C) is between about thirty degrees and about ninety degrees. In some other implementations, the angle of the extendible member 700 relative to horizontal in the collapsed-generally-upright position (and/or in the extended-generally-upright position shown in FIG. 7C) is between about forty-five degrees and ninety degrees. In yet some other implementations, the angle of the extendible member 700 relative to horizontal in the collapsed-generally-upright position (and/or in the extended-generally-upright position shown in FIG. 7C) is between about fifty-five degrees and about seventy degrees. In yet some other implementations, the angle of the extendible member 700 relative to horizontal in the collapsed-generally-upright position (and/or in the extended-generally-upright position shown in FIG. 7C) is between about zero degrees and about one hundred and eighty degrees. Various other angles of the extendible member 700 relative to horizontal are contemplated, such as, for example, about five degrees, about ten degrees, about fifteen degrees. In some of such implementations, the extendible member 700 may further include a leg (not shown) that extends outward from the extendible member 700 in the extended-generally-upright position and rests on and/or engages the floor to aid in supporting the weight of the extendible member 700 itself (and/or any item(s) coupled thereto, like a mobile electronic device).

The biomeasurement device 710 includes two electronic displays 720 that are viewable and able to display a variety of information (e.g., the same information described herein). As shown, the two electronic displays 720 are coupled to the housing 715 on opposite sides of the notch 717. However, in some alternative implementations, the notch 717 and/or the electronic displays 720 are moved such that the two electronic displays 720 are a single electronic display (not shown) coupled to the housing 715.

To aid in preventing the housing 715 from tipping over when the extendible member 700 is in the extended-generally-upright position (FIG. 7C) and/or coupled with the mobile electronic device 150 (e.g., when a user is not standing on the housing 715), one or more counter-weights (not shown) can be positioned within the housing 715. For example, a counter-weight(s) may be positioned within the housing 715 in the end opposite the end of the notch 717 and/or the electronic displays 720. The biomeasurement device 710 can also include a number of feet 728 (the same as, or similar to, the feet 528).

While not shown in FIGS. 7A-7G, the biomeasurement device 710 includes the same, or similar, components contained in the biomeasurement device 110, such as, for example, a wireless communication module, a memory device storing instructions, one or more processors, one or more speakers, one or more input devices (e.g., toe-push buttons), etc., or any combination thereof.

Figure 8:
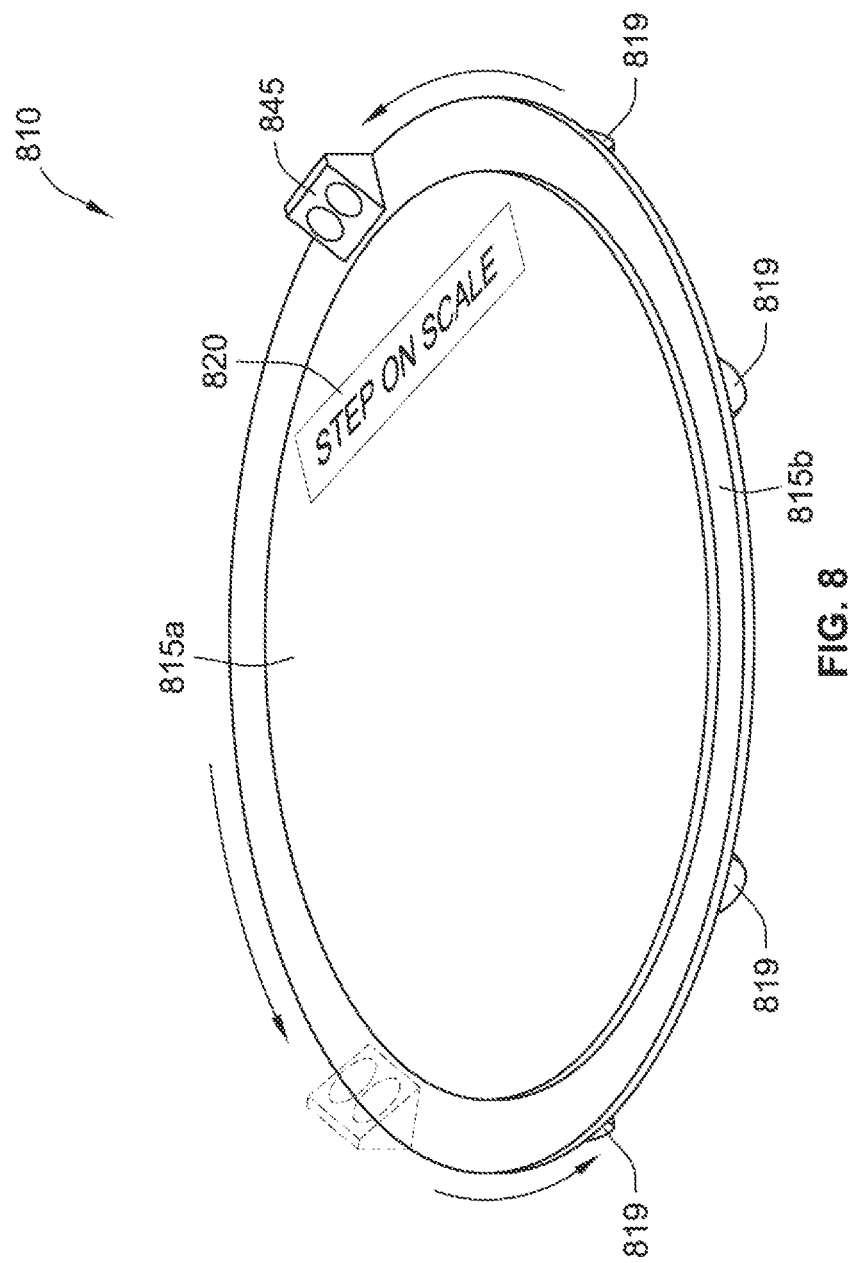
FIG. 8 is a perspective view of a scale with a rotating housing, according to some implementations of the present disclosure.

Now referring to FIG. 8, an alternative biomeasurement device 810 is shown for use by itself and/or within the weight verification system 100 as described herein. The biomeasurement device 810 includes a main housing 815a, a rotating housing 815b, an electronic display 820, and a camera 845. The rotating housing 815b generally has a ring shape and is positioned around the main housing 815a and operatively coupled thereto via a drive system (not shown) that is able to cause the rotating housing 815b to rotate about the main housing 815a in a clockwise and/or counterclockwise direction. The camera 845 is mounted to the rotating housing 815b such that rotation of the rotating housing 815b causes the camera 845 to rotate. As such, the camera 845 is able to capture a 360 degree view (e.g., a body scan or body image) of a user standing on the main housing 815a. In some implementations, the camera 845 includes a fisheye lens, a flash, dual lenses, etc., or any combination thereof.

The rotating housing 815b can include a multitude of roller/wheels 819 that aid in the rotating housing 815b moving/rotating about the main housing 815a. To aid in the main housing 815a remaining stationary when the rotating housing 815b is moving/rotating, the main housing 815a can include a number of feet (not shown) that are the same as, or similar to, the feet 528.

The biomeasurement device 810 includes the electronic display 820 that is viewable and able to display a variety of information (e.g., the same information described herein). While not shown, a second electronic display can be included and coupled to the rotating housing 815b.

While not shown in FIG. 8, the biomeasurement device 810 includes the same, or similar, components contained in the biomeasurement device 110, such as, for example, a wireless communication module, a memory device storing instructions, one or more processors, one or more speakers, etc., or any combination thereof.

Figure 9:
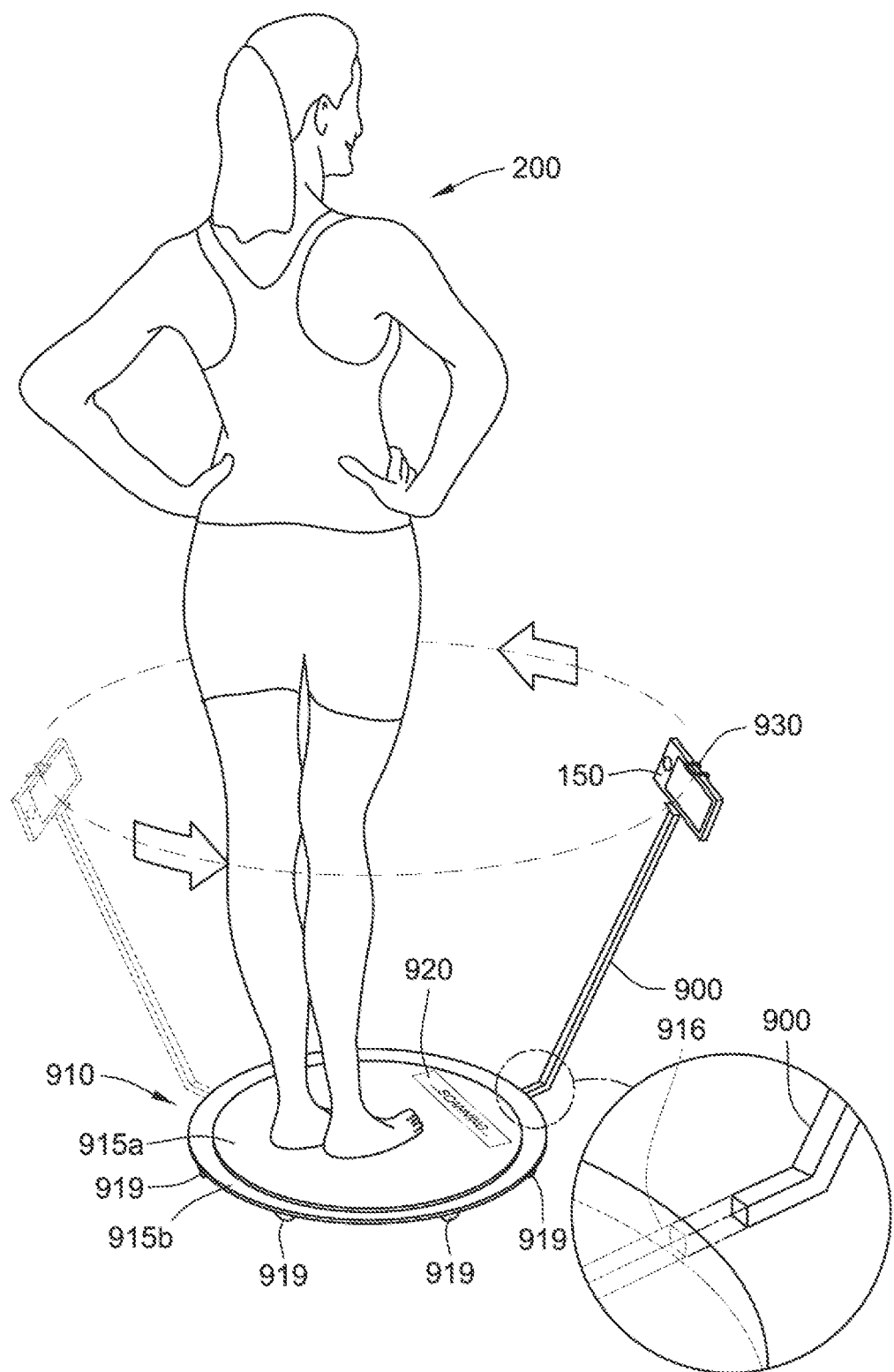
FIG. 9 is a perspective view of a scale with a rotating housing coupled to a removably attachable rod member, according to some implementations of the present disclosure.

Now referring to FIG. 9, an alternative biomeasurement device 910 is shown for use by itself and/or within the system 100 as described herein. The biomeasurement device 910 is similar to the biomeasurement device 810 but mainly differs in that instead of the biomeasurement device 910 including a built-in camera, the biomeasurement device 910 includes a removably attachable rod member 900 with a coupling mechanism 930 that is coupled to a rotating housing 915b of the biomeasurement device 910. The coupling mechanism 930 is the same as, or similar to, the coupling mechanism 330 in that the coupling mechanism 930 is a universal coupling mechanism that is adjustable to securely hold therein, in a releasable fashion, a variety of sizes, types, makes, models, etc. of the mobile electronic device 150.

The biomeasurement device 910 includes a main housing 915a, the rotating housing 915b, an electronic display 920, and the removably attachable rod member 900. The rotating housing 915b generally has a ring shape and is positioned around the main housing 915a and operatively coupled thereto via a drive system (not shown) that is able to cause the rotating housing 915b to rotate about the main housing 915a in a clockwise and/or counterclockwise direction. The rotating housing 915b includes a slot 916 that receives a portion of the removably attachable rod member 900 therein, thereby coupling the removably attachable rod member 900 with the rotating housing 915b. The mobile electronic device 150 is held by the coupling mechanism 930 of the removably attachable rod member 900, which is mounted to the rotating housing 915b, such that rotation of the rotating housing 915b causes the mobile electronic device 150 to rotate. As such, a camera of the mobile electronic device 150 is able to capture a 360 degree view (e.g., a body scan or body image) of the user 200 standing on the main housing 915a.

The rotating housing 915b can include a multitude of roller/wheels 919 that aid in the rotating housing 915b moving/rotating about the main housing 915a. To aid in the main housing 915a remaining stationary when the rotating housing 915b is moving/rotating, the main housing 915a can include a number of feet (not shown) that are the same as, or similar to, the feet 528.

The biomeasurement device 910 includes the electronic display 920 that is viewable and able to display a variety of information (e.g., the same information described herein). While not shown, a second electronic display can be included and coupled to the rotating housing 915b.

While not shown in FIG. 9, the biomeasurement device 910 includes the same, or similar, components contained in the biomeasurement device 110, such as, for example, a wireless communication module, a memory device storing instructions, one or more processors, one or more speakers, etc., or any combination thereof.

While the removably attachable rod member 900 is shown as being a rigid member, the removably attachable rod member 900 can be replaced with a collapsible and/or extendable removably attachable rod member that is similar to the extendible member 700 and/or the free-standing extendible member 300).

Several of the scales of the present disclosure include built-in cameras. To aid the users in determining whether the cameras are on/live (e.g., recording images), one or more alert systems can be included in any of the scales and/or mobile electronic devices of the present disclosure. For example, a light ring can be placed around the lens of the camera that glows a first color (e.g., red) when the camera is on and glows a second color (e.g., green) when the camera is off.

Figures 10A, 10B:
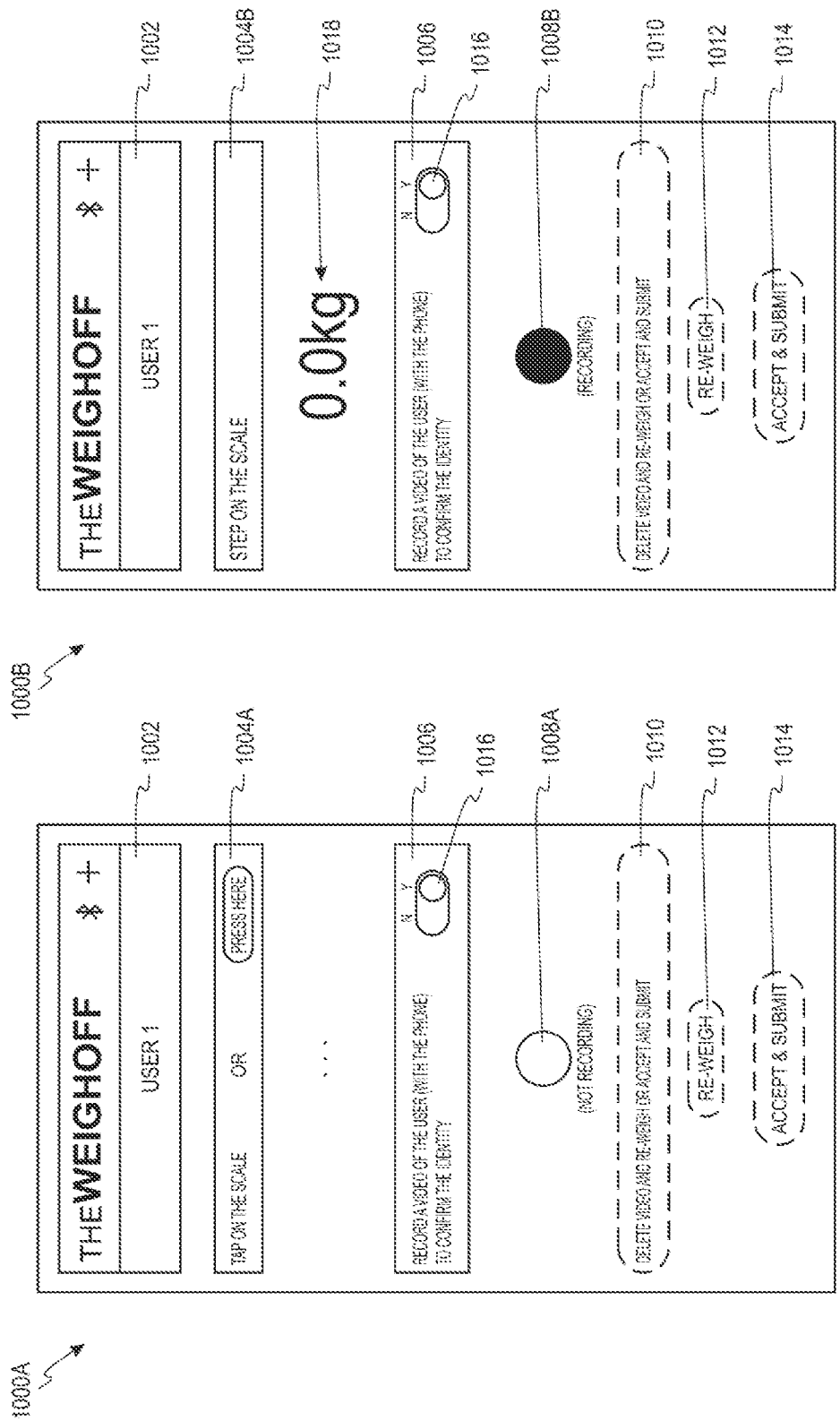
FIG. 10A is a front view of a user interface at a first time during a verified weight sequence.
FIG. 10B is a front view of a user interface at a second time during a verified weight sequence.

Now referring generally to FIGS. 10A-10D, a user interface 1000 of mobile electronic device 150 is illustrated. FIG. 10A illustrates user interface 1000A prior to a user stepping onto the scale. User interface 1000 of FIGS. 10A-10D is operable with any of the scales discussed in the present disclosures, including biomeasurement device 110, 510, 610, 710, 810, or 910. User interface 1000A may include a user indicator 1002, a text area 1004A, a record video option 1006, and a recording indicator 1008A. User interface 1000A may also include post-weigh in information area 1010, as well as user-selectable options 1012 and 1014. User-selectable option 1012 allows the user to re-weigh himself or herself, while user selectable option 1014 allows a user to accept and submit a weigh in. Both user-selectable options 1012, 1014 may at various times be grayed out or blank (or simply missing from the display) and thus may not be selectable by the user at certain times, as indicated by the dashed lines in FIG. 10A. Post-weigh in information area

1010 indicates information to the user after the user has completed the weigh-in procedure. Like user-selectable options 1012 and 1014, post-weigh in information area 1010 may be blank or may be grayed out, as indicated by the dashed lines.

User indicator 1002 indicates the identity of the user currently using the scale and mobile electronic device 150. User indicator 1002 may indicate the identity of the current user simply by displaying "User 1," "User 2," etc. User indicator 1002 may also indicate the identity of the current user by displaying the user's name, nickname, or some other type of identification. Text area 1004 may include instructions displayed to the user to command the user to take an action. In FIG. 10A, text area 1004A indicates to the user how to start the weigh-in procedure. As indicated in FIG. 10A, the user may start the weigh-in procedure by tapping on the scale or by selecting the "PRESS HERE" button. Record video option 1006 allows the user to select whether they would like a video record of themself during the weigh in to be recorded. The user may select whether or not to record a video by moving slider 1016 to either "N," indicating that a video should not be recorded, or to "Y," indicating that a video should be recorded. Finally, recording indicator 1008A can include an area that displays a blank circle or an outline of a circle when the mobile electronic device 150 is not currently recording, and/or text that states that mobile electronic device 150 is not recording. In some implementations, the user must permit the recording of the weigh in session to participate in a weight loss competition contest.

Now referring to FIG. 10B, user interface 1000B is illustrated that reflects the state of mobile electronic device 150 when the user has begun recording a video but has not yet stepped on the scale. Text area 1004B displays text instructing the user to step onto the scale. Recording indicator 1008B displays a shaded-in or solid circle, as well as text that indicates to the user that a video is currently being recorded. As shown, post-weigh in information area 1010 and user-selectable options 1012 and 1014 are still blank or grayed out. User interface 1000B also includes weight indicator 1018, which indicates to the user the weight sensed by the scale. As user interface 1000B is shown before the user steps onto the scale, weight indicator 1018 indicates that the scale is not currently sensing any weight.

Now referring to FIG. 10C, user interface 1000C is illustrated. Here, the user has stepped onto the scale, which is currently measuring the user's weight. As shown, text area 1004C displays text indicating to the user that the scale is currently measuring the user's weight, and that a video is being recorded. Weight indicator 1018 currently shows three dots, indicating that the scale is sensing that the user has stepped onto the scale (e.g., biomeasurement device 110, 510, 610, 710, 810, 910) and that the scale is determining the user's weight. Weight indicator 1018 may display any suitable object, text, etc., to communicate that the scale is in the process of determining the user's weight after having sensed that the user has stepped onto the scale. Recording indicator 1008C may be overlaid on the top of a real-time video image 1020 of the user during the weigh-in. Real-time video image 1020 may show a continuous video of the weigh-in process, or may display a constantly updating series of still images. Real-time video image 1020 could also display a single still image captured at a point during the weigh-in process. Post-weigh in information area 1010 and user-selectable options 1012 and 1014 are still blank or grayed out.

Now referring to FIG. 10D, user interface 1000D is shown after the user has completed the weigh-in. Text area 1004D may display the word "WEIGHT," indicating that user interface 1000D is now displaying the measured weight. Weight indicator 1018 now displays the user's measured weight. Recording indicator 1008D indicates that the video recording has been completed and that no video is currently being recorded. Recording indicator 1008D also indicates that a video that may be played, by taking the form of a play button, i.e. a sideways-pointing triangle. Recording indicator 1008D is responsive to user input, for example the user manually pressing recording indicator 1008D when it appears on a touchscreen of mobile electronic device 150. Recording indicator 1008D is now overlaid on top of still frame 1022, which generally displays a still frame from the recorded video. When the user manually presses on recording indicator 1008D, still frame 1022 transforms into the recorded video, which is then played for the user. In general, the recorded video will include an image or images or video showing the user stepping onto the scale, the user standing on the scale when the scale determines the user's weight, and the user stepping off of the scale. In user interface 1000D, post-weigh in information area 1010 and user-selectable options 1012 and 1014 are no longer grayed out or blank. Post-weigh in information area 1010 now indicates to the user that the user can either delete the video and re-weigh himself or herself, or that the user can accept the weigh-in and submit the video (e.g., to be verified). User-selectable option 1012 is operable to accept user input to re-weigh the user. User-selectable option 1014 is operable to accept the result of the weigh-in and submit the video.

Figure 11:
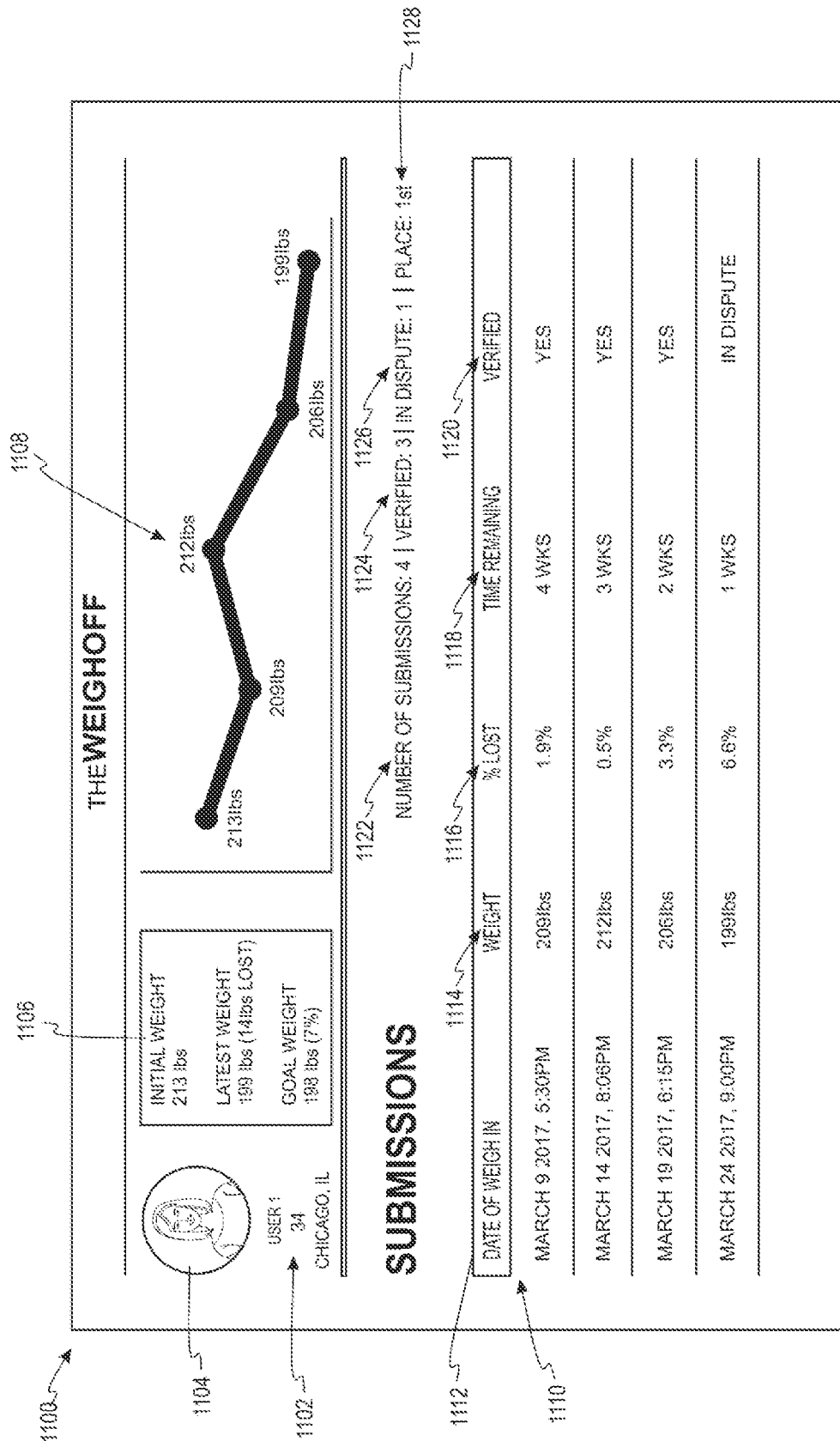
FIG. 11 is a front view of a user profile accessible by a user.

Referring now to FIG. 11, a user profile 1100 is illustrated. User profile 1100 may include personal user information 1102, a user profile image 1104, and contest weight information 1106. Personal user information 1102 may include the user's name, age, and location. Contest weight information 1106 may include the user's initial weight, the user's most recent weight, and indication of the difference between the user's most recent weight and the user's initial weight, the user's goal weight, and an indication of the difference between the user's goal weight and the user's initial weight. The indication of the difference between the user's most recent weight and the user's goal weight may take the form of a number of pounds lost, or a percentage. Similarly, the indication of the difference between the user's goal weight and the user's initial weight may take the form of a number of pounds or a percentage.

User profile 1100 also includes a weight graph 1108 which provides a visual indicator of the results of the user's submissions. For example, weight graph 1108 plots the recorded weights for each of the user's submissions to the contest and provides a line between each recorded weight, thus providing information on how the user has progressed during the contest. User profile 1100 further includes a weigh-in submission chart 1110, which shows details on each weigh-in submitted by the user. Each entry in weigh-in submission chart 1110 may include date and time 1112, the user's weight 1114, a percentage of weight lost 1116, the time remaining in the contest 1118, and a determination 1120 of whether the weigh-in was verified. The percentage of weight lost 1116 may be a percentage of the user's initial weight that the user has lost, or a percentage of the user's most recent weigh-in that they have lost. Weigh-in submission chart 1110 may also include information indicating a total number of submissions 1122, a number of verified submissions 1124, a number of in dispute weigh-ins 1126, and what place in the contest the user is currently in 1128.

Figure 12:
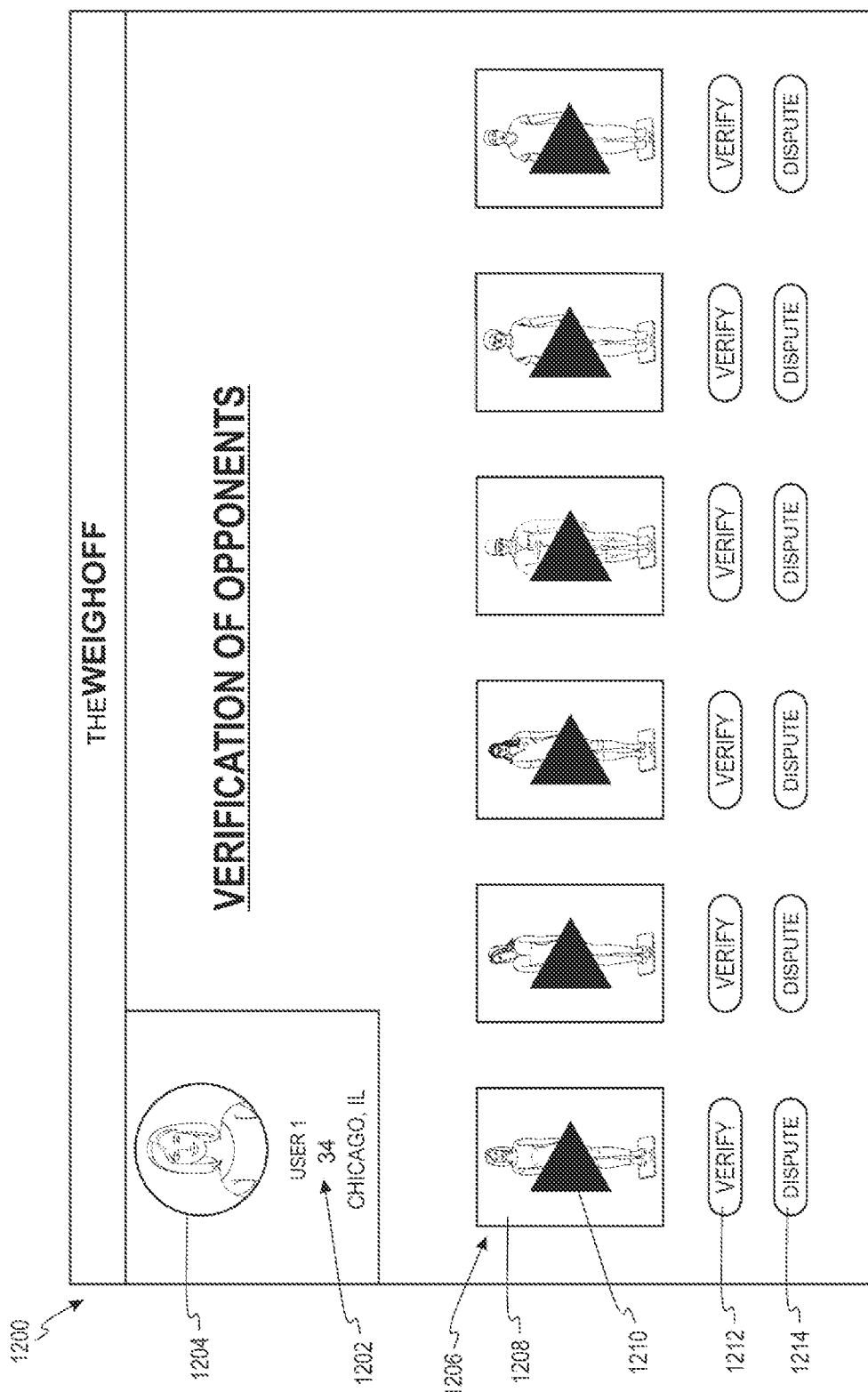
FIG. 12 is a front view of a verification screen where a user can view submitted weigh-in videos and verify or dispute the submitted weigh-in videos.

Now referring to FIG. 12, a verification screen 1200 is illustrated. Verification screen 1200 may be accessed by a user in a contest to review image data submitted by other contestants and either verify or dispute those weigh-ins. Verification screen 1200 may include personal user information 1202 such the user's name, the user's age, and the user's location, as well as a user profile image 1204. Verification screen 1200 also includes one or more verification areas 1206. Each verification area 1206 includes the image data 1208 of another user's weigh-in, a user-selectable play button 1210, a user-selectable "Verify" button 1212, and a user-selectable "Dispute" button 1214. Image data 1208 is generally uploaded and stored as a visually readable image or video of the user such that the user is personally identifiable by the visually readable image or video. The image data that is stored is not an avatar or other digital re-creations of the user, which can cause difficulties in verifying the submitted weigh-in. Avatars or other digital re-creations/representations of users generally remove much of the context from the weigh-in videos, such that specific identifying aspects of the user are replaced by generic features on a digital human. As such, avatars do not produce video images that other users can verify by viewing them, as the other users have no way to determine whether the person who submitted the weigh-in is actually the contest user. For example, a contestant's sibling or friend that has a similar body shape could step in for the contestant's weigh in without the other contestants knowing if avatar representations of the contestants were used, which would not be suitable to a contest requiring verification of weigh ins.

The user may view the image data 1208 submitted by other users by pressing the play button 1210. The user then determines whether there is any reason to dispute the other users' weigh-ins. The use The recorded weight for each submission may be displayed on verification screen 1200 (e.g., overlaid thereon and/or baked into the video) simultaneously with the recorded video of the weigh-in to allow a user to view both the weigh-in video and the recorded weight to help determine whether the weigh-in is legitimate and if it should be verified. The user may then verify the weigh-in by pressing the "Verify" button 1212. The user may also dispute the weigh-in by pressing the "Dispute" button 1214. The image data 1208 may be manually or automatically clipped or trimmed based on the time the user stepped onto the scale. For example, when a user plays a weigh-in video submitted by another user, the image data 1208 may begin playing at the moment the user stepped on the scale, even if that user's equipment captured video of the user at an earlier point before they stepped onto the scale. For another example, when a user plays a weigh-in video submitted by another user, the image data 1208 may begin playing at a predefined time prior the moment the user stepped on the scale (e.g., one, two, three, etc. seconds prior to stepping onto the scale).

In general, all weigh-ins submitted by a user are viewable by all other users in the weight loss competition and/or third party referees/judges. Submitted weigh-ins may be tagged and categorized by the method used to verify the submission. If a particular submission is disputed, a third party (such as a referee, judge, doctor, nurse, health or fitness instruction, designated user in the contest, etc.) may be utilized to administer a replacement weigh-in at an independent location. There may also be varying standards to trigger a dispute. In one implementation, a single user disputing a submitted weigh-in may trigger follow-up procedures to either determine whether the submitted weigh-in is legitimate or conduct a replacement weigh-in. In another embodiment, a predetermined percentage or number of users are required to dispute a submitted weigh-in to trigger the follow-up procedures. Similarly, a pre-determined percentage or number or users verifying a submitted weigh-in may automatically verify the submission, regardless of how many other users dispute the submitted weigh-in.

Other methods of verifying the use-submitted weigh-ins are also contemplated. For example, certified instructors or health professionals (e.g., referees/judges) may view the videos and verify the weigh-ins. Other vetted individuals may also conduct weigh-ins. For example, a user's personal health instructor could conduct a weigh-in publicly at their place of business while recording the weigh-in according to aspects of the present disclosure. Health professionals may also be able to view weigh-in videos and add notes to the videos. A representative or hired agent of the entity or person operating the weight loss contest may also administer the weigh-ins and verify weigh-in videos. Users may also be able to schedule weigh-ins with the weight loss contest operator so that the user and the contest operator can participate in a video conference during the weigh-in to record the weigh-in and monitor the weigh-in process. The system 100 may also include fingerprint detection functionality to verify the identity of the user. For example, mobile electronic device 150 may include a fingerprint reader that the user presses while stepping on to the scale. The scale may also include footprint technology to verify the identity of the user based on the user's footprint. The scale may also be capable of measuring a user's body fat percentage and pairing that measurement with the user's recorded weight. Monitoring the progress of the user's recorded weight and the user's measured body fat percentage can also assist in verifying the user's submitted weigh-in. The system 100 may also utilize facial recognition software or body recognition software to assist other users in verifying submitted weigh-ins, or to digitally verify weigh-ins. For example, the system 100 can create a first user appearance profile at the time of a first weigh-in that includes a first user face profile and a first user body profile by utilizing facial recognition software and body recognition software. Before a second weigh-in, an expected user appearance profile can be created based on at least one of the first user appearance profile, the weight of the user recorded during the first weigh-in, and the time difference between the first weigh-in and the second weigh-in. A second user appearance profile is then created during the second weigh-in and is compared to the expected user appearance profile. This comparison can be utilized by other users to assist them in determining whether to dispute a given weigh-in submission. The comparison can also be used by system 100 to digitally determine whether to verify or dispute a weigh-in submission. For example, if the measured face and body appearance varies from the expected face and body appearance by a pre-determined amount, system 100 may automatically dispute a weigh-in submission.

A variety of follow-up procedures are available once a dispute has been triggered. The user may simply be asked to submit a new weigh-in video and result. Other users of the system 100 may indicate to the user of the disputed submission what their concerns were so that if a simple mistake has been made during the weigh-in procedure, the user can correct for it. The user may be required to undergo a weigh-in conducted under the supervision of a health professional, a representative of the contest operator, or some other third party. The user may be required to undergo a weigh-in that is broadcast live to other users, to a health professional, to a representative of the contest operator, or to some other third party.

Particular weigh-ins throughout the weight loss contest may be more important than others and have special procedures. For example, the first and last weigh-ins submitted by a user, which are used to determine the total amount of weight lost during the contest, may be more important than weigh-ins submitted in the middle of the contest. Thus, a user may be required to have the first and last weigh-ins pre-verified or otherwise performed under some sort of supervision or special procedure. Further, weight lost contests having a prize over a certain dollar amount may require special procedures for weigh-ins or may require a doctor to conduct a physical for each user.

Referring to FIG. 14A, an image 1310 includes at least a portion of a subject 1300 (e.g., a head of the subject) and the biomeasurement device 110. The subject 1300 can be a user of the biomeasurement device. The image 1310 can be generated using the camera 185 of the mobile electronic device 150 (FIG. 1), for example.

In this non-limiting, exemplary implementation of FIG. 14A, the biomeasurement device 110 is used a thermometer for taking a temperature of the subject 230 (e.g., the biomeasurement device 110 includes the temperature sensor 202 described herein). As shown, the image 1310 shows that the subject 1300 is using the biomeasurement device 110 to take the temperature of the subject 1300. In this example, a tip portion of the biomeasurement device 110 is positioned under a tongue of the subject 1300. The display 192 of the biomeasurement device 110 displays the measured temperature. As described in further detail herein, the image 1310 can be used to verify the identity of the subject 1300 (e.g., using a facial recognition algorithm), to verify that the subject 1300 actually used the biomeasurement device 110 (e.g., using an object recognition algorithm to detect the biomeasurement device 110), to verify the determined temperature of the user, or any combination thereof.

Figure 13A:
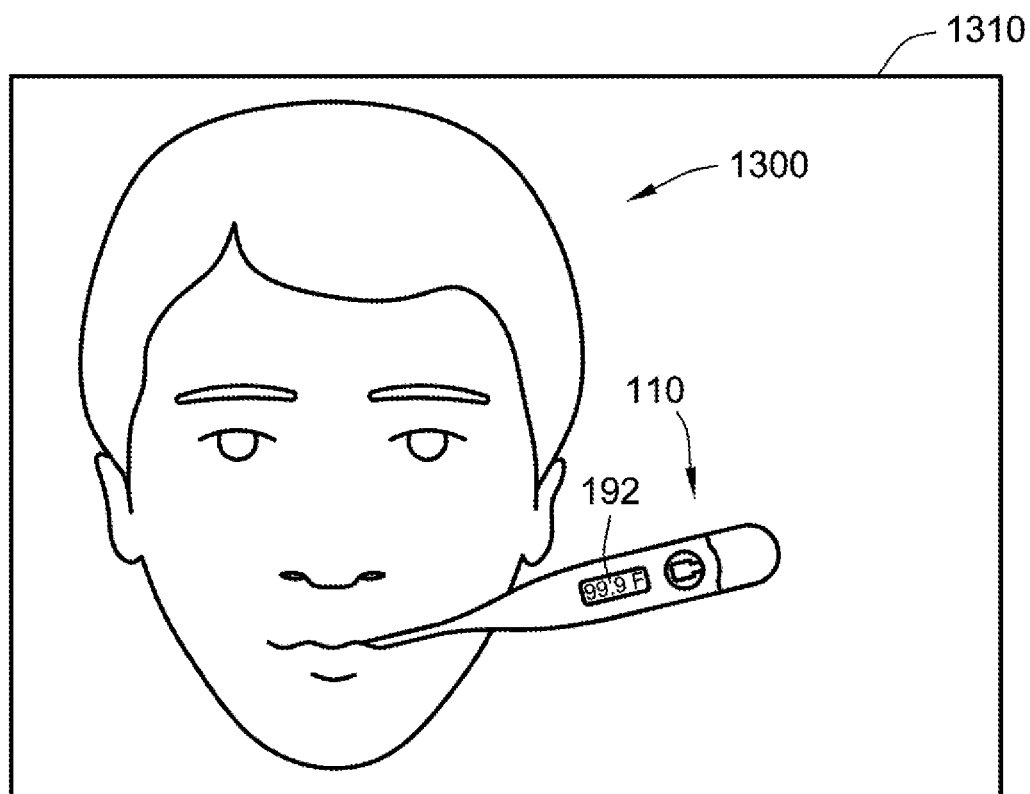
FIG. 13A is a first exemplary image of a biomeasurement device of the system of FIG. 1 and a subject, according to some implementations of the present disclosure.
Figure 13B:
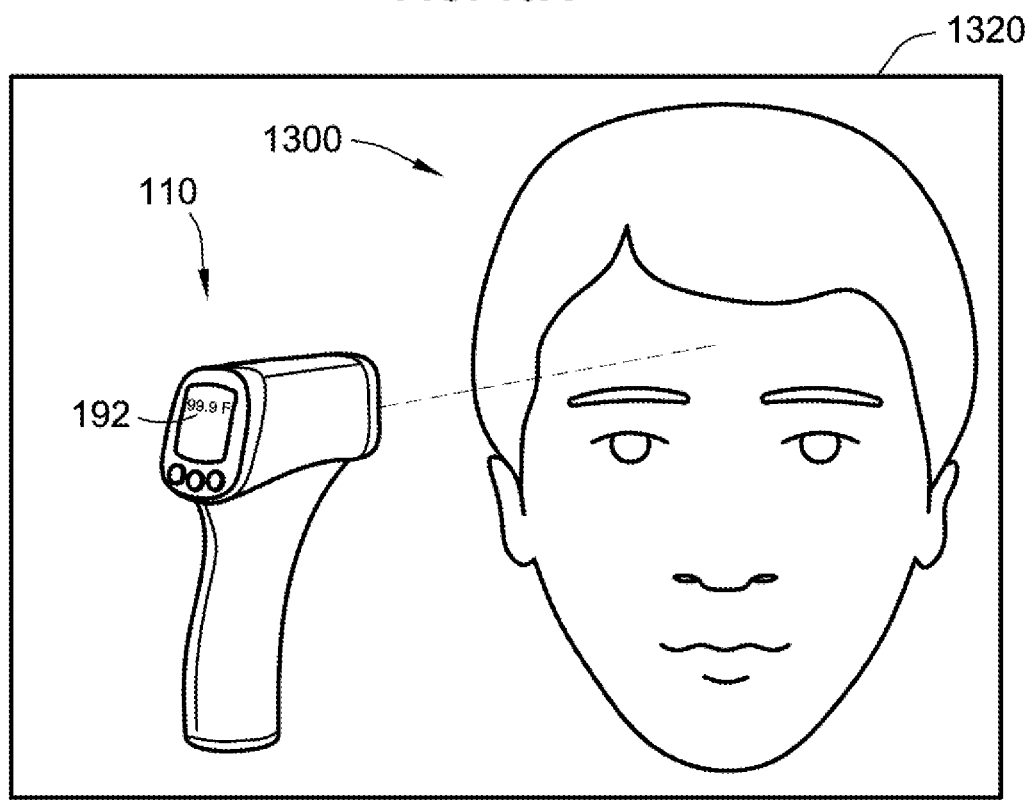
FIG. 13B is a second exemplary image of a biomeasurement device of the system of FIG. 1 and a subject, according to some implementations of the present disclosure.

Referring to FIG. 13B, in some implementations, the biomeasurement device 110 is a handheld non-contact infrared temperature gun for measuring a temperature of the user. In such implementations, an image 1320 includes at least a portion of the subject 1300 and at least a portion of the biomeasurement device 110. In such implementations, the image 1320 can be analyzed to identify that the infrared beam from the biomeasurement device 110 is correctly positioned on the head of the subject 1300 to verify the corresponding biomeasurement.

Figure 14:
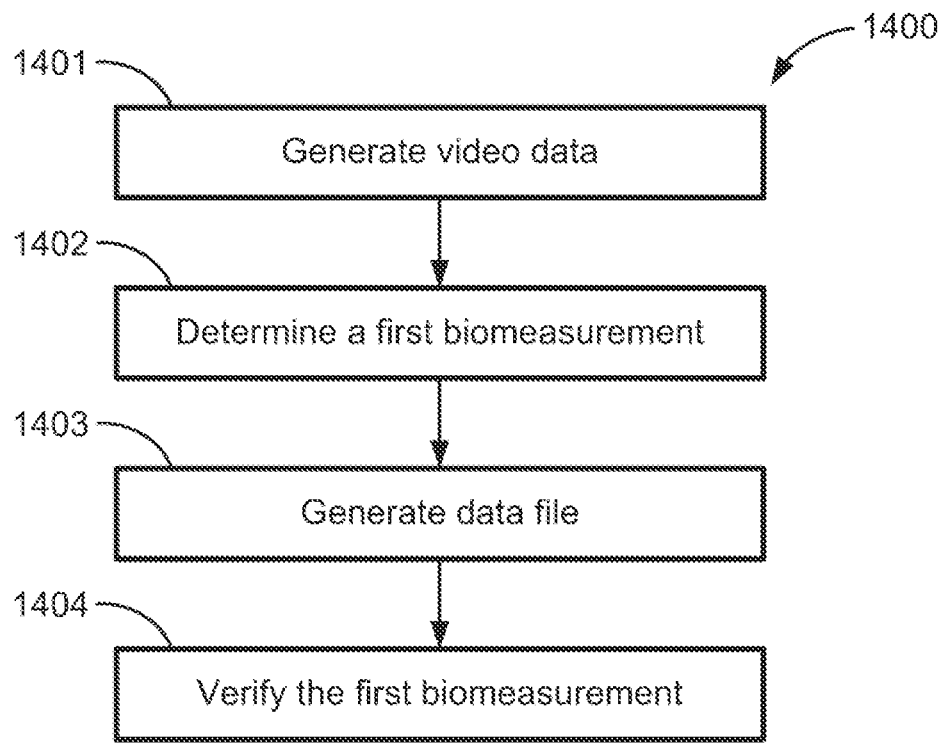
FIG. 14 is a process flow diagram for a method of verifying a biomeasurement, according to some implementations of the present disclosure.

Referring to FIG. 14, a method 1400 according to some implementations of the present disclosure is illustrated. One or more steps or aspects of the method 1400 can be implemented by the system 100 (FIG. 1) described herein.

Step 1401 of the method 1400 includes generating video data that is reproducible as a visual video clip of at least a portion of a subject. The video data can be generated by, for example, the camera 185 of the mobile electronic device 150 (FIG. 1) described herein. For example, referring to FIG. 14A, the portion of the subject in the video data can include at least a head and face of the subject. The visual video clip can be, for example, between about 1 second and about 10 minutes, between about 10 seconds and about 5 minutes, between about 30 seconds and about 3 minutes, etc. The video data also includes first time data that corresponds to the time that the video data was generated by the camera 185.

In some implementations, the visual video clip is displayed on the display 160 of the mobile electronic device 150 (FIG. 1) in substantially real time as the video data is generated by the camera 185. At least a portion of the video data can be stored in the memory 170 of the mobile electronic device 150 and/or transmitted to and stored on the server 190 via the wireless communication module 165 of mobile electronic device 150.

Step 1402 of the method 1400 includes determining, via a biomeasurement device, a first biomeasurement associated with the subject. For example, the first biomeasurement can be taken by at least one of the one or more sensors 201 of the biomeasurement device 110 (FIG. 1) described herein. The first biomeasurement can be performed manually by the subject or by a third party (e.g., a parent or caretaker of the subject). Data indicative of the determined first biomeasurement can be stored in the memory 130 of the biomeasurement device 110 and/or transmitted to the mobile electronic device 150 for storage in the memory 170 of the mobile electronic device 150 (FIG. 1). In some implementations, the first biomeasurement is taken directly from the subject. In other implementations, the first biomeasurement is taken indirectly from the subject. For example, the first biomeasurement can be associated with a sample that is taken from the subject (e.g., blood, breath, sweat, urine, tissue, feces, hair, etc.).

In some implementations, the first biomeasurement is a body temperature of the subject that is determined by the temperature sensor 202 of the biomeasurement device 110 (FIG. 1). As described in further detail herein, the body temperature of the subject can be compared to a threshold to determine if the subject has a fever. A fever can be indicative of the subject being ill (e.g., infected with an infectious disease, such as a virus). In other implementations, the first biomeasurement is a weight of the subject.

Step 1403 of the method 1400 includes generating a data file including the first biomeasurement of the user (step 1402), at least a portion of the generated video data (step 1401), the first time data associated with the video data, second time data associated with the biomeasurement. In the case where the biomeasurement is taken directly from the subject, the second time data can include a time that the biomeasurement was approximately taken from the subject (e.g., the exact the time the biomeasurement was taken, within 5 seconds of taking the biomeasurement, with 10 seconds of taking the biomeasurement, within 30 second of taking the biomeasurement, within 1 minute of taking the biomeasurement, within 5 minutes of taking the biomeasurement, etc.). In the case where the biomeasurement is taken indirectly from the subject via a sample, the second time data can include a time at which the biomeasurement was approximately taken from the sample or the time at which the sample was approximately taken from the subject.

In some implementations, at least a portion of the generated data file (step 1403) is transmitted from the mobile electronic device 150 to the server 190 such that the server 190 can analyze the data file to verify the first biomeasurement (step 304). In other implementations, the generated data file is stored on the mobile electronic device 150 such that the mobile electronic device 150 can analyze the data file to verify the first biomeasurement (step 1404).

Step 1404 of the method 1400 includes verifying the first biomeasurement of the user based at least in part on the video data included in the generated data file. As described below, there a variety of ways to verify the first biomeasurement of the user.

In some implementations, step 1404 includes automatically verifying an identity of the user. For example, the system 100 can include fingerprint detection functionality to verify the identity of the user (e.g., the mobile electronic device 150 can include a fingerprint reader that the user presses while taking the biomeasurement). As another example, the system 100 can use a facial recognition algorithm to verify the identity of the user (e.g., using the camera 185 of the mobile electronic device 150). In this manner, the first biomeasurement can be verified by authenticating the identity of the subject in the video data.

In some implementations, step 1404 further includes automatically identifying the biomeasurement device 110 in one or more images in the video data to verify the first biomeasurement. For example, step 1404 can include using an object recognition algorithm to analyze at least a portion of the video data to identify the biomeasurement device 110. In this manner, it can be confirmed that the subject actually used the biomeasurement device 110 in compliance with one or more instructions (e.g., keeping a thermometer tip under the tongue for at least 60 seconds).

In other implementations, the first biomeasurement can be manually verified by a third party that views the video data (e.g., in real-time). For example, certified health professionals (e.g., medical providers such as doctors, nurses, etc.) may view the videos and verify the biomeasurements. Health professionals may also be able to view videos and add notes to the videos. Users may also be able to schedule biomeasurements with the health professional so that the user and health professional can participate in a video conference during the biomeasurement. More specifically, the video data (step 1401) can be communicated to a medical provider (e.g., doctor) associated with the subject in substantially real-time (e.g., via the mobile electronic device 150). The determined biomeasurement (step 1402) from the biomeasurement device can also be communicated to the medical provider in real-time (e.g., via the mobile electronic device 150). The medical provider can manually review both the video data and the determined biomeasurement in substantially real-time to verify the determined biomeasurement. In such implementations, the medical provider can also communicate with the subject (e.g., via the mobile electronic device 150) to provide feedback during the taking of the biomeasurement (e.g., to provide instructions to adjust the biomeasurement device or retake the biomeasurement).

In some implementations, step 1404 includes verifying the first biomeasurement by comparing the first time data associated with the video data (step 1401) to the second time data associated with the determined first biomeasurement (step 1402). The first time data and the second time data can each include a date, a start time, and an end time. If the start time and/or the end time of the first time data and the second time data are within a threshold (e.g., within 1 second, within 3 seconds, within 5 seconds, within 10 seconds, within 30 seconds, within 1 minute, within 2 minutes, etc.), the first biomeasurement can be verified because the video image was generated by the camera at or near the same time that the biomeasurement was recorded by the biomeasurement. This ensures that the biomeasurement is accurate and the subject did not manipulate the results (e.g., submit a biomeasurement from another person, tamper with the biomeasurement device, submit a previously-recorded biomeasurement, etc.) However, if the video image was generated on a different date or a different time than the biomeasurement (e.g., the video image and biomeasurement times are more than 5 minutes apart), this indicates that the biomeasurement does not correspond to the video data and the biomeasurement will not be verified.

In some implementations, step 1404 is performed by the mobile electronic device 150 and information indicative of the results of the verification are transmitted to server 190. For example, the results can be transmitted to the server 190 only if the first biomeasurement is verified. In another examples, the results are transmitted to the server 190 regardless of whether the first biomeasurement is verified. In other implementations, step 1404 is performed by the server 190, which receives the data file during step 1403.

In some implementations, the video data (step 1401) and/or data associated with the biomeasurement (step 1402) can be encrypted such that the data can only be accessed by a verified user (e.g., the server 190, a medical provider, a health authority, etc.). For example, the video data and/or biomeasurement can be encrypted such that the subject cannot view or edit the results, thereby aiding in preventing the user from manipulating the determined biomeasurement.

Figure 15:
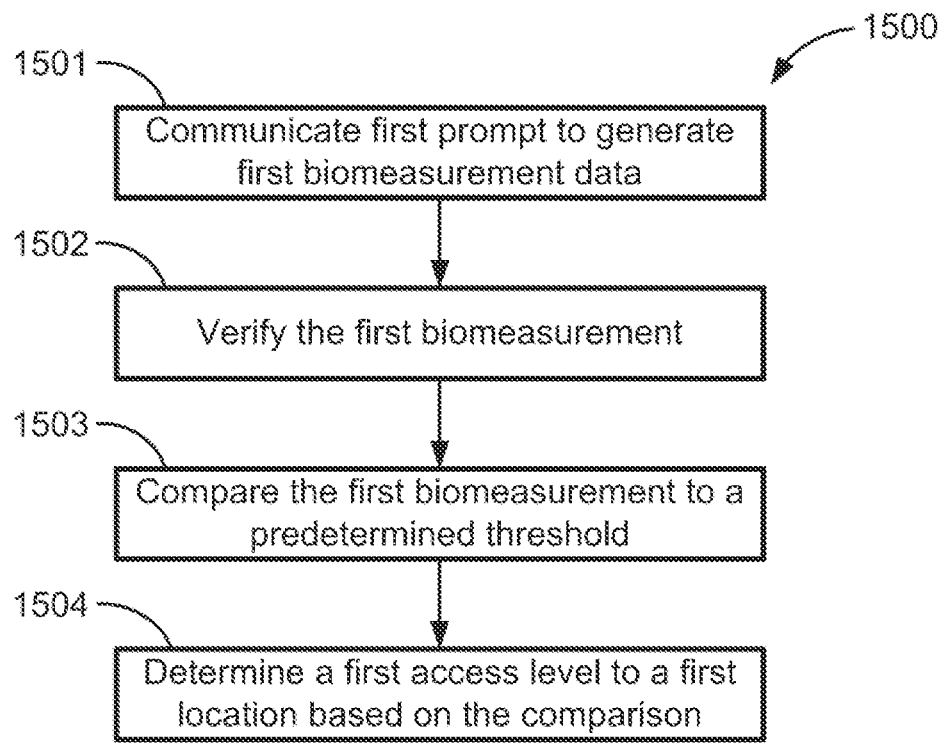
FIG. 15 is a process flow diagram for a method of determining an access level based at least in part on a verified biomeasurement, according to some implementations of the present disclosure.

Referring to FIG. 15, a method 1500 according to some implementations of the present disclosure is illustrated. One or more steps or aspects of the method 1500 can be implemented by the system 100 (FIG. 1) described herein.

Step 1501 of the method 1500 includes providing a first prompt to generate first biomeasurement data. The first prompt generally prompts the user to perform a biomeasurement using the biomeasurement device 110 and/or mobile electronic device 150 via, for example, alphanumeric text, audio, or both. The first prompt can be communicated to the subject via the biomeasurement device 110 and/or mobile electronic device 150. The first biomeasurement data includes a first biomeasurement of the subject determined by a biomeasurement device (which is the same as, or similar to, the biomeasurement of step 1402 of the method 1400), first video data generated by a camera of the electronic device (which is the same as, or similar to, the video data of step 1401 of the method 1400), the first video data being reproducible as a first video clip of at least a portion of the subject and at least a portion of the biomeasurement device, time data corresponding to a time that the biomeasurement of the subject was determined by the biomeasurement device and a time that the video data was generated by the camera of the electronic device, or any combination thereof.

Step 1502 of the method 1500 is the same as, or similar to, step 1404 of the method 1400 (FIG. 14) and includes analyzing the first biomeasurement data to verify the first biomeasurement (e.g., a temperature of the subject).

Step 1503 of the method 1500 includes comparing the verified first biomeasurement to a predetermined threshold. As described above, in some examples, the first biomeasurement is a temperature (e.g., body temperature) of the subject. In such examples, the predetermined threshold is a temperature that is indicative of a fever (e.g., at least about 100 degrees Fahrenheit, at least about 100.5 degrees Fahrenheit, at least about 101 degrees Fahrenheit, at least about 102 degrees Fahrenheit, etc.). In some implementations, the threshold can be selected to be indicative of a low grade fever or a high grade fever. Thus, the verified first biomeasurement (step 1602) can be compared to the predetermined threshold to determine whether the subject has a fever.

In some implementations, the method 1500 includes determining or modifying the predetermined threshold based at least in part on a profile associated with the subject, a second biomeasurement of the subject (e.g., heart rate), physiological data associated with the subject (e.g., movement), an ambient temperature, the first time data, or any combination thereof. For example, the predetermined threshold can be increased or decreased to account for natural increases or decreases in body temperature (e.g., due to physical activity, which can be identified based on heart rate and/or motion) or ambient temperature. Additionally, the predetermined threshold can be modified based on information in the user profile described above, such as the age of the subject and/or the sex of the subject.

Step 1504 of the method 1500 includes determining a first access level to a first location based at least in part on the comparison (step 1503). As described herein, a fever can be indicative of the subject being sick, and potentially a threat to spread illness to others. These concerns are especially poignant in the context of an epidemic or pandemic. Thus, if the verified first biomeasurement (step 1502) exceeds the predetermined threshold (step 1503), the subject can be restricted from accessing certain locations (e.g., a place of employment, school or classes, places of public accommodation, public transportation, etc.) to aid in preventing spread of the illness.

The first access level can be selected from a plurality of access levels. For example, the plurality of access levels can be binary (e.g., full access to the location or no access to the location). In another example, the plurality of access levels can permit partial access to the location (e.g., the subject can enter certain areas or rooms within the location, but not others).

In some implementations, the subject is restricted from accessing one or more locations responsive to the first verified biomeasurement meeting or exceeding the predetermined threshold. In other words, the subject can freely access the locations unless and until the first verified biomeasurement meets or exceeds the predetermined threshold. In other implementations, the subject is restricted from accessing one or more locations unless it is determined that the first verified biomeasurement is lower than the predetermined threshold. In other words, the subject cannot access the locations unless and until the first verified biomeasurement is lowers than the predetermined threshold.

The first access level can be enforced in a variety of manners. For example, step 1504 can include automatically modifying or revoking access or security credentials for the first location (e.g., deactivating a key fob, deactivating an entry code/pin, etc.) In some implementations, information indicative of the first access level is communicated to a server or individual(s) associated with the first location (e.g., human resources or an office administrator at a place of employment, a school administrator or nurse, etc.). In one specific example, information associated with the subject and the first access level can be communicated to a security desk or checkpoint at the first location (e.g., such that the security desk does not issue a visitor badge to the subject). In yet another example, facial recognition information associated with the user and information indicative of the first access level can be communicated to a facial recognition system to identify the user at the first location and implement the first access level (e.g., alert security).

In some implementations, an indication of the first access level is communicated to the subject (e.g., via the display 160 of the mobile electronic device 150 or the display 192 of the biomeasurement device 110). In this way, the subject will know whether and/or to what extent they can access the first location before attempting to travel to the first location. The subject can be dissuaded from leaving the home to travel to the first location if the subject knows that they cannot enter the first location, further aiding in preventing the spread of any illness the subject may have. To this end, in some implementations, the first access level can restrict access to transportation (e.g., public transportation by deactivating a fare card) to further aid in dissuading and/or preventing the subject from traveling outside the home.

In some implementations, the method 1500 includes repeating steps 1501-1505, causing the electronic device to communicate a second prompt to the subject to generate second biomeasurement data, verifying the second biomeasurement of the subject, comparing the second verified biomeasurement data to the predetermined threshold, and determining a second access level for the subject for the first location based at least in part on the comparison between the second verified biomeasurement data and the predetermined threshold. The second access level can be the same as, or different than, the first access level.

The second prompt can be communicated to the subject at a predetermined time subsequent to the first prompt (e.g., at least about 1 hour, at least about 3 hours, at least about 6 hours, at least about 8 hours, at least about 12 hours, or at least about 24 hours, at least about 48 hours, at least about 72 hours, between about 3 hours and about 24 hours, etc.). For example, the first verified biomeasurement reveals that the subject has a fever, the second prompt can be about 24 hours after the first prompt.

Figure 16:
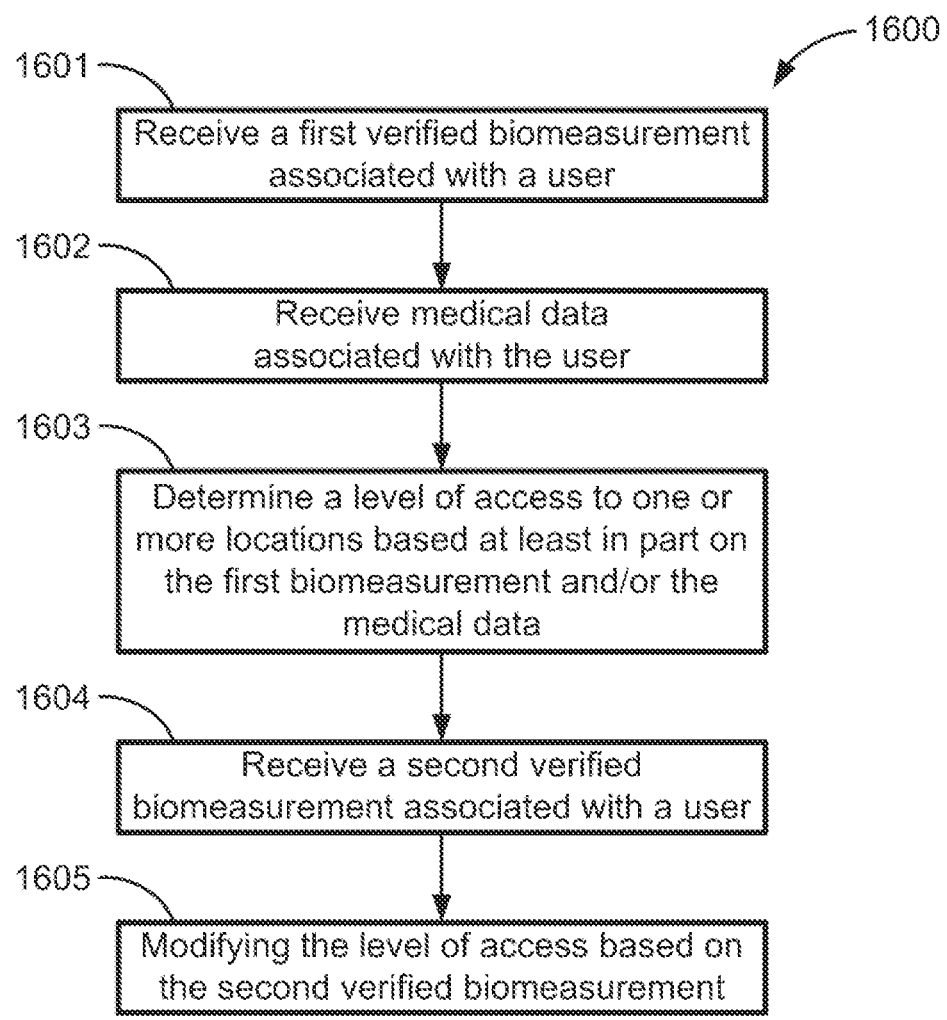
FIG. 16 is a process flow diagram for a method of a method of determining an access level based at least in part on a verified biomeasurement, according to some implementations of the present disclosure.

Referring to FIG. 16, a method 1600 according to some implementations of the present disclosure is illustrated. One or more steps or aspects of the method 1600 can be implemented by the system 100 (FIG. 1) described herein.

Step 1601 of the method 1600 includes receiving a first verified biomeasurement associated with a subject, medical data associated with the subject, or both. The first verified biomeasurement and can be received by the mobile electronic device 150 and/or the server 190 (e.g., from the biomeasurement device 110).

Step 1602 of the method 1600 includes receiving medical data associated with the subject. The medical data can include, for example, information indicative of the subject having been vaccinated for the disease, the subject having been tested for the disease, the subject having been diagnosed with the disease, the subject having recovered from the disease, the subject having antibodies associated with the disease, the subject having been in contact with one or more persons having been diagnosed with the disease, or any combination thereof. The medical data can be received by the mobile electronic device 150 and/or the server 190 (e.g., from a medical provider or database).

Step 1603 of the method 1600 includes determining a level of access to one or more locations based at least in part on the first verified biomeasurement (step 1601), the medical data (step 1602), or both.

Step 1604 of the method 1600 includes receiving a second verified biomeasurement associated with a subject. The second verified biomeasurement is associated with a second time that is subsequent to the first time (e.g., about 24 hours after the first biomeasurement).

Step 1605 of the method 1600 includes modifying the level of access based at least in part on the second verified biomeasurement (step 1604). For example, if the first verified biomeasurement indicates that the subject has a fever, the subject will be restricted as described herein. However, if the second verified biomeasurement indicates that the subject no longer has the fever, the level of access will be modified such that the restrictions are removed. Conversely, if the first verified biomeasurement indicates that the subject does not fever, but the second verified biomeasurement indicates that the subject does have a fever, the level of access will be modified such that the restrictions described herein are put in place.

Figure 17:
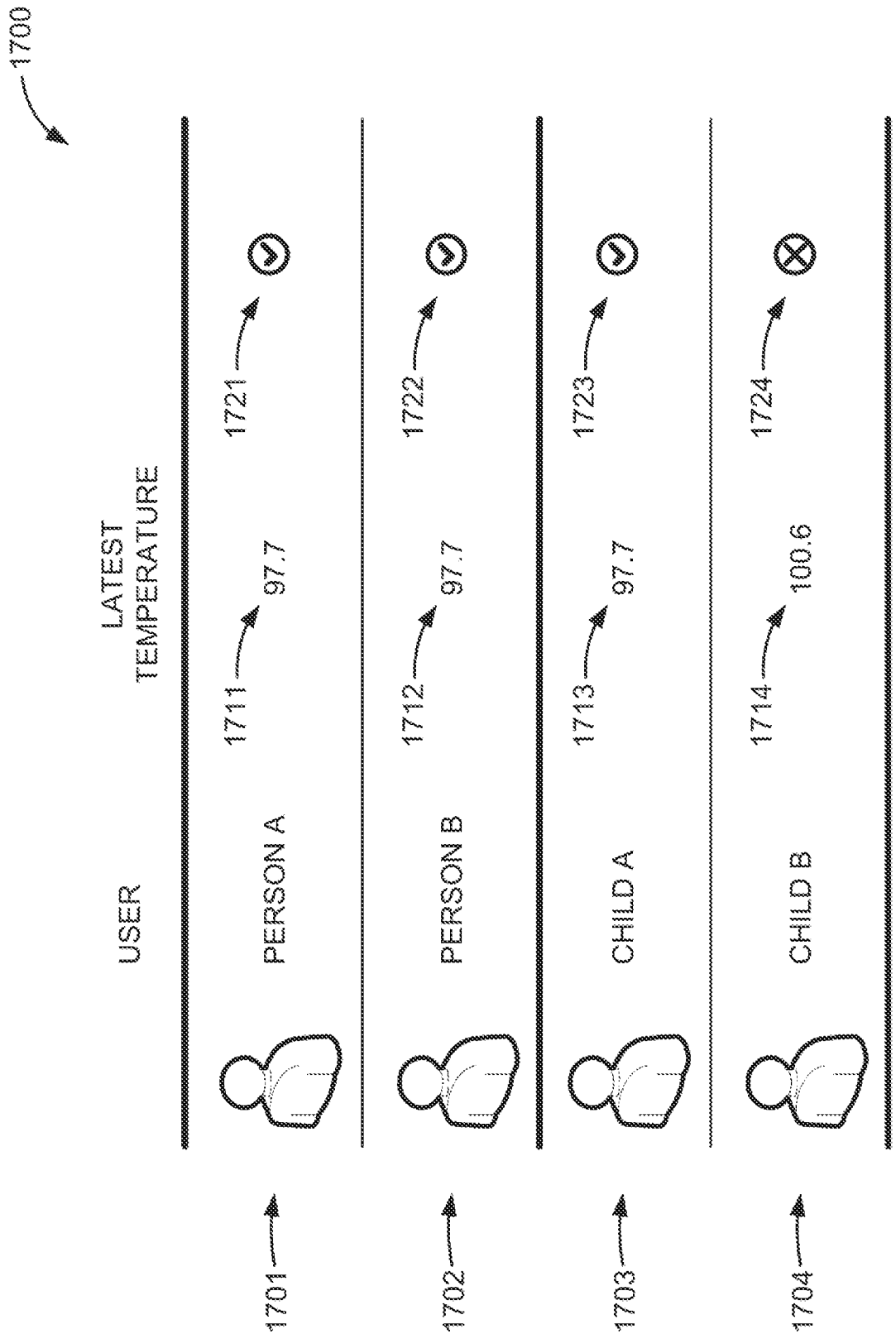
FIG. 17 illustrates an exemplary dashboard including verified biomeasurements for one or more persons, according to some implementations of the present disclosure.

Referring to FIG. 17, an exemplary biomeasurement dashboard 1700 is illustrated. The dashboard 1700 includes biomeasurement information for individuals 1701-1704.

Each individual 1701-1704 is represented on the dashboard 1700 with one or more associated indicium (e.g., alphanumeric text including the names of the individuals 1701-1704, thumbnail images of the individuals 1701-1704, etc.). The dashboard 1700 can be displayed by, for example, the display 160 of the mobile electronic device 150 (FIG. 1) described herein (e.g., within an application installed on the mobile electronic device 150).

The dashboard 1700 also includes verified biomeasurement indicia 1711-1714 corresponding to each of the individuals 1701-1704. The verified biomeasurement indicia 1711-1714 are indicative of a verified biomeasurement of each of the individuals 1701-1704. In the example of FIG. 17, the verified biomeasurement indicia 1711-1714 are indicative of a temperature of each of the individuals. In some implementations, the verified biomeasurement indicia 1711-1714 include alphanumeric text with a differing colors based on whether the corresponding temperature value is above or below a predetermined threshold (e.g., red text if the biomeasurement exceeds the predetermined threshold and green text if the biomeasurement is lower than the predetermined threshold).

The dashboard 1700 also includes pass/fail indicia 1721-1724 corresponding to each of the individuals 1701-1704 and verified biomeasurement indicia 1711-1714. Each of the pass/fail indicia 1721-1724 indicate whether the corresponding verified biomeasurement indicia 1711-1714 exceed the predetermined threshold (e.g., a fever). For example, as shown, the pass/fail indicia 1721-1724 include a first symbol (e.g., green check marks) for temperatures that are below the threshold (e.g., no fever) and a second symbol (e.g., a red "x") for temperatures that are above the threshold (e.g., a fever). In this manner, a user of the dashboard 1700 can easily identify one or more of the individuals 1701-1704 that have a fever (e.g., to restrict or prohibit those individuals from accessing a location).

While the dashboard 1700 is shown as including biomeasurement information for four individuals 1701-1704, more generally, the dashboard 1700 can include biomeasurement information for any number of individuals (e.g., one individual, ten individuals, fifty individuals, etc.). Similarly, while one biomeasurement 1711-1714 is shown for each of the individuals 1701-1704, more generally, any number of biomeasurements can be shown for each individual 1701-1704 (e.g., two biomeasurements, five biomeasurements, etc.).

According to some implementations, use of the present disclosure to conduct verified biomeasurements can be used in telemedicine practices such that doctors and/or providers can be assured that the data received is/was verified/confirmed as belonging to the patient assumed to have sent the data. In some instances, when a parent communicates with a child's doctor or a spouse's doctor, mix-ups that might have otherwise occurred by associating the data with the sender as opposed to the individual associated with the health data can be reduced and or prevented by verifying the health data/biomeasurements using the methods of the present disclosure. Further, insurance companies can leverage the benefits of verified biomeasurements to ensure that the insured individual is the individual that is providing the health data. As such, insurance companies can offer more customized plans based on periodic verified health data packets (e.g., data files) including one or more biomeasurements associated with the insured individual.

Referring to FIG. 18, a first indicium 1810 and a second indicium 1820 are displayed on the display 160 of the mobile electronic device 150 described herein. The indicia 1810-1820 can be used to communicate to others that the subject associated with the mobile electronic device 150 has a verified biomeasurement, such as, for example, a verified temperature that is below a fever threshold. The first indicium 1810 is a barcode that can be scanned by a scanner (e.g., camera) of an external device 1820 (e.g., that is the same as, or similar to, the mobile electronic device 150 described herein). The second indicium 1820 is a symbol (e.g., a checkmark or "x") or alphanumeric text that is indicative of the verified biomeasurement for the subject associated with the mobile electronic device 150. The second indicium 1820 can be viewed manually by a third party, or scanned by the scanner 1822 of the external device 1820.

In some implementations, the mobile electronic device 150 can communicate with the external device 1800 via RFID (e.g., like contactless payment) to communicate information indicative of the verified biomeasurement. In such implementations, the external device 1800 can include an RFID reader 1824 that communicates with the mobile electronic device 150 when the mobile electronic device 150 is within a certain proximity to the biomeasurement device 110.

In some implementations, the first indicium 1810, the second indicium 1820, or both are displayed with other information on the display 160 of the mobile electronic device 150. For example, the first indicium 1810 and/or the second indicium 1820 with an access barcode (e.g., a boarding pass for boarding plane, a ticket for a sporting event, etc.) to indicate the verified biomeasurement to an agent at a location to allow or prohibit access to a location.

As described above, the biomeasurement devices described herein can be any Bluetooth-enabled device.

For example, for medical professionals treating those with diabetes, proper use of a diabetes injection pen is vital. Helping patients build the right habits when administering the pen is a challenge for physicians, and the use of Bluetooth Low Energy technology helps improve the success of diabetes management. When using a Bluetooth-enabled diabetes injection pen, patients would use an app to help calculate the correct dosage to inject. The app would gather data based off of what meals the patient has eaten, blood glucose meter readings, time of day, and the amount of exercise that was done before injection. A recommended dose would be given, and the patient would accept and administer the dose directly on the pen. This would make home administration of diabetes pens much more effective, especially in underserved communities.

As another example, when a patient is hooked up to an intravenous drip, a Bluetooth-enabled blood glucose monitor can be used to wirelessly alter the flow rate of the IV drip, adjusting to a patient's insulin levels. Using this mechanism helps save time out of the medical staff while also allowing for automated distress signals to physicians when a situation occurs that requires professional attention. Because Bluetooth 5 allows for different transmission rates, signals sent to the drip can use the higher data rate, while distress signals can be transmitted at the lower data rate with the longer range, reaching a physician or central computing hub that could be farther away from the patient.

In a further example, drug inhalers treat patients with medication that are best administered through the lungs. For those who suffer from asthma, inhalers are heavily relied upon, so tracking data associated with their usage can be an important tool for users looking to improve their own experience. A smart-enabled automated drug inhaler would be able to send dosage history from the inhaler to a smartphone app, letting users chart out the usage of the inhaler across the number of uses, time of day, frequency and remaining doses. If various user errors occur, the app can even provide users with online videos to help improve inhaler use.

In yet another example, outside of the hospital, Bluetooth-enabled medical devices can track patient progress in the form of data sent to the smartphone. The data can then be presented to a medical professional on the next visit or the data can be sent wirelessly to the hospital. Such a device can also be life-saving. In the event of an emergency, the device can work with the smartphone to make an emergency call, providing first responders with the patients' locations using the smartphone's GPS. Connecting these devices together under the same roof is the key to utilizing Bluetooth's greatest strength. With the interoperability of Bluetooth, the different devices—weight scales, heart rate monitors, blood pressure monitors—can track a patient's health at home and link the data together to a local hub, like a smart hub. From the smart hub, the data can be gathered and processed to be sent over long distances to a medical professional or a caregiver. This makes connected home health a lot more manageable for health professionals, who can have all the data in one central location, rather than receiving multiple different data sets and having to manage the data between them.

Various biomeasurement devices are described herein. In some implementations, such biomeasurement devices can be referred to as a biometric device. Biometric devices and/or biomeasurement devices are devices and/or systems that can be used to take and/or determine one or more measurements associated with an individual. Such measurements can, in some implementations, be measurements associated with one or more biometrics of an individual.

As described above, the systems and methods described herein can be used to verify a biomeasurement that is indicative of whether the subject has a medical condition, such as an infectious disease (e.g., COVID-19). In some implementations, the biomeasurement can include a diagnostic test for one or more diseases. For example, the biomeasurement can be a rapid antigen test or a polymerase chain reaction (PCR) test for COVID-19. In some cases, such diagnostic tests can be performed by the subject or patient themselves (e.g., in an in-home setting) rather than by a third party (e.g., a medical provider). The diagnostic test can be administered directly on the subject (e.g., a nasal or throat swab) or indirectly by taking a sample from the subject (e.g., blood, saliva, sweat, skin cells, hair, breath/air from lungs, etc. or any combination thereof) and applying the diagnostic test to the sample.

In such implementations, the systems and methods described herein can be used to verify the diagnostic test. For example, the systems and methods described herein can be used to verify that the subject administered the diagnostic test in the prescribed manner and to verify the identity of the individual taking and/or administering the diagnostic test. As another example, the systems and methods described herein can be used to verify that the diagnostic test is an authentic, trusted test (e.g., a test approved by a medical provider, an employer, or a public health authority). For instance, the mobile electronic device 150 can be used to scan an identifier (e.g., barcode) on the diagnostic test (e.g., in the same or similar manner as shown in FIG. 18) to verify the authenticity of the test and other associated information (e.g., test manufacturer, test manufacture date, batch number, etc.).

In other implementations, the systems and methods described herein can be used to verify administration of a medical treatment. For example, in response to determining that the subject has a disease based on a verified biomeasurements, the systems and methods described herein can be used to verify (e.g., manually or automatically) that the subject is adhering to a prescribed treatment, such as taking medication in the correct dosage and/or at the correct times. For instance, video data of the subject undergoing treatment can be manually verified by a third party. As another example, the mobile electronic device 150 can be used to scan an identifier (e.g., barcode) on the medication (e.g., in the same or similar manner as shown in FIG. 18) to verify the subject is taking the correct medication. As another example, the biomeasurement device 110 can be used to take a biomeasurement of the medication (e.g., weight) to verify the dosage.

In still other implementations, the systems and methods described herein can be used to verify administration of a vaccine. As described herein, it is useful to verify biomeasurements that are indicative of disease (e.g., COVID-19) to alert the subject and/or others, and potentially restrict access to certain locations if the subject has the disease to reduce the risk infecting others. While biomeasurements like body temperature and other diagnostic tests are useful to identify individuals that may transmit disease to others, this does not necessarily guarantee that no transmission will occur. Perhaps the most effective public health strategy to reduce the risk of infection is widespread vaccination. To that end, it would be useful to verify individuals that have been vaccinated (e.g., to permit or restrict access to locations accordingly), and also to verify that the administered vaccines are authentic. It is possible that unapproved, fraudulent, defective, and/or otherwise defective versions of a vaccine may be circulated, especially in the midst of a pandemic in which there is immediate and widespread demand. Further, establishing public confidence in the vaccine is useful, especially for individuals who are skeptical or apprehensive about receiving a vaccine. This verification can encourage individuals to receive the vaccine.

In some implementations, vaccination of a subject can be verified using video data (e.g., video data reproducible as a human viewable video of the subject being vaccinated). For example, the video data can be viewed and manually verified by a third party, such as a medical professional. Alternatively or additionally, the video data can be verified automatically (e.g., using an object recognition algorithm recognizing the vaccine and/or facial recognition algorithms for identifying the subject). Verification of the vaccine itself can also be performed, for example, based on an indication such as a barcode on the vaccine (e.g., on the vial, on the tube, on the syringe, etc.). More specifically, the mobile electronic device 150 can be used to scan an indication (e.g., barcode or other unique identifier) to verify the authenticity (e.g., origin) of the vaccine (e.g., including a manufacturer, a manufacture date, a batch number, etc.) in the same or similar manner as shown in FIG. 18. Alternatively, the biomeasurement device 110 can be used to take a biomeasurement (e.g., weight, temperature, color, cloudiness, viscosity, etc., or any combination thereof) of the vaccine dose to verify one or more parameters of the vaccine. In some such implementations, the verified one or more parameters can be used to verify and/or confirm that the dosage amount is correct, that the dosage is current and not expired, etc. or any combination thereof.

In some implementations, in addition to or instead of a video of the vaccine being administered to the subject, the video data includes a video of the vaccine being removed from storage and/or prepped by a medical professional.

Some vaccines need to be maintained within a predetermined temperature range to maintain their efficacy. Indeed, some vaccines directed to COVID-19 need to shipped at temperatures between 0 and −100 degrees Fahrenheit. Thus, it would be advantageous to verify that a vaccine was shipped and/or stored within the predetermined range of temperatures specified by the manufacturer before administering the vaccine to a patient. Such verification can be presented to reassure the patient that the vaccine was handled properly and will be effective. This can be especially useful for patients that are skeptical or apprehensive about taking a vaccine. The biomeasurement device 110 can be used to take a biomeasurement (e.g., temperature) of the vaccine either when it is in storage, in transit, immediately after being removed from storage, or any combination thereof to verify that the vaccine dosage has been maintained in the proper conditions.

In some such implementations, the vaccine can be monitored (e.g., continuously or intermittently, every second, every 5 seconds, every minute, every five minutes, every hour, or any other period of time) to verify that the vaccine dosage has been maintained in accordance with the manufacturer's guidelines. For example, some vaccines can be stored at room temperature after having been extracted from cold storage for a predetermined time while maintaining their efficacy. The systems and methods described herein can be used to take a plurality of biomeasurements associated with the vaccine (e.g., at a predetermined interval of every 1 minute, every 5 minutes, every 30 minutes, every hour, etc. or substantially continuously) and verify those biomeasurements. If at any time a biomeasurement exceeds a predetermined threshold (e.g., the temperature exceeds a maximum allowance temperature, the time above a certain temperature exceeds a threshold, etc.), an indication that this vaccine should not be administered can be generated.

Alternative Implementations

Alternative Implementation 1. A method comprising: generating, via a camera of an electronic device, video data that is reproducible as a visual video clip of at least a portion of a subject; determining, via a biomeasurement device, a first biomeasurement of the subject; generating a data file including (i) the first biomeasurement of the subject, (ii) at least a portion of the video data, and (iii) first time data corresponding to a time that the first biomeasurement of the subject was determined by the biomeasurement device; and verifying the first biomeasurement of the subject based at least in part on the video data included in the generated data file.

Alternative Implementation 2. The method of alternative implementation 1, further comprising transmitting the generated data file to a server, wherein the server performs the verifying the determined biomeasurement of the subject.

Alternative Implementation 3. The method of alternative implementation 1, further comprising transmitting information indicative of the verified first biomeasurement of the subject to a server.

Alternative Implementation 4. The method of alternative implementation 1, wherein the verifying the first biomeasurement is performed by the electronic device.

Alternative Implementation 5. The method of alternative implementation 1, further comprising receiving an indication to begin a verified measurement sequence prior to the generating the video data and the determining the first biomeasurement of the subject.

Alternative Implementation 6. The method of alternative implementation 1, further comprising analyzing at least a portion of the video data using a facial recognition algorithm to identify the subject.

Alternative Implementation 7. The method of alternative implementation 1, further comprising analyzing at least a portion of the video data using an object recognition algorithm to identify the biomeasurement device.

Alternative Implementation 8. The method of alternative implementation 1, wherein the video data includes second time data corresponding to a time that the video data was generated by the camera of the electronic device.

Alternative Implementation 9. The method of alternative implementation 8, wherein the verifying the first biomeasurement includes comparing the first time data associated with the time that the first biomeasurement of the subject was determined by the biomeasurement device with the second time data corresponding to the time that the video data was generated by the camera of the electronic device.

Alternative Implementation 10. The method of alternative implementation 1, wherein the biomeasurement device includes a thermometer, a temperature sensor, a heart rate sensor, a respiration sensor, a perspiration sensor, an EKG sensor, a blood pressure sensor, a blood glucose sensor, an optical sensor, an electrochemical sensor, or any combination thereof.

Alternative Implementation 11. The method of alternative implementation 1, further comprising comparing the first biomeasurement of the subject to a predetermined threshold.

Alternative Implementation 12. The method of alternative implementation 11, wherein the first biomeasurement is a body temperature of the subject and the predetermined threshold is a body temperature.

Alternative Implementation 13. The method of alternative implementation 12, wherein the predetermined body temperature threshold is at least about 100 degrees Fahrenheit, at least about 100.5 degrees Fahrenheit, or at least about 101 degrees Fahrenheit.

Alternative Implementation 14. The method of alternative implementation 11, further comprising, prior to the comparing, modifying the predetermined threshold based at least in part on a profile associated with the subject, a second biomeasurement of the subject, an ambient temperature, the first time data, or any combination thereof.

Alternative Implementation 15. The method of alternative implementation 14, wherein the profile includes information indicative of an age of the subject, a sex of the subject, a medical condition of the subject, previously recorded biomeasurements of the subject, or any combination thereof.

Alternative Implementation 16. The method of alternative implementation 14, wherein the second biomeasurement of the subject is a heart rate of the subject, a respiration rate of the subject, a perspiration rate of the subject, an activity level of the subject, or any combination thereof.

Alternative Implementation 17. The method of alternative implementation 12, further comprising, responsive to the first biomeasurement of the subject exceeding the predetermined body temperature threshold, transmitting an alert to the subject, one or more third parties, or both.

Alternative Implementation 18. The method of alternative implementation 17, wherein the one or more third parties include a medical provider associated with the subject, a government health authority, or both.

Alternative Implementation 19. The method of alternative implementation 12, further comprising, responsive to the first biomeasurement of the subject exceeding the predetermined threshold, restricting access by the subject to a first location.

Alternative Implementation 20. The method of alternative implementation 19, wherein the first location is a place of employment associated with the subject, a place of public accommodation, or public transportation.

Alternative Implementation 21. The method of alternative implementation 19, wherein the restricting access by the subject to the first location includes suspending security credentials of the subject that are associated with the first location.

Alternative Implementation 22. The method of alternative implementation 19, wherein the subject had a first level of access to the first location prior to the comparing and subsequent to the restricting access the subject has a second level of access to the first location, the second level of access being different than the first level of access.

Alternative Implementation 23. The method of alternative implementation 19, wherein the restricting access includes transmitting one or more images of the subject to a server associated with the first location.

Alternative Implementation 24. The method of alternative implementation 19, wherein the restricting access includes transmitting facial recognition data associated with the subject to a server associated with the first location.

Alternative Implementation 25. The method of alternative implementation 12, further comprising, responsive to the first biomeasurement of the subject being lower than the predetermined threshold, causing an indication to be displayed on a display of the electronic device.

Alternative Implementation 26. The method of alternative implementation 25, further comprising transmitting the indication to a third party.

Alternative Implementation 27. The method of alternative implementation 12, further comprising, responsive to the first biomeasurement of the subject being lower than the predetermined threshold, permitting the subject to access one or more locations.

Alternative Implementation 28. The method of alternative implementation 1, wherein the biomeasurement device is a scale.

Alternative Implementation 29. A method comprising: causing an electronic device to communicate a first prompt to a subject to generate first biomeasurement data, the first biomeasurement data including: (i) a first biomeasurement of the subject determined by a biomeasurement device; (ii) first video data generated by a camera of the electronic device, the first video data being reproducible as a first video clip of at least a portion of the subject and at least a portion of the biomeasurement device; and (iii) time data corresponding to a time that the biomeasurement of the subject was determined by the biomeasurement device and a time that the video data was generated by the camera of the electronic device; verifying the first biomeasurement of the subject based at least in part on the first video data and the time data; comparing the first verified biomeasurement data to a predetermined threshold; and determining a first access level for the subject for a first location based at least in part on the comparison between the first verified biomeasurement data and the predetermined threshold.

Alternative Implementation 30. The method of alternative implementation 29, wherein the first biomeasurement of the subject is a body temperature of the subject and the predetermined threshold is body temperature that is indicative of the subject having a fever.

Alternative Implementation 31. The method of alternative implementation 30, wherein the comparing the first verified biomeasurement data to the predetermined threshold includes determining whether the first biomeasurement is equal to or exceeds the predetermined threshold.

Alternative Implementation 32. The method of alternative implementation 31, wherein the determined first access level restricts the subject from entering the first location responsive to determining that the first biomeasurement is equal to or exceeds the predetermined threshold.

Alternative Implementation 33. The method of alternative implementation 31, wherein the determined first access level permits the subject to enter the first location responsive to determining that the first biomeasurement is less than the predetermined threshold.

Alternative Implementation 34. The method of alternative implementation 29, further comprising: causing the electronic device to communicate a second prompt to the subject to generate second biomeasurement data, the second biomeasurement data including: (i) a second biomeasurement of the subject determined by the biomeasurement device; (ii) second video data generated by the camera of the electronic device, the second video data being reproducible as a second video clip of at least a portion of the subject and at least a portion of the biomeasurement device; and (iii) time data corresponding to a time that the biomeasurement of the subject was determined by the biomeasurement device and a time that the video data was generated by the camera of the electronic device; verifying the second biomeasurement of the subject based at least in part on the second video data and the time data; comparing the second verified biomeasurement data to the predetermined threshold; and determining a second access level for the subject for the first location based at least in part on the comparison between the second verified biomeasurement data and the predetermined threshold.

Alternative Implementation 35. The method of alternative implementation 34, wherein the second access level is different than the first access level.

Alternative Implementation 36. The method of alternative implementation 34, wherein the second prompt is communicated to the subject at a predetermined time subsequent to the first prompt.

Alternative Implementation 37. The method of alternative implementation 36, wherein the predetermined time is at least about 1 hour, at least about 3 hours, at least about 6 hours, at least about 8 hours, at least about 12 hours, or at least about 24 hours.

Alternative Implementation 38. The method of alternative implementation 37, wherein the predetermined time is between about 3 hours and about 24 hours.

Alternative Implementation 39. The method of alternative implementation 29, further comprising transmitting the first biomeasurement data from the electronic device to a server.

Alternative Implementation 40. The method of alternative implementation 39, wherein the verifying the first biomeasurement and the comparing the first biomeasurement are performed by the server.

Alternative Implementation 41. The method of alternative implementation 29, further comprising transmitting information indicative of the first verified biomeasurement of the subject from the electronic device to a server.

Alternative Implementation 42. The method of alternative implementation 41, wherein the information indicative of the first verified biomeasurement includes at least a portion of the first biomeasurement data.

Alternative Implementation 43. A method comprising: receiving (i) a first verified biomeasurement associated with a subject, the first verified biomeasurement being associated with a first time, (ii) medical data associated with the subject, or (iii) both (i) and (ii); and determining a level of access for the subject to one or more locations based at least in part on (i) the first verified biomeasurement associated with the subject, (ii) the first medical data associated with the subject, or (iii) both (i) and (ii), wherein the level of access aids in preventing the subject from communicating a disease to one or more third parties at the one or more locations.

Alternative Implementation 44. The method of alternative implementation 43, wherein the first medical data includes information indicative of the subject having been vaccinated for the disease, the subject having been tested for the disease, the subject having been diagnosed with the disease, the subject having recovered from the disease, the subject having antibodies associated with the disease, the subject having been in contact with one or more persons having been diagnosed with the disease, or any combination thereof.

Alternative Implementation 45. The method of alternative implementation 43, wherein the first verified biomeasurement associated with the subject is a body temperature of the subject.

Alternative Implementation 46. The method of alternative implementation 43, further comprising receiving a second verified biomeasurement associated with the subject, the second verified biomeasurement being associated with a second time that is subsequent to the first time.

Alternative Implementation 47. The method of alternative implementation 46, further comprising modifying the determined level of access for the subject to the one or more locations based at least in part on the second verified biomeasurement.

Alternative Implementation 48. The method of alternative implementation 43, further comprising receiving updated medical data associated with the subject and modifying the determined level of access for the subject to the one or more locations based at least in part on the updated medical data.

Alternative Implementation 49. The method of alternative implementation 43, wherein the level of access permits the subject to fully access the one or more locations.

Alternative Implementation 50. The method of alternative implementation 43, wherein the level of access permits the subject to partially access the one or more locations.

Alternative Implementation 51. The method of alternative implementation 43, wherein the level of access restricts the subject from accessing the one or more locations.

Alternative Implementation 52. A method comprising: generating, via a camera, image data that is reproducible as an image of at least a portion of a subject; receiving, via a sensor, first biomeasurement data associated with the subject, the first biomeasurement data including a first biomeasurement of the subject; and verifying the first biomeasurement of the subject based at least in part on a comparison between at least a portion of the image data and at least a portion of the first biomeasurement data.

Alternative Implementation 53. The method of alternative implementation 52, wherein the sensor is a temperature sensor.

Alternative Implementation 54. The method of alternative implementation 52, wherein the camera is coupled to or integrated in an electronic device.

Alternative Implementation 55. The method of alternative implementation 54, wherein the sensor is coupled to or integrated in the electronic device.

Alternative Implementation 56. The method of alternative implementation 52, wherein the image data includes first time data corresponding to the time that the image data was generated by the camera, the first biomeasurement includes second time data corresponding to the time that the biomeasurement data was generated by the sensor, and the comparison is between the first time data and the second time data.

Alternative Implementation 57. The method of alternative implementation 52, wherein the image is a still image of the at least the portion of the subject.

Alternative Implementation 58. The method of alternative implementation 52, wherein the image is a video image of the at least the portion of the subject.

Alternative Implementation 59. A system comprising: a control system comprising one or more processors; and a memory having stored thereon machine readable instructions; wherein the control system is coupled to the memory, and the method of any one of alternative implementations 1-58 is implemented when the machine executable instructions in the memory are executed by at least one of the one or more processors of the control system.

Alternative Implementation 60. A system for communicating one or more indications to a subject, the system comprising a control system configured to implement the method of any one of alternative implementations 1 to 58.

Alternative Implementation 61. A computer program product comprising instructions which, when executed by a computer, cause the computer to carry out the method of any one of alternative implementations 1 to 58.

Alternative Implementation 62. The computer program product of alternative implementation 62, wherein the computer program product is a non-transitory computer readable medium.

Alternative Implementation 63. A system comprising: a camera configured to generate image data that is reproducible as an image of at least a portion of a subject; a sensor configured to generate first biomeasurement data associated with the subject; a control system comprising one or more processors; and a memory having stored thereon machine readable instructions that are executable by the one or more processors to cause the control system to: verify a first biomeasurement of the subject based at least in part on the image data and the biomeasurement data; compare the first verified biomeasurement to a predetermined threshold; and determine a first level of access for the subject to one or more locations based at least in part on the comparison between the first verified biomeasurement and the predetermined threshold.

One or more elements or aspects or steps, or any portion (s) thereof, from one or more of any of alternative implementations 1-63 above can be combined with one or more elements or aspects or steps, or any portion(s) thereof, from one or more of any of the other alternative implementations 1-63 or combinations thereof, to form one or more additional implementations and/or claims of the present disclosure.

While the present disclosure has been described with reference to one or more particular embodiments and implementations, those skilled in the art will recognize that many changes may be made thereto without departing from the spirit and scope of the present disclosure. Each of these embodiments and implementations and obvious variations thereof is contemplated as falling within the spirit and scope of the present disclosure, which is set forth in the claims that follow.

What is claimed is:

1. A method comprising:
generating, via a camera of an electronic device, video data that is reproducible as a visual video clip of at least a portion of a subject, the video data including first time data corresponding to a time that the video data was generated by the camera of the electronic device;
determining, via a biomeasurement device, a first biomeasurement associated with the subject;
generating a data file including (i) the first biomeasurement associated with the subject, (ii) at least a portion of the video data, and (iii) second time data associated with the first biomeasurement; and
verifying the first biomeasurement associated with the subject based at least in part on the video data included in the generated data file, the verifying the first biomeasurement including comparing the second time data associated with the first biomeasurement with the first time data corresponding to the time that the video data was generated by the camera of the electronic device.

2. The method of claim 1, further comprising transmitting the generated data file to a server, wherein the server performs the verifying of the first biomeasurement.

3. The method of claim 1, wherein the verifying the first biomeasurement is performed by the electronic device.

4. The method of claim 1, further comprising analyzing at least a portion of the video data using aa facial recognition algorithm to identify the subject, cii) an object recognition algorithm to identify the biomeasurement device, or (iii) both (i) and (ii).

5. The method of claim 1, wherein the biomeasurement device includes a thermometer, a temperature sensor, a heart rate sensor, a respiration sensor, a perspiration sensor, an EKG sensor, a blood pressure sensor, a blood glucose sensor, an optical sensor, an electrochemical sensor, or any combination thereof.

6. The method of claim 1, further comprising comparing the first biomeasurement to a predetermined threshold.

7. The method of claim 6, wherein the first biomeasurement is a body temperature of the subject and the predetermined threshold is a body temperature indicative of a fever.

8. The method of claim 6, further comprising, prior to the comparing, modifying the predetermined threshold based at least in part on a profile associated with the subject, a second biomeasurement of the subject, an ambient temperature, the first time data, or any combination thereof.

9. The method of claim 8, wherein the second biomeasurement of the subject is a heart rate of the subject, a respiration rate of the subject, a perspiration rate of the subject, an activity level of the subject, or any combination thereof.

10. The method of claim 6, further comprising, responsive to the first biomeasurement of the subject exceeding the predetermined threshold, transmitting an alert to the subject, one or more third parties, or both.

11. The method of claim 1, wherein the second time data includes a time at which the first biomeasurement was approximately determined.

12. The method of claim 1, wherein the first biomeasurement is associated with a sample taken from the subject, and the second time data includes a time at which the sample was approximately taken from the subject.

13. A method comprising:
generating, via a camera of an electronic device, video data that is reproducible as a visual video clip of at least a portion of a subject;
determining, via a biomeasurement device, a first biomeasurement associated with the subject;
generating a data file including (i) the first biomeasurement associated with the subject, (ii) at least a portion of the video data, and (iii) first time data associated with the first biomeasurement;
verifying the first biomeasurement associated with the subject based at least in part on the video data included in the generated data file; and
comparing the first biomeasurement to a predetermined threshold, the first biomeasurement including a body temperature of the subject and the predetermined threshold including a body temperature indicative of a fever.

14. The method of claim 13, further comprising transmitting the generated data file to a server, wherein the server performs the verifying of the first biomeasurement.

15. The method of claim 13, wherein the verifying the first biomeasurement is performed by the electronic device.

16. The method of claim 13, further comprising analyzing at least a portion of the video data using (i) a facial recognition algorithm to identify the subject, (ii) an object recognition algorithm to identify the biomeasurement device, or (iii) both (i) and (ii).

17. The method of claim 13, wherein the biomeasurement device includes a thermometer, a temperature sensor, a heart rate sensor, a respiration sensor, a perspiration sensor, an EKG sensor, a blood pressure sensor, a blood glucose sensor, an optical sensor, an electrochemical sensor, or any combination thereof.

18. The method of claim 13, further comprising, prior to the comparing, modifying the predetermined threshold based at least in part on a profile associated with the subject, a second biomeasurement of the subject, an ambient temperature, the first time data, or any combination thereof.

19. The method of claim 18, wherein the second biomeasurement of the subject is a heart rate of the subject, a respiration rate of the subject, a perspiration rate of the subject, an activity level of the subject, or any combination thereof.

20. The method of claim 13, further comprising, responsive to the first biomeasurement of the subject exceeding the predetermined threshold, transmitting an alert to the subject, one or more third parties, or both.

21. The method of claim 13, wherein the first time data includes a time at which the first biomeasurement was approximately determined.

22. The method of claim 13, wherein the first biomeasurement is associated with a sample taken from the subject, and the first time data includes a time at which the sample was approximately taken from the subject.

* * * * *

UNITED STATES PATENT AND TRADEMARK OFFICE
CERTIFICATE OF CORRECTION

PATENT NO. : 11,103,160 B2
APPLICATION NO. : 17/148438
DATED : August 31, 2021
INVENTOR(S) : Emalfarb Page 1 of 1

It is certified that error appears in the above-identified patent and that said Letters Patent is hereby corrected as shown below:

In the Claims

At Column 45, Lines 30-31 (Claim 4, Lines 2-3), please delete "using aa facial recognition algorithm to identify the subject, cii) an object recognition" and insert --using (i) a facial recognition algorithm to identify the subject, (ii) an object recognition-- therefor.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*